US008790358B2

(12) United States Patent
Baker et al.

(10) Patent No.: US 8,790,358 B2
(45) Date of Patent: Jul. 29, 2014

(54) METHODS AND APPARATUS FOR MAKING ANASTOMOTIC CONNECTIONS LARGER THAN THE GRAFT CONDUIT

(75) Inventors: Matthew Baker, Plymouth, MN (US); Michael P. Brenzel, St. Paul, MN (US); David Costello, Waconia, MN (US); Todd A. Krinke, Rockford, MN (US); John Logan, Plymouth, MN (US); Alex A. Peterson, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1720 days.

(21) Appl. No.: 10/813,447

(22) Filed: Mar. 29, 2004

(65) Prior Publication Data
US 2004/0267290 A1   Dec. 30, 2004

Related U.S. Application Data

(60) Provisional application No. 60/459,234, filed on Mar. 28, 2003, provisional application No. 60/519,534, filed on Nov. 12, 2003.

(51) Int. Cl.
*A61B 17/08* (2006.01)
(52) U.S. Cl.
USPC ................ 606/153; 623/1.13; 606/8
(58) Field of Classification Search
USPC ......... 623/1.13; 606/151, 153, 185, 219, 139, 606/8
See application file for complete search history.

(56) References Cited

U.S. PATENT DOCUMENTS

| 5,904,697 | A | * | 5/1999 | Gifford et al. ................ 606/153 |
| 5,976,178 | A | | 11/1999 | Goldsteen et al. ................ 623/1 |
| 6,152,937 | A | | 11/2000 | Peterson et al. ................ 606/153 |

(Continued)

FOREIGN PATENT DOCUMENTS

| WO | WO 99/38441 | 8/1999 | ............. A61B 17/11 |
| WO | WO 00/33745 | 6/2000 | ............. A61B 17/11 |

(Continued)

OTHER PUBLICATIONS

PCT US00/15259 (Published Dec. 14, 2000).*

*Primary Examiner* — Corrine M McDermott
*Assistant Examiner* — Son Dang
(74) *Attorney, Agent, or Firm* — Lerner, David, Littenberg, Krumholz & Mentlik, LLP

(57) ABSTRACT

Methods and apparatus for making an anastomotic connection between an opening at an end of a graft conduit and an aperture in a side wall of a body tissue conduit using a hollow connector assembly are provided, wherein the cross-sectional area of the anastomotic connection is larger than that of the graft conduit. The tissue about the opening is introduced about and retained by first members of a distal portion of the connector assembly held by a loading tool. A delivery tool then collapses a proximal portion defined by second members of the connector assembly and delivers the second members into the lumen of the body tissue conduit via the aperture. Upon inserting the second members into the body tissue conduit, the delivery tool is disemployed and the second members expand such that they press against the interior wall of the body tissue conduit and such that the first members are held within the aperture against a medial wall of the body tissue conduit.

46 Claims, 45 Drawing Sheets

(56) References Cited

U.S. PATENT DOCUMENTS

| | | | |
|---|---|---|---|
| 6,273,912 B1 * | 8/2001 | Scholz et al. | 623/1.31 |
| 6,428,550 B1 | 8/2002 | Vargas et al. | 606/153 |
| 6,602,263 B1 * | 8/2003 | Swanson et al. | 606/153 |
| 6,682,540 B1 * | 1/2004 | Sancoff et al. | 606/153 |
| 6,699,256 B1 * | 3/2004 | Logan et al. | 606/153 |
| 2002/0022853 A1 | 2/2002 | Swanson et al. | 606/155 |
| 2002/0169466 A1 | 11/2002 | Peterson et al. | 606/153 |
| 2002/0183769 A1 | 12/2002 | Swanson et al. | 606/153 |
| 2004/0068217 A1 | 4/2004 | Hindrichs et al. | 602/41 |
| 2004/0068279 A1 | 4/2004 | Hindrichs et al. | 606/153 |
| 2004/0093077 A1 * | 5/2004 | White et al. | 623/1.16 |

FOREIGN PATENT DOCUMENTS

| | | | |
|---|---|---|---|
| WO | WO 00/74579 | 12/2000 | A61B 17/32 |
| WO | WO 01/34037 | 5/2001 | A61B 17/08 |
| WO | WO 02/091952 | 11/2002 | A61F 2/00 |
| WO | WO 03/026475 | 4/2003 | |

* cited by examiner

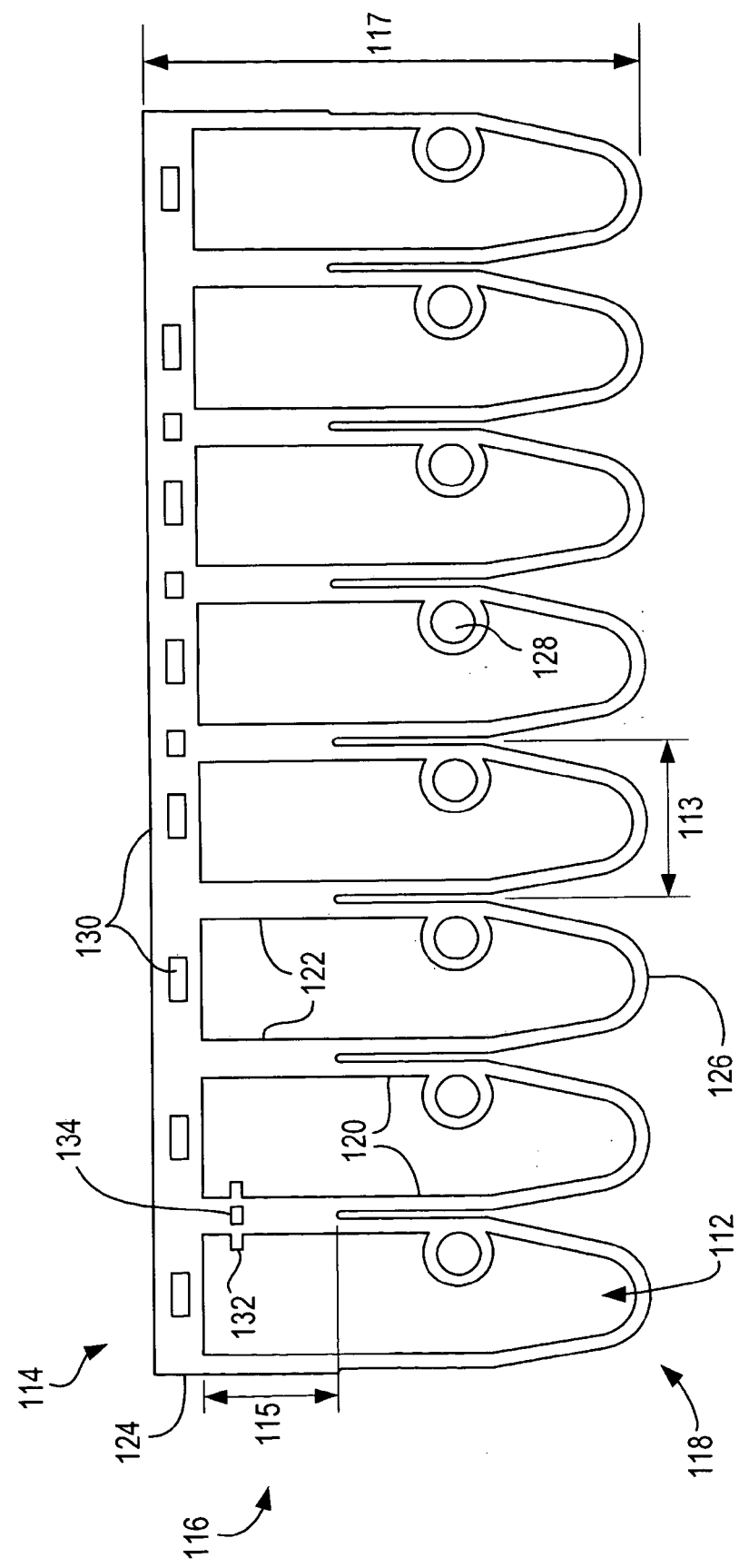

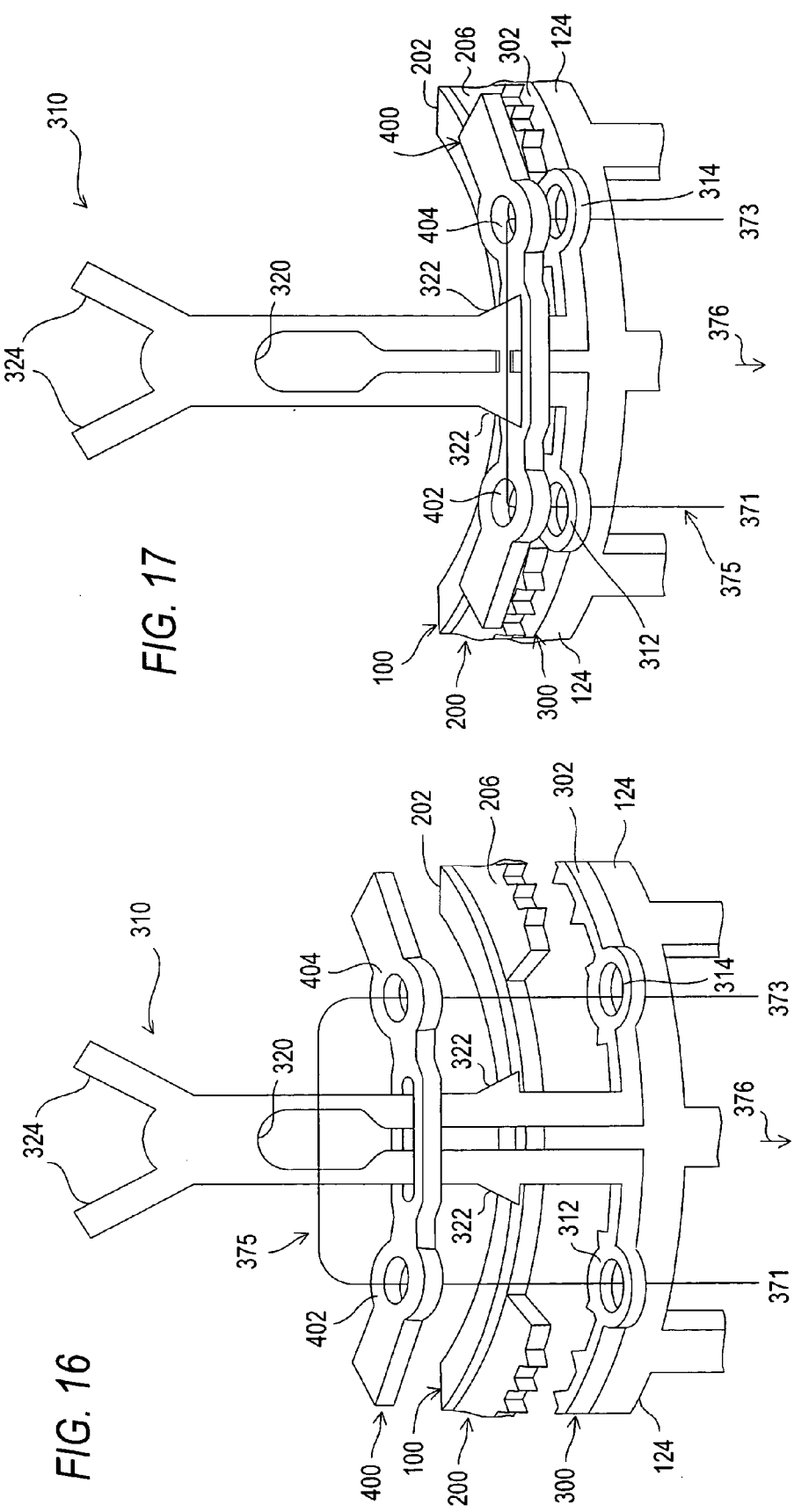

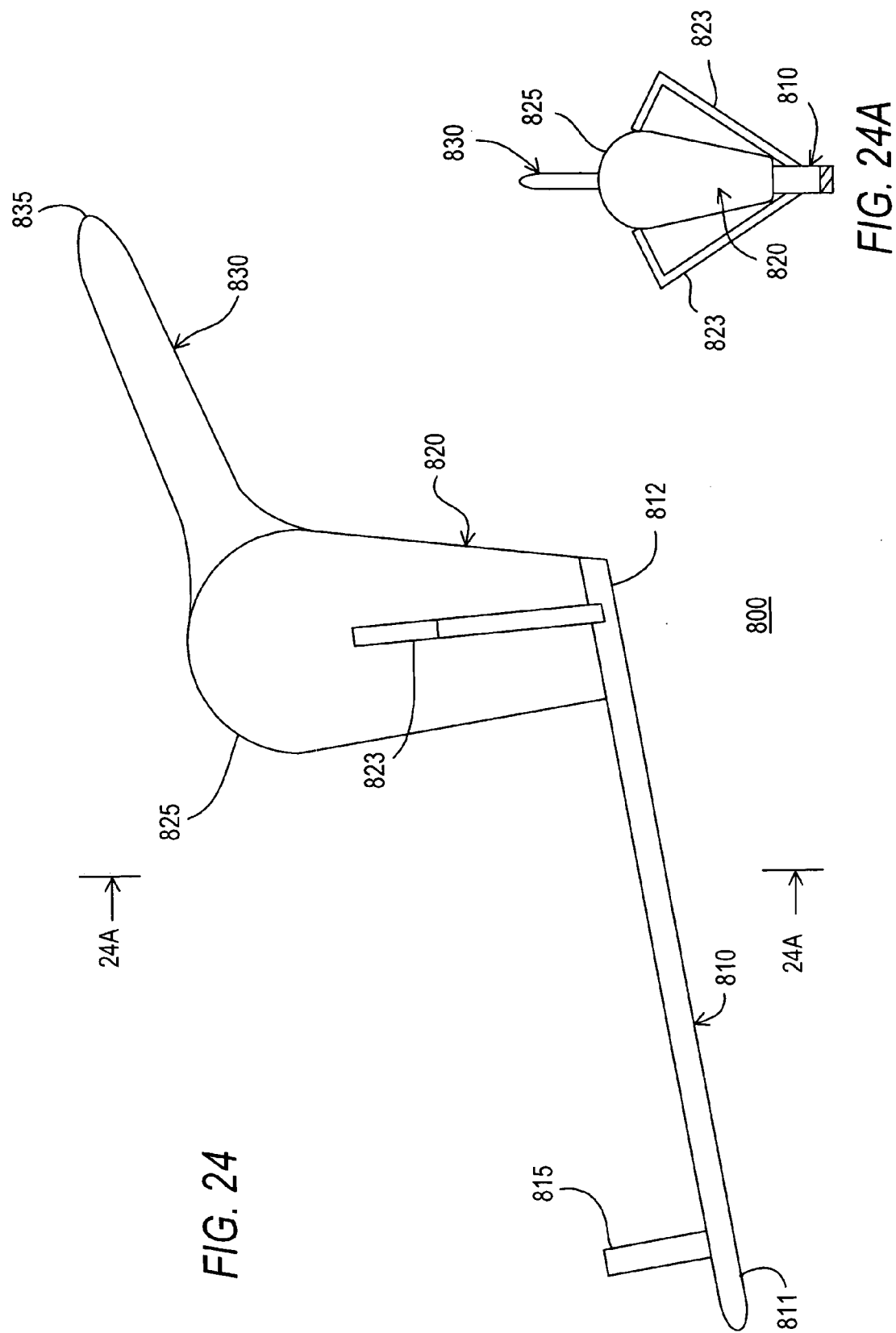

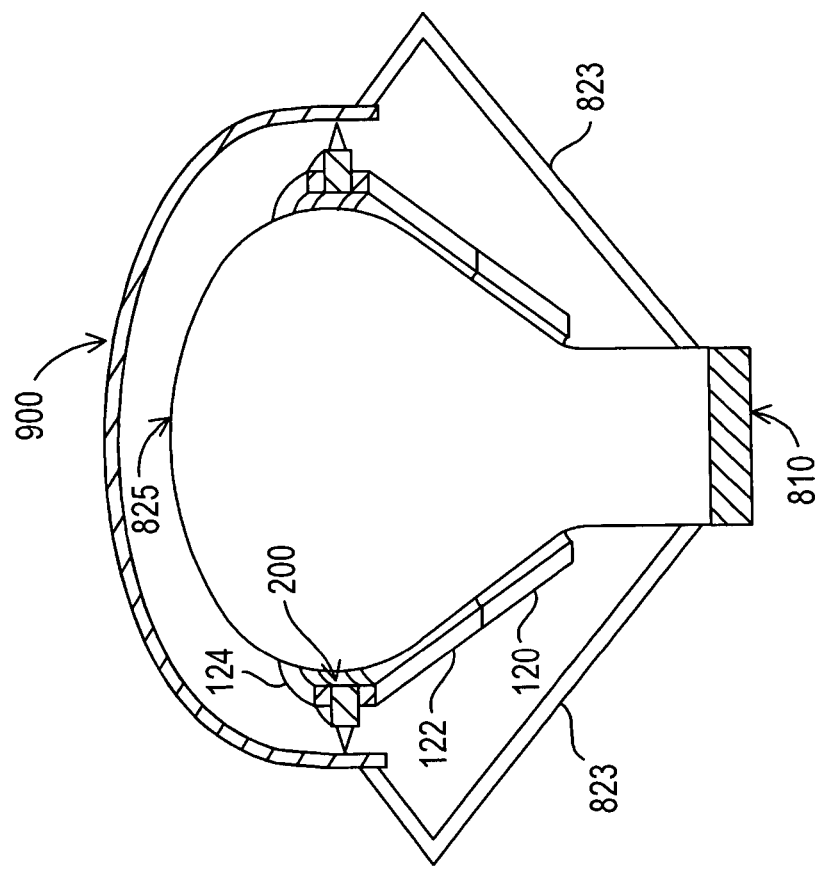

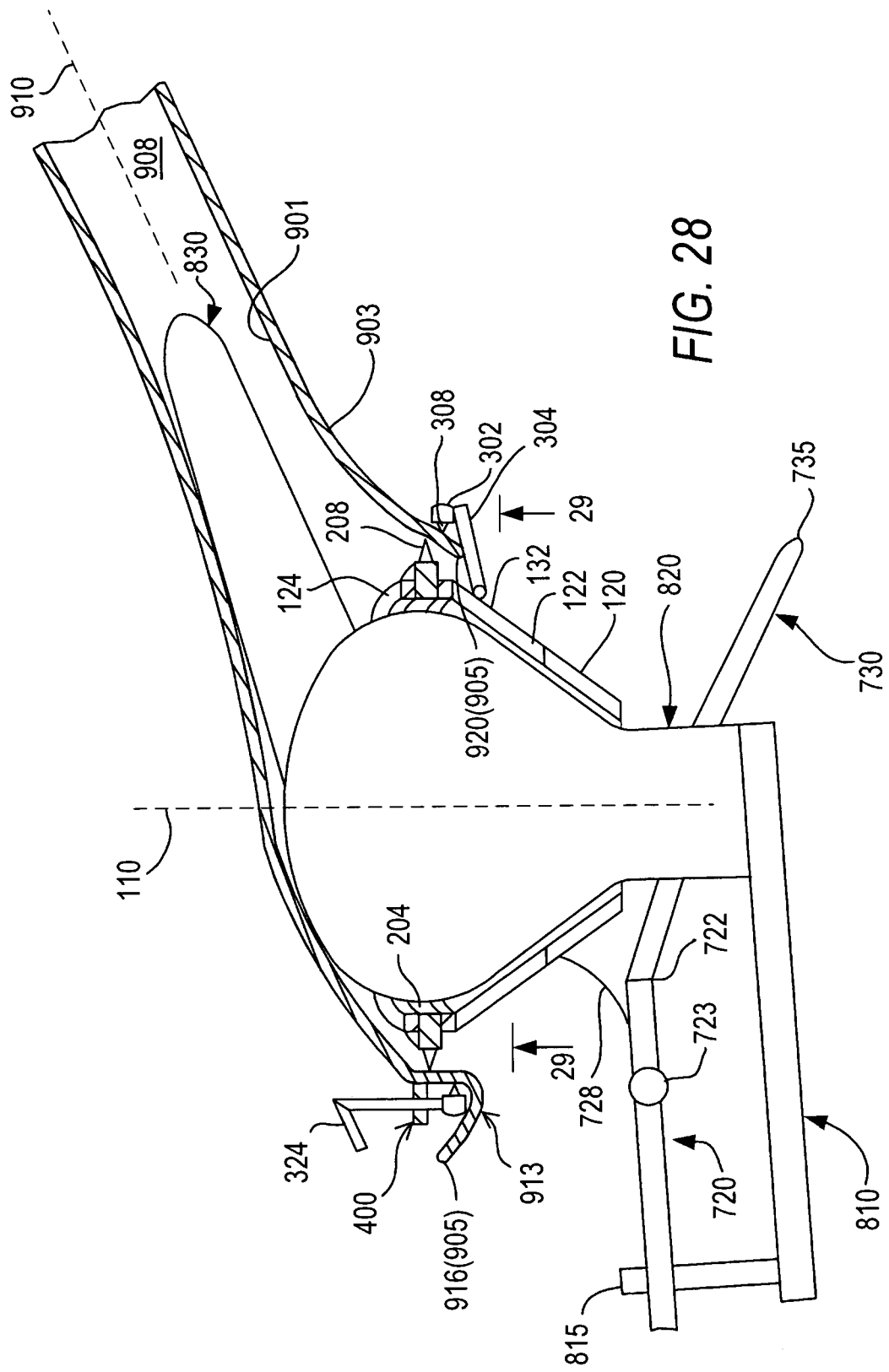

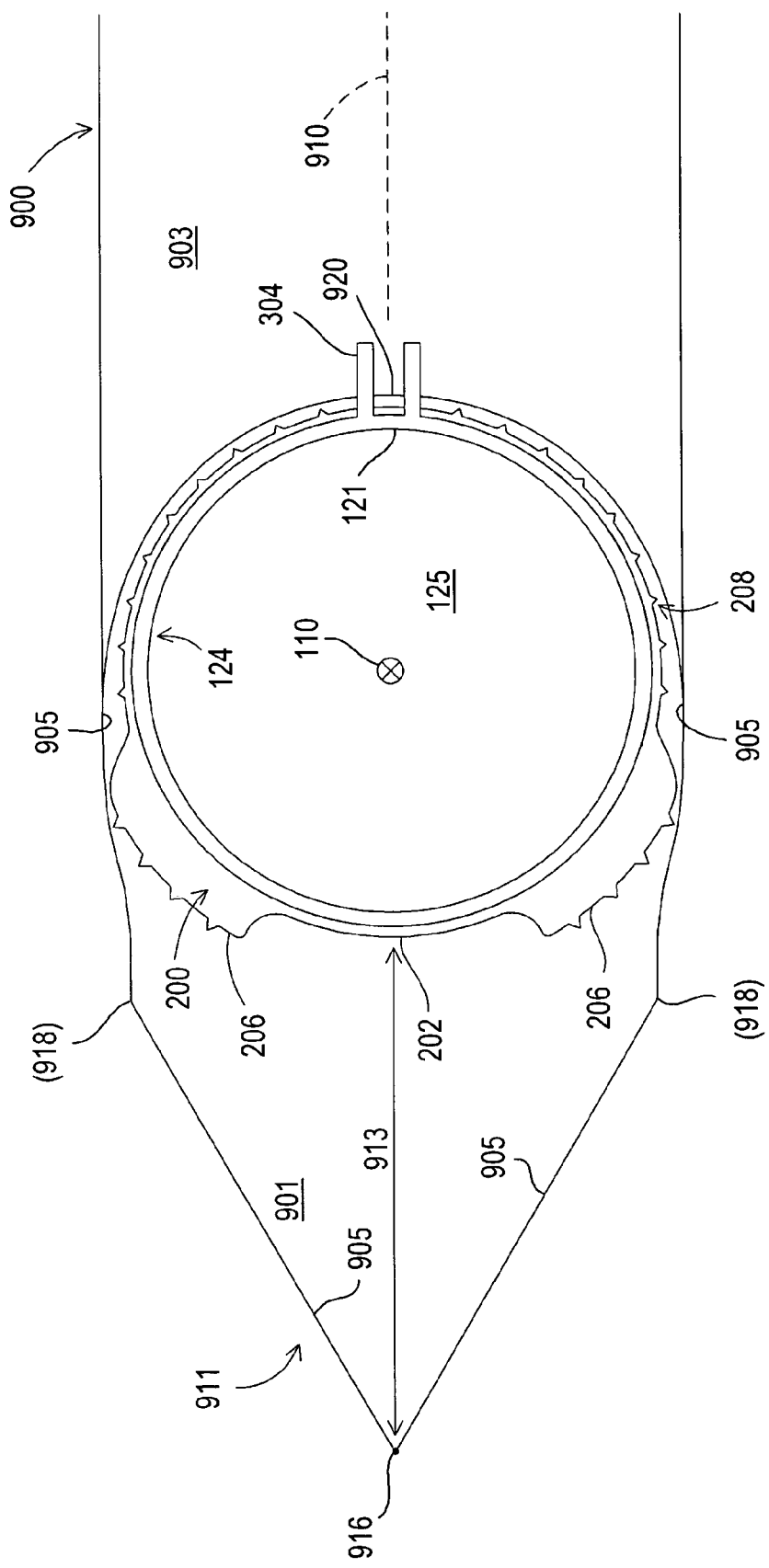

METHODS AND APPARATUS FOR MAKING ANASTOMOTIC CONNECTIONS LARGER THAN THE GRAFT CONDUIT

This application claims the benefit of U.S. provisional patent application No. 60/459,234, filed Mar. 28, 2003, and U.S. provisional patent application No. 60/519,534, filed Nov. 12, 2003. Both of these prior applications are hereby incorporated by reference herein in their entireties.

BACKGROUND OF THE INVENTION

This invention relates to medical grafting apparatus and methods for creating anastomoses and, more particularly, to apparatus and methods for creating an aortic anastomoses whose ostium diameter is larger than that of the graft conduit.

There are many medical procedures in which it is necessary to make an anastomotic connection between two tubular body fluid conduits in a patient. An anastomotic connection (or anastomosis) is a connection which allows body fluid flow between the lumens of the two conduits that are connected, preferably without allowing body fluid to leak out of the conduits at the location of the connection (see, for example, Peterson et al. U.S. patent application Ser. No. 10/147,208, filed May 14, 2002, which is hereby incorporated by reference herein in its entirety). As just one example of a procedure in which an anastomosis is needed, in order to bypass an obstruction in a patient's coronary artery, a tubular graft attached to the coronary artery downstream from the obstruction may be supplied with aortic blood via an anastomosis to the aorta. The anastomosis may be between the end of the graft and an aperture in the side wall of the aorta (a so-called end-to-side anastomosis), or the anastomosis may be between an aperture in the side wall of the graft and an aperture in the side wall of the aorta (a so-called side-to-side anastomosis).

The graft may be natural conduit, synthetic conduit, or a combination of natural and synthetic conduits. If natural conduit is used, it may be wholly or partly relocated from elsewhere in the patient (e.g., wholly relocated saphenous vein graft ("SVG"), radial artery, or partly relocated internal mammary artery ("IMA")).

In the case of making a conventional anastomosis utilizing commercially available connectors at the proximal anastomosis between the graft and the aorta, certain difficulties may arise. First, the relative sizes of the aorta and the graft are different. Currently, the ostium diameter of the anastomosis utilizing commercially available connectors is limited by and usually smaller than the diameter of the graft. The resulting quality and amount of flow between the vein graft and the aorta, along with the provision of an effective hemodynamic seal between the two vessels, is often dependent upon the physician's skill in making an effective junction therebetween.

Second, a conventional end-to-side anastomosis utilizing commercially available connectors typically joins the graft conduit to the aorta at a substantially perpendicular angle with respect to the lumen of the aorta, thus forming a junction at the wall of the aorta. Further away from this junction, the vein graft tends to lie against the heart structure, or substantially parallel to the aorta. The transition of the vein graft from a substantially perpendicular juncture to the aorta to a substantially parallel position with respect to the aorta wall often requires non-traditional placement of the anastomosis different from that of typical hand-sewn anastomoses.

Third, it is desirable to provide an anastomosis with a diameter equal to or larger than the diameter of the smaller vessel being joined in order to allow as much area as possible for the natural healing response.

Accordingly, it is an object of the invention to provide apparatus and methods for making an anastomosis whose ostium diameter is larger than that of the graft.

It is also an object of the invention to provide apparatus and methods for making an anastomosis whose take-off is angled rather than tangential or perpendicular.

SUMMARY OF THE INVENTION

It is therefore an object of this invention to provide apparatus and methods for making an anastomosis whose ostium diameter is larger than that of the graft.

It is therefore also an object of the invention to provide apparatus and methods for making an anastomosis whose take-off is angled rather than tangential or perpendicular.

In accordance with the present invention, an apparatus including a connector assembly is provided to create a hollow anastomotic connection between tubular body fluid vessels in a patient. A particular application of the invention is to join a graft conduit to a patient's aorta in an end-to-side anastomosis whose ostium diameter is larger than that of the graft conduit. In a first embodiment of the present invention, the connector assembly has a first set of members or graft retention features at its distal end that engage a first vessel (e.g., the graft conduit), and a second set of members or inside aortic fingers at its proximal end that contact a second vessel (e.g., the aorta) and press it towards the first vessel. A graft attachment band or lid is pivotally attached at the distal end of the connector. The inside aortic fingers are constrained by an aortic delivery tool such that the connector assembly is held about the medial portion of a "S-shaped" graft loading tool.

Tissue at a prepared end of the graft conduit is slid onto the distal portion of the loading tool, pulled through the band, and draped over the graft retention features at the distal end of the connector assembly. The band is then pivotally lowered to snap-fit with the distal end of the connector assembly to fixedly engage the graft conduit thereto.

The aortic delivery tool unconstrains the inside aortic fingers such that the graft loading tool can be removed from the graft conduit and through the connector assembly. Then the delivery tool re-constrains the inside aortic fingers such that they are positioned to prevent trauma to the aorta when the proximal end of the connector assembly is introduced therein. The delivery tool has a structure which may release the inside aortic fingers therefrom after insertion into the aorta and to allow expansion of the proximal end of the connector assembly therein.

A method for creating the anastomosis may include introducing the prepared end of the graft conduit through the band of the connector assembly and then over its distal end to engage the graft conduit with the graft retention features of the connector assembly. At the operative site, an aperture may be made in the side wall of the aorta or any other body conduit that, is to be connected to the graft. The proximal end of the connector assembly may be deformed and the end of the graft conduit and the aperture in the aorta may be approximated so that the inside aortic fingers of the connector assembly extend into the aorta via the aperture. The connector assembly may reform so that it presses together the exterior wall of the aorta and the end of the graft conduit annularly about the aperture in the aorta.

It should be noted that the terms vessel and conduit are used interchangeable herein.

BRIEF DESCRIPTION OF THE DRAWINGS

The above and other advantages of the invention will be made more apparent upon consideration of the following detailed description, taken in conjunction with the accompanying drawings, in which like reference characters refer to like parts throughout, and in which:

FIG. 8 is a planar development of the structure of an illustrative embodiment of a connector body constructed in accordance with the invention;

FIG. 16 is a closer front elevational view of a portion of the connector assembly of FIGS. 7, 7A, 14, and 15, in the intermediate position of FIG. 15, in accordance with the invention;

FIG. 17 is a closer front elevational view of a portion of the connector assembly of FIGS. 7, 7A, and 14-16, similar to FIG. 16, in a closed position, in accordance with the invention;

FIG. 24 is a side elevational view of a second component of the apparatus of FIGS. 19-23;

FIG. 24A is a side elevational view of the second component of the apparatus of FIGS. 19-24, taken from line 24A-24A of FIG. 24;

FIG. 27A is a simplified sectional view of the connector assembly of FIGS. 7, 7A, 14-19, and 27 in the open position of FIGS. 7, 7A, and 27, illustrated with the graft conduit of FIGS. 25-27 and with the apparatus of FIGS. 19-24 and 27, in a second stage of a procedure, in accordance with the invention, taken from line 27A-27A of FIG. 27, but with a portion of the connector assembly and a portion of the apparatus omitted;

FIG. 28 is a simplified sectional view, similar to FIG. 27, of the connector assembly of FIGS. 7, 7A, 14-19, and 27, in the closed position of FIGS. 17 and 18, illustrated with the graft conduit of FIGS. 25-27 and with the apparatus of FIGS. 19-24 and 27, in a later stage of a procedure, in accordance with the invention;

FIG. 29 is a bottom elevational view of the connector assembly of FIGS. 7, 7A, 14-19, 27, and 28, in the closed position of FIGS. 17, 18, and 28, illustrated with the graft conduit of FIGS. 25-28, in the later stage of the procedure of FIG. 28, taken from line 29-29 of FIG. 28, but with a portion of the connector assembly omitted;

DETAILED DESCRIPTION OF THE INVENTION

Although the invention has other possible uses, the invention will be fully understood from the following explanation of its use in providing a bypass around an obstruction in a patient's vascular system.

In some embodiments of the present invention, certain types of cuts may be made at the end of a graft conduit prior to creating an end-to-side anastomosis between the graft conduit and the aorta of a patient such that the ostium diameter of the anastomosis may be larger than that of the graft conduit. (It should be noted that, although apparatus and methods for making anastomoses generally may be described herein in relation to those whose ostium diameter is larger than that of the graft, the present invention also relates to making anastomoses whose ostium cross-sectional area, and not necessarily diameter, is larger than that of the graft, for example, when the ostium is oval-shaped.)

Figure 1:
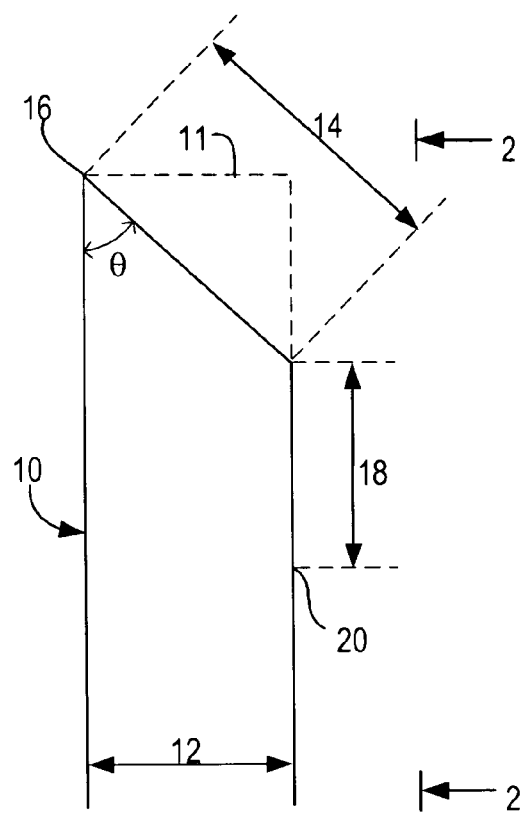
FIG. 1 is a side elevational view of a graft conduit prepared with a spatulated cut in accordance with the invention.
Figure 2:
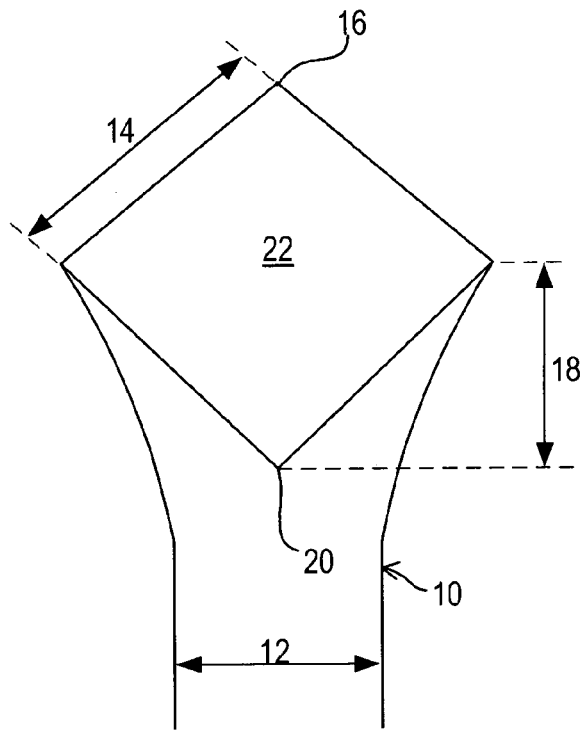
FIG. 2 is a front elevational view of the graft conduit of FIG. 1, fileted open, taken from line 2-2 of FIG. 1.

FIGS. 1 and 2 show a length of a graft 10, having an inner diameter 12, prepared with a "cobra head" or "spatulated" cut. Firstly, an incision 14 oblique to the longitudinal axis of graft 10 at an angle θ is made at an open end 11 of graft 10 from a point 16, referred to herein as the "toe." Secondly, a lengthwise axial incision 18, which may be substantially the same length as incision 14, is made from the end of incision 14 to a point 20 along the length of the graft, referred to herein as the "heel." The cross-sectional area of opening 22 from toe 16 to heel 20 provided by the spatulated cut of graft 10 increases as the length of incision 18 increases and/or the length of incision 16 increases (i.e., as angle θ decreases), thereby allowing the ostium cross-sectional area of an anastomosis made with spatulated graft 10 to be larger than that of an anastomosis simply made with open end 11 of the native graft.

Figure 3:
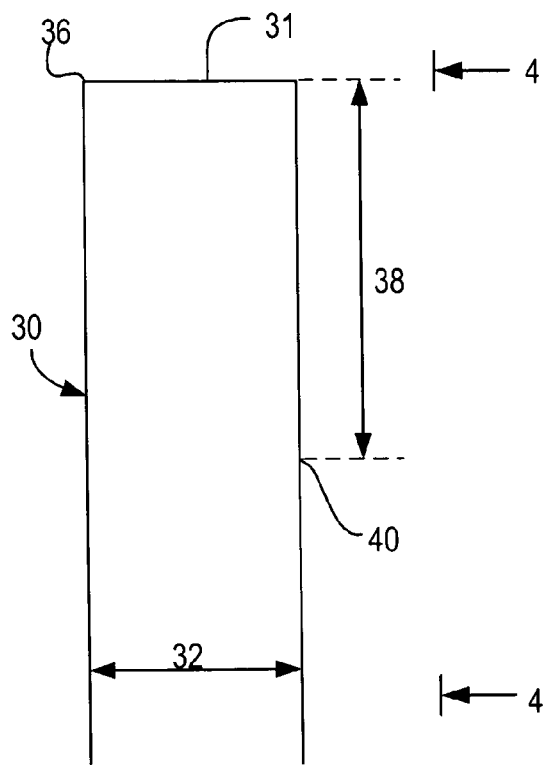
FIG. 3 is a side elevational view of a graft conduit prepared with an axial cut in accordance with the invention.
Figure 4:
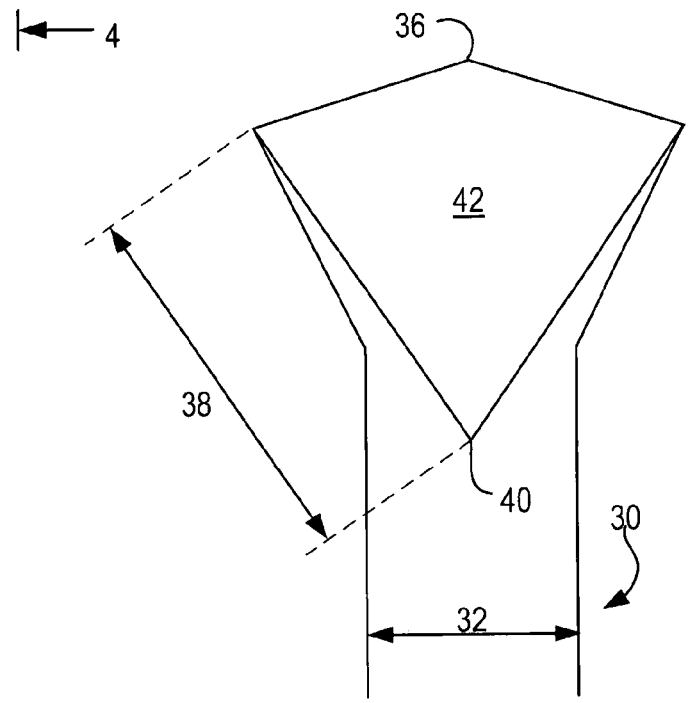
FIG. 4 is a front elevational view of the graft conduit of FIG. 3, fileted open, taken from line 4-4 of FIG. 3.

FIGS. 3 and 4 show an other embodiment of the present invention, wherein the length of a graft 30 having an inner diameter 32 is prepared with an "axial" cut. A lengthwise axial incision 38 is made at open end 31 of graft 30 from a point diametrically opposite toe point 36 to a heel point 40 along the length of graft 30. The cross-sectional area of opening 42 from toe 36 to heel 40 provided by the axial cut of graft 30 increases as the length of incision 38 increases, thereby allowing the ostium cross-sectional area of an anastomosis made with axially cut graft 30 to be larger than that of an anastomosis simply made with open end 31 of the native graft.

Figure 5:
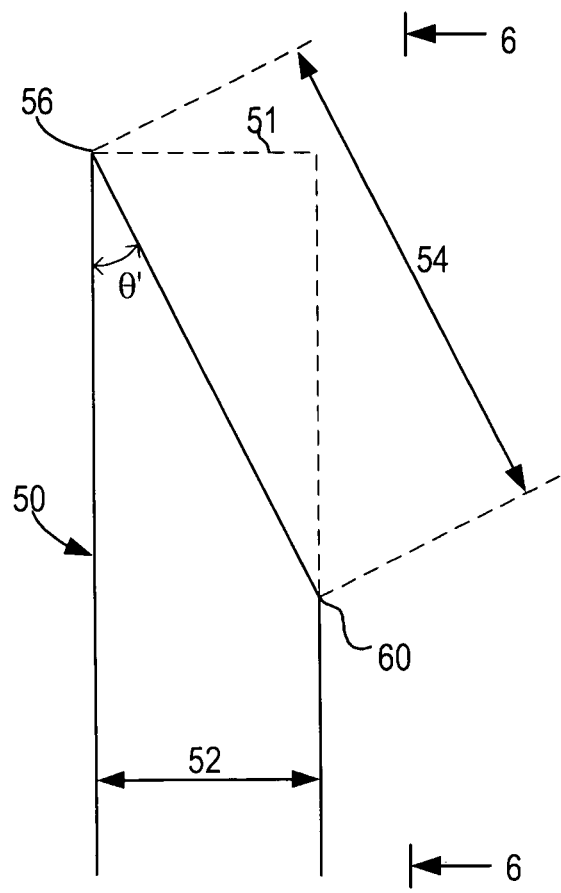
FIG. 5 is a side elevational view of a graft conduit prepared with an oblique cut in accordance with the invention.
Figure 6:
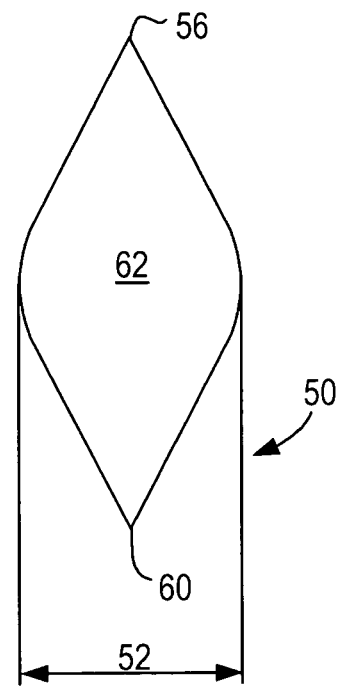
FIG. 6 is a front elevational view of the graft conduit of FIG. 5, fileted open, taken from line 6-6 of FIG. 5.

FIGS. 5 and 6 show yet an other embodiment of the present invention, wherein the length of a graft 50 having an inner diameter 52 is prepared with an "oblique" cut. An incision 54 oblique to the longitudinal axis of graft 50 at an angle θ' is made at an open end 51 of graft 50 from a toe point 56 to a heel point 60 along the length of graft 50. The cross-sectional area of opening 62 from toe 56 to heel 60 provided by the oblique cut of graft 50 increases as the length of incision 54 increases (i.e., as angle θ' decreases), thereby allowing the ostium cross-sectional area of an anastomosis made with obliquely cut graft 50 to be larger than that of an anastomosis simply made with open end 51 of the native graft.

It should be noted that, in order to provide an opening with a cross-sectional area that is larger than that provided by a conventional transverse cut, the end of a graft conduit to be used in an aortic anastomosis may be prepared with various cuts other than those described above. As described hereinabove with respect to FIGS. 1-6, the length and type of each incision used while preparing a cut at an open end of a graft conduit may be adjusted based on the inner diameter of the graft conduit, the outer diameter of the connector, and amount of residual toe tissue of the graft conduit, for example, such that the cross-sectional area of the opening created may be customized to match the size and shape of the ostium of the connector used in making the aortic anastomosis.

Figure 7:
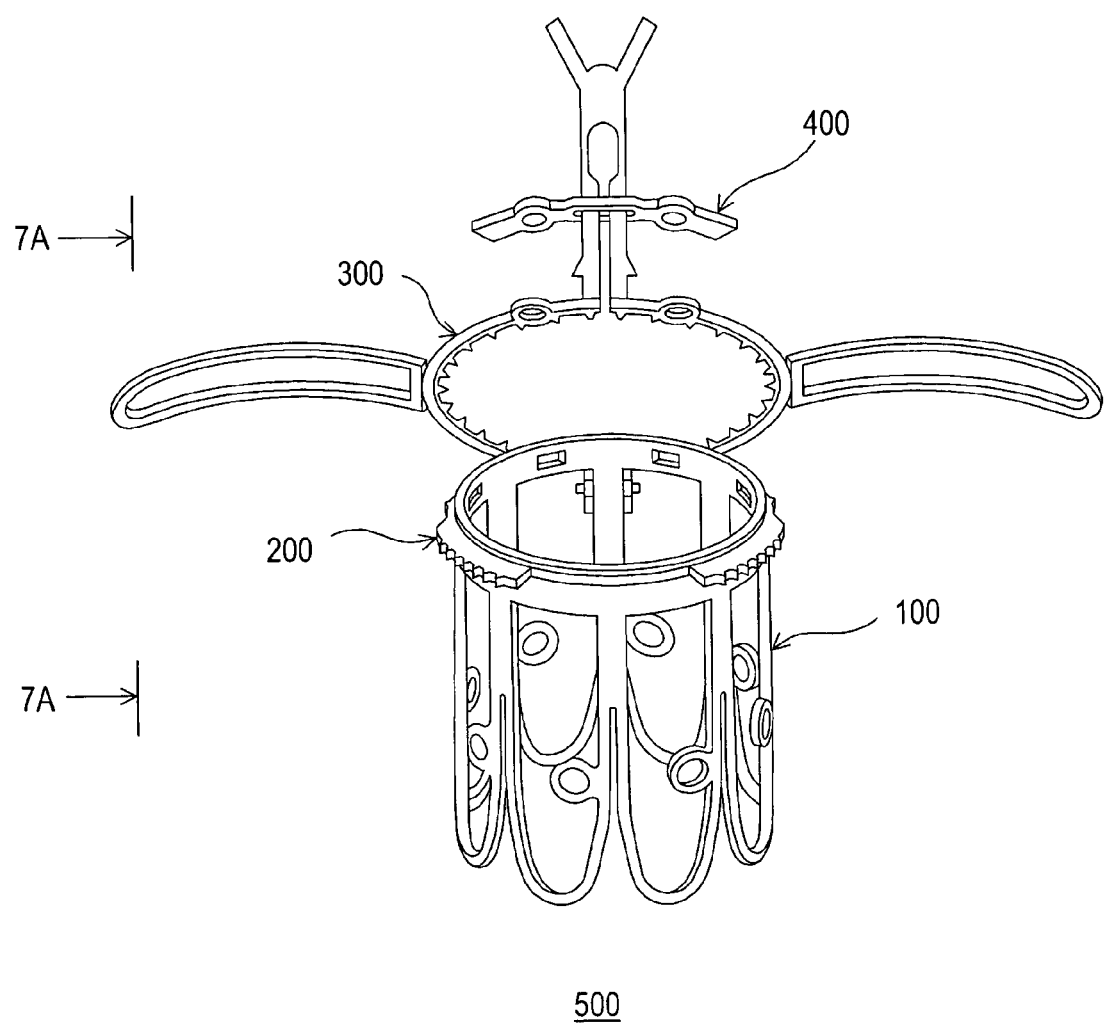
FIG. 7 is a front elevational view of a preferred embodiment of an assembled connector assembly, in an open position, in accordance with the invention.
Figure 7A:
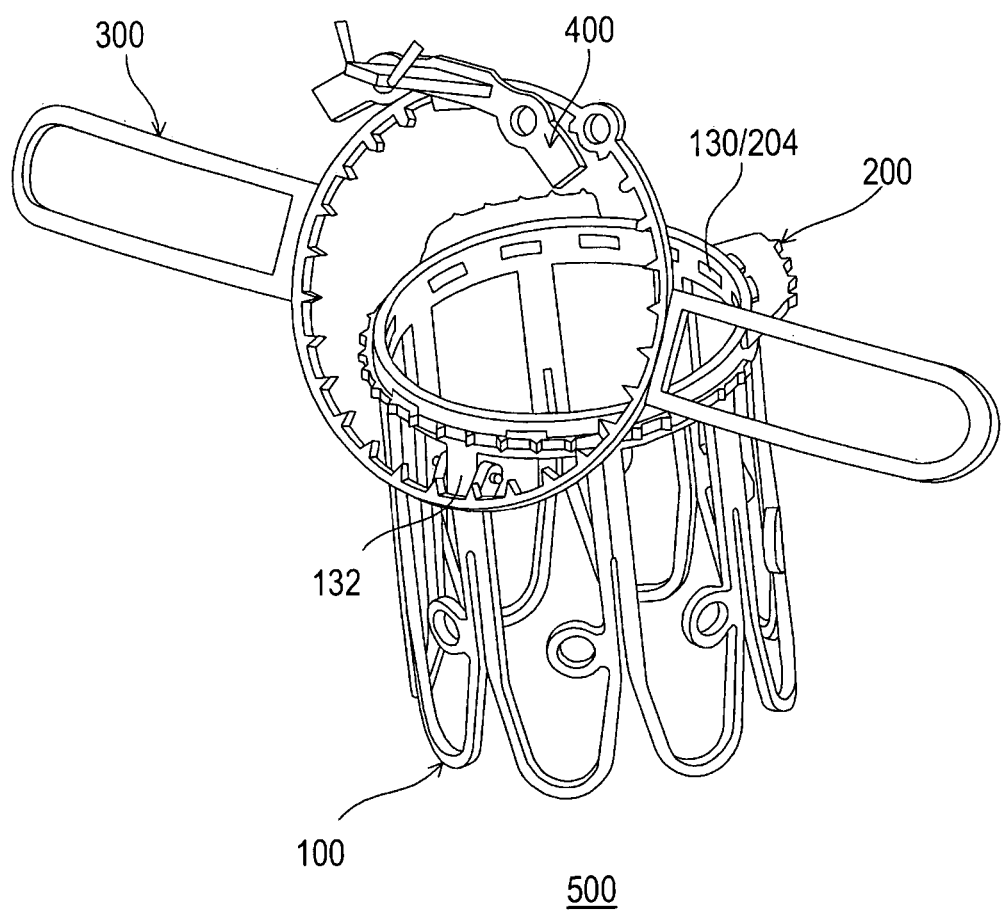
FIG. 7A is a rear elevational view of the assembled connector of FIG. 7, taken from line 7A-7A of FIG. 7.

FIGS. 7 and 7A show an illustrative connector assembly 500 to be used for making an aortic anastomosis using an end of a graft conduit prepared in any of the ways described above such that the ostium cross-sectional area is larger than that of the graft conduit. As shown, for example, there may generally be four components to connector assembly 500: a connector "body" 100 with inside aortic fingers, an "inside-the-graft" retaining element or ring 200 that may be fixed or part of connector body 100, an "outside-the-graft" retaining element or band 300 pivotally attached or attachable to connector body 100 at a point below "inside-the-graft" ring 200, and a locking or sliding collar 400 fitted about a portion of outside-the-graft band 300 for fastening outside-the-graft band 300 below inside-the-graft ring 200.

In a preferred embodiment, band 300 is allowed to pivot on connector body 100 at a point below ring 200 to facilitate loading of the graft. Outside-the-graft retaining band 300 has several features which allow it to function as a retaining feature. For example, the effective inner diameter of outside-the-graft retaining band 300 may be equal to or less than the effective outer diameter of inside-the-graft retaining ring 200. This interference fit between the two elements may facilitate a locking mechanism. Tissue retention features on the outside of inside-the-graft retaining ring 200 and tissue retention features on the inside of outside-the-graft retaining band 300 may allow deflection so that the band and ring can pass by each other to latch, but the shape and resulting direction of force may make release of this mechanism, or the ability for the band and ring to pass back the other way, to require significant force. The geometry of these features can take many forms other than those described herein without departing from the spirit and scope of the present invention. In another preferred embodiment, band 300 is attached about connector body 100 at least partially below ring 200 after the graft has been loaded about ring 200.

Components 100, 200, 300 and 400 may be constructed of nitinol, stainless steel, or any other suitable material, or combination thereof. The inside-the-graft retaining ring may or may not be attached to the connector body. The entire structure could be cut from one piece of nitinol tube and formed into the desired features, for example. Provided hereinbelow are brief descriptions of drawings in connection with the separate components of connector assembly 500.

Figure 9:
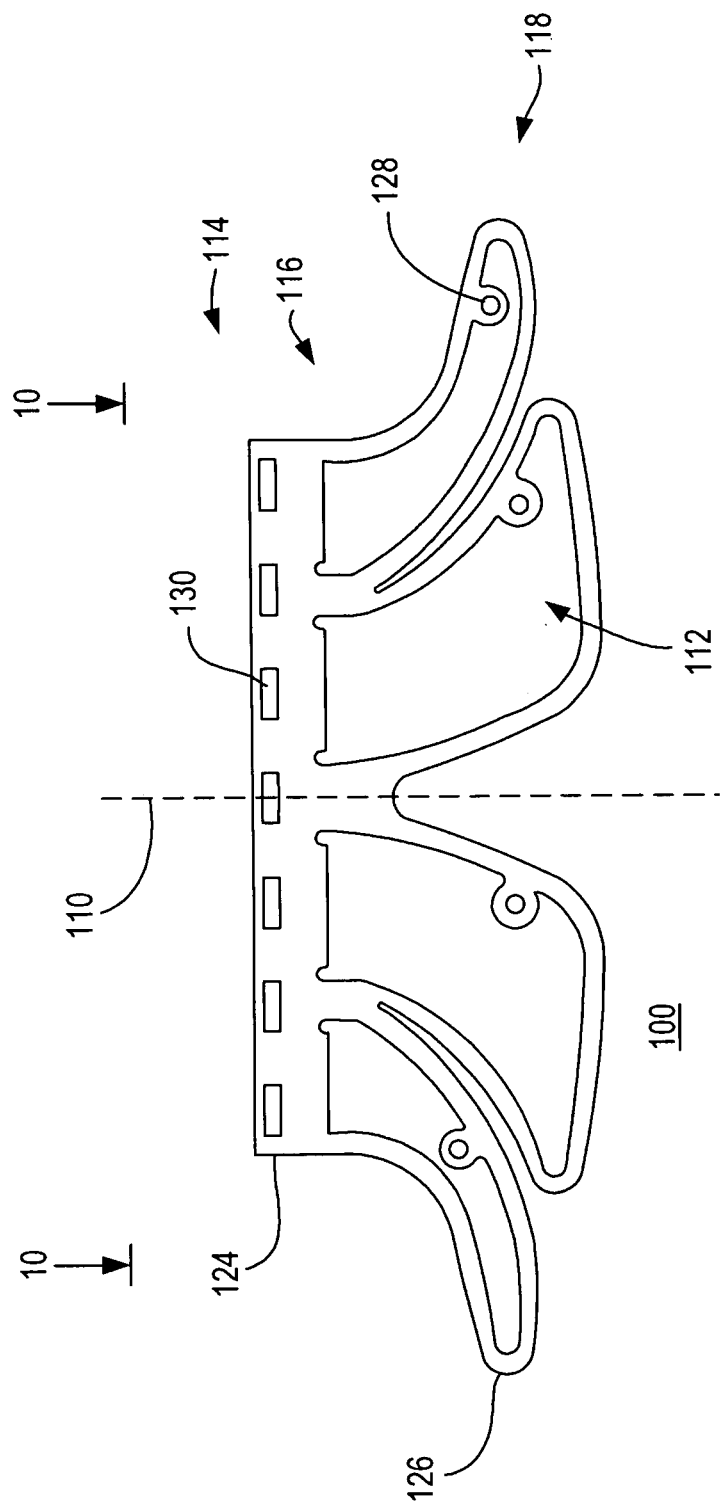
FIG. 9 is a partial perspective view of the connector body of FIG. 8, in an expanded configuration, in accordance with the invention.
Figure 10:
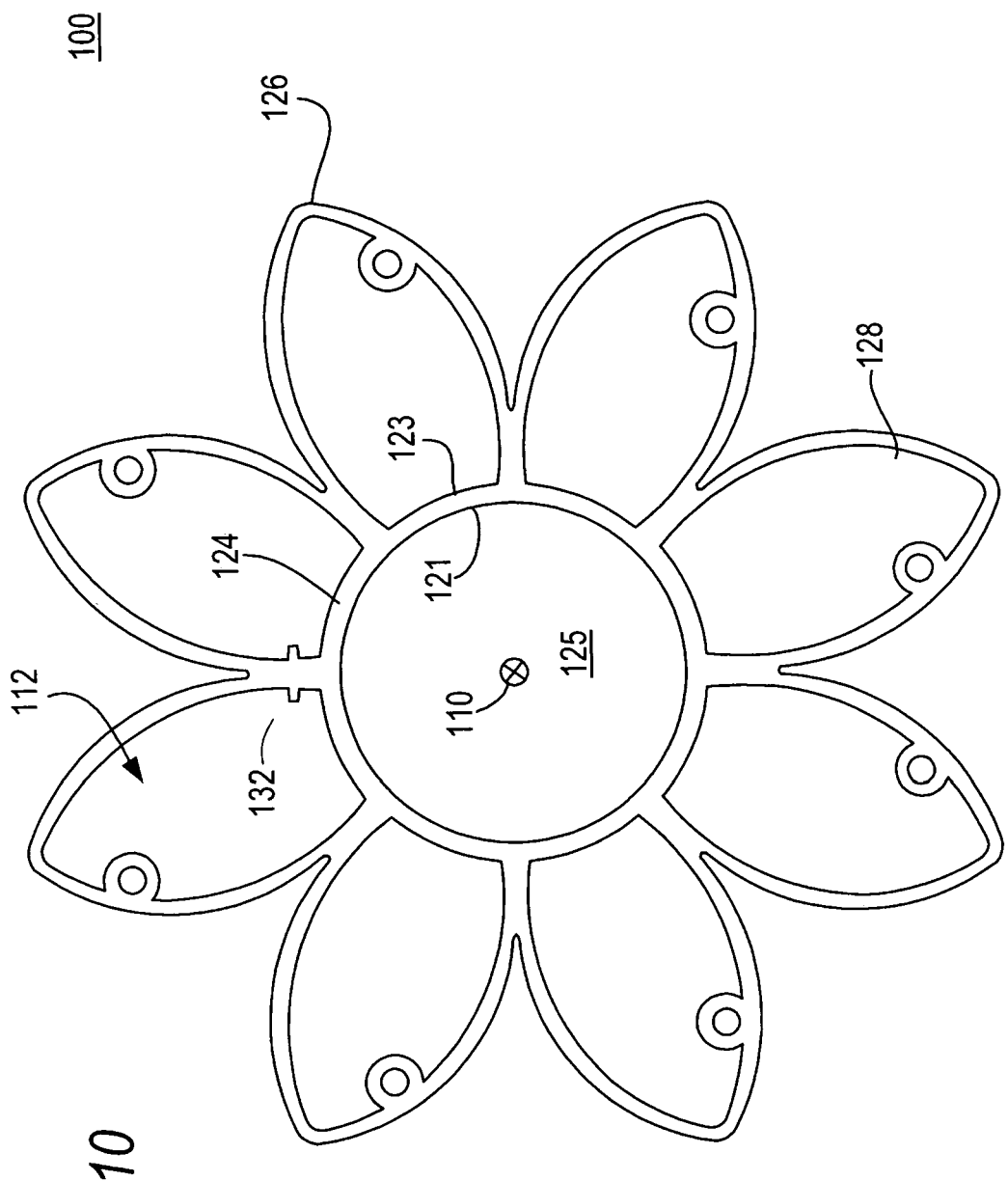
FIG. 10 is a top elevational view of the connector body of FIGS. 8 and 9, taken from line 10-10 of FIG. 9.

FIG. 8 shows a planar development of what is actually, preferably, an integral, one-piece (unitary), annular, cellular connector body 100. In particular, the left and right edges of the structure shown in FIG. 8 are actually, preferably, joined to and integral with one another. Thus, the actual structure of connector body 100 is as shown in FIGS. 7, 7A, 9, and 10, although FIG. 8 is useful to more clearly reveal certain details of various features of connector body 100. A central longitudinal axis 110 about which connector body 100 is annular is shown in FIGS. 9 and 10.

A particularly preferred material for connector body 100 is nitinol. Other examples of suitable materials include tantalum, tungsten, stainless steel, platinum, silicone, and polyurethane. Connector body 100 may be advantageously produced by starting with a single, unitary tube, such as a hypotube, and removing selected material until only the structure shown in FIGS. 9 and 10 remains. For example, laser cutting may be used to remove material from the starting tube in order to produce connector body 100. After removing the material to form the structure shown in FIG. 8, the machined tube may be placed in a mold and heat-shaped into approximately the geometry that connector body 100 will assume after deployment. For example, connector body 100 may be heat-shaped into the geometry shown in FIGS. 9 and 10. The shape of connector body 100 is retained after removing connector body 100 from the mold due to the properties of nitinol.

Connector body 100 may be described as including annularly spaced cell portions 112. Cell portions 112 may also be referred to herein as "inside aortic fingers." According to one embodiment, connector body 100 includes eight repeating cell portions 112. Connector body 100 may have fewer or more than eight of cell portions 112, depending on the axial length and perimeter of the tube used to manufacture connector body 100 and the desired ostium size of the resulting anastomosis. Alternatively, the structure of connector body 100 may have different configurations of cells and geometries.

Each cell 112 includes a pair of annularly spaced members 120. Each cell 112 typically also includes a pair of annularly spaced members 122. The proximal end of each member 122 is connected to the distal ends of adjacent members 120 of adjacent cells 112, and the distal ends of members 122 are connected to the proximal portion of an annular element 124. Annular element 124 defines the distal portion 114 of connector body 100, whereas annularly spaced members 122 define the medial portion 116 of connector body 100. Members 122 of annularly adjacent cell portions 112 may typically be separated by a distance 113 with a length in a range from about 0.065 inches to about 0.100 inches. (It should be noted that distance 113 includes the width of members 120.) A typical annularly spaced member 122 may have a length 115 in a range from about 0.060 inches to about 0.080 inches. However, the dimensions of annularly spaced members 122 may be altered according to the diameter or cross-sectional area of the graft conduit to be used in the anastomosis, for example.

The proximal ends of annularly spaced members 120 of each cell 112 are typically connected to one another at an annularly extending member 126, which is preferably curved proximally. A pair of members 120 and a member 126 define the proximal portion 118 of each cell portion 112. In each cell 112, the most proximal point of member 126 and the most distal point of annular element 124 distal thereto may typically be separated by a distance 117 with a length in a range from about 0.225 inches to about 0.250 inches. (It should be noted that the length of distance 117 includes the width of member 126 and the width of annular element 124.)

As shown in this example, connector body 100 preferably has a fixed cross-sectional area. Specifically, annular element 124 of distal portion 114 is an annular structure having a fixed cross-section, an outer surface 123, an inner surface 121, and an opening 125 defined therein, which may be round, oval, or any other substantially smooth shape. In another preferred embodiment, connector body 100 may be annularly expandable or enlargeable, whereby opening 125 may be fixedly held by ring 200 in connector assembly 500, as will be described in more detail below.

Figure 31:
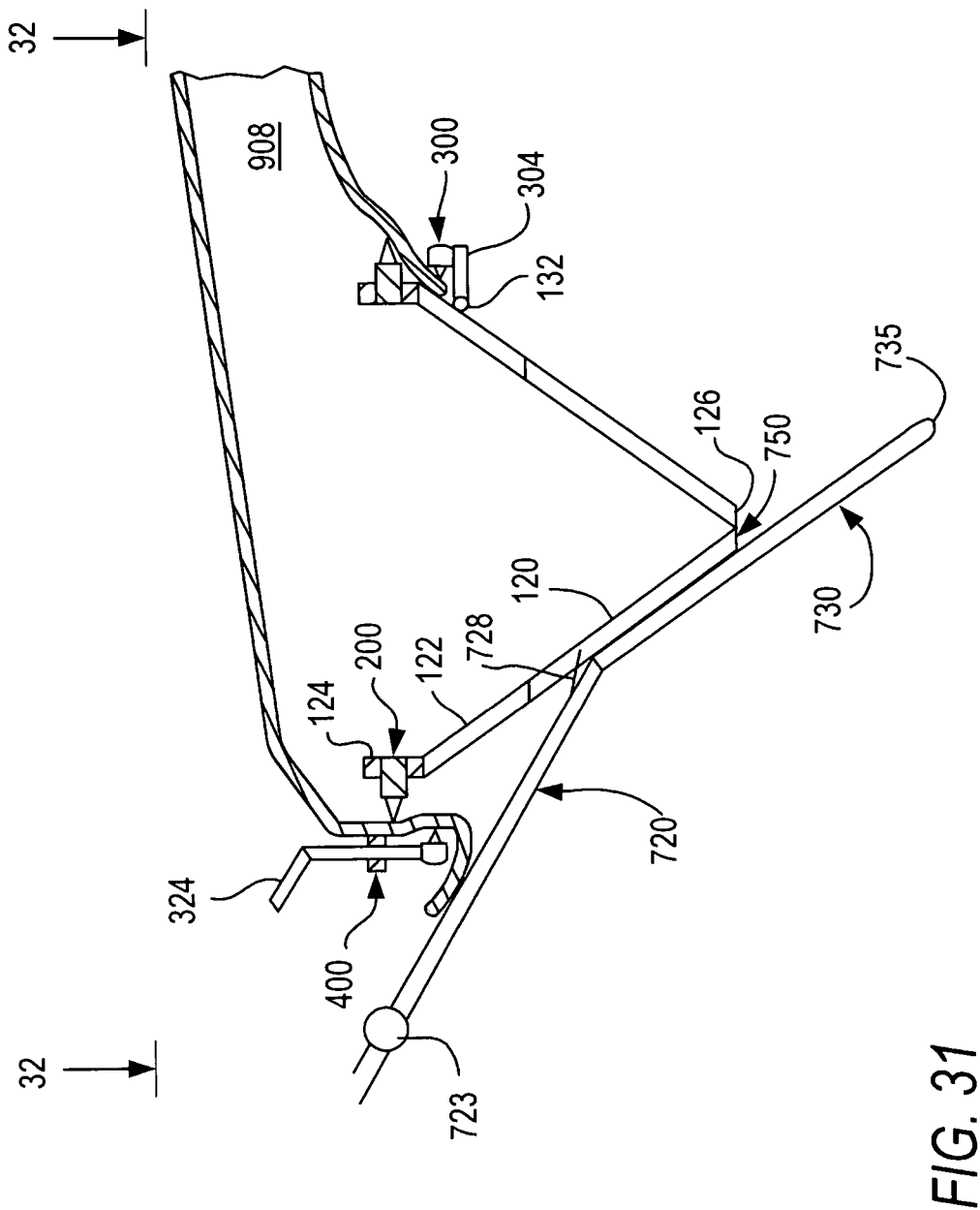
FIG. 31 is a simplified sectional view, similar to FIGS. 27, 28, and 30, of the connector assembly of FIGS. 7, 7A, 14-19, and 27-30, in the closed position of FIGS. 17, 18, and 28-30, illustrated with the graft conduit of FIGS. 25-30 and with the apparatus of FIGS. 19-24, 27, 28, and 30, in a yet even later stage of a procedure, in accordance with the invention.
Figure 32:
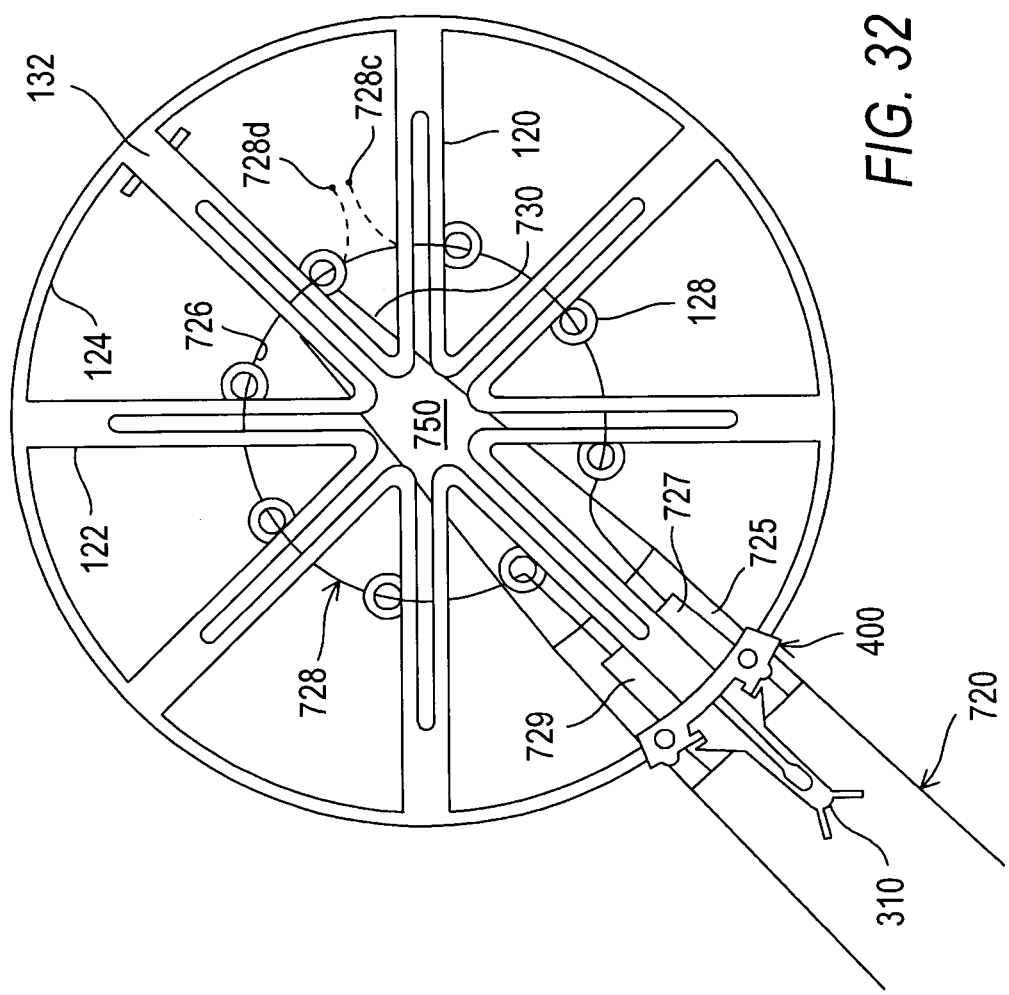
FIG. 32 is a top elevational view of the connector assembly of FIGS. 7, 7A, 14-19, and 27-31, in the closed position of FIGS. 17, 18, and 28-31, illustrated with the apparatus of FIGS. 19-24, 27, 28, 30, and 31 in the yet even later stage of the procedure of FIG. 31, taken from line 32-32 of FIG. 31, but with a portion of the connector assembly and the graft conduit omitted, in accordance with the invention.

As shown in FIGS. 9 and 10, inside aortic fingers 112 may expand radially out from distal portion 114. As described above, fingers 112 may expand to the configuration created by heat-shaping connector body 100. The expansion of fingers 112 is preferably elastic. One adjacent member 120 of each finger 112 may be provided with an aortic eyelet 128 for interaction with an aortic delivery tool such that proximal portion 118 may be configured to pass through an aperture in the aorta, as described in more detail below (see, e.g., FIGS. 31-33). (It should be noted that fingers 112 are not shown in their expanded configuration in FIGS. 7 and 7A for clarity sake.)

A plurality of receiving slots 130 may be provided along annular element 124 for receiving inside-the-graft retaining ring 200, as described in more detail below. Moreover, at a first annularly spaced member 122 there is provided a hinge joint 132 for interaction with outside-the-graft retaining band 300, as described in more detail below. Connector body 100 also typically requires other processing appropriate for an implantable device such as, for example, polishing, passivation, cleaning, and sterilizing.

Figure 11:
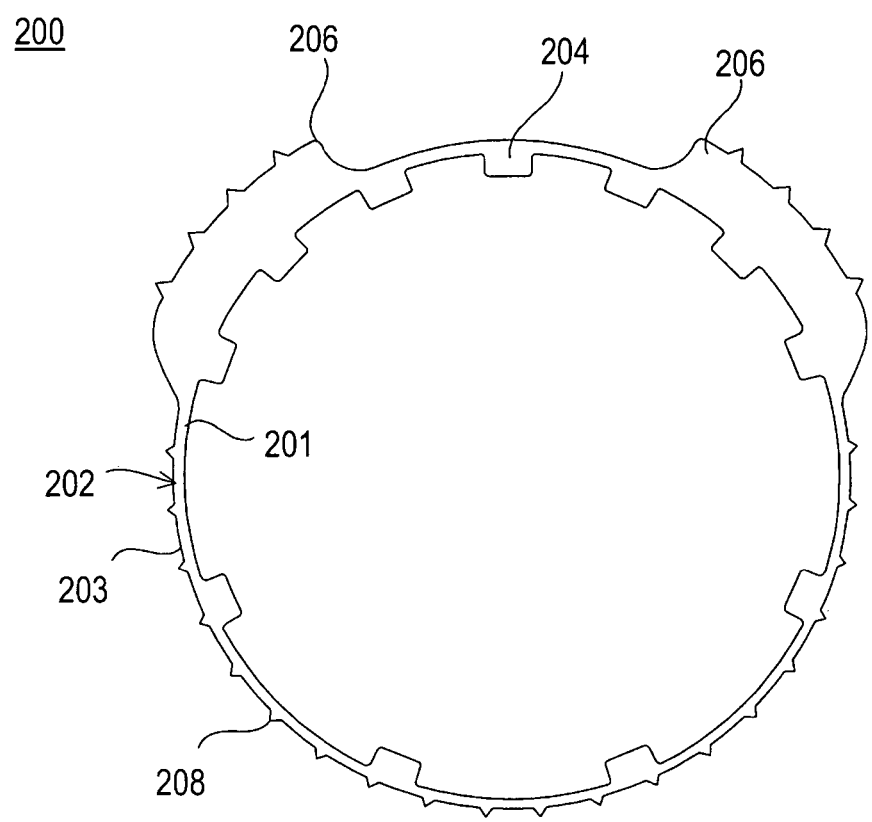
FIG. 11 is a top elevational view of an inside-the-graft retaining ring in accordance with the invention.

FIG. 11 shows in isolation substantially annular inside-the-graft retaining element or ring 200, which may be fixed or part of connector body 100 in connector assembly 500 of FIGS. 7 and 7A, although FIG. 11 is useful to more clearly reveal certain details of various features of ring 200. Like connector body 100, a particularly preferred material for ring 200 is nitinol. Other examples of suitable materials include tantalum, tungsten, stainless steel, platinum, silicone, and polyurethane. Ring 200 may be advantageously produced along with connector body 100 and connected or fixed thereto, such that the two components may be assembled and provided by the manufacturer to the physician as a single-piece device.

Inside-the-graft retaining ring 200 may generally be described as including an annular element 202 with an inner surface 201 sized such that it may substantially match the shape of annular element 124 of connector body 100 in assembly 500 of FIGS. 7 and 7A. Tabs 204 are provided around inner surface 201 of element 202 and project inwardly in substantially the same plane as ring 200. Tabs 204 are appropriately spaced around inner surface 201 such that each tab 204 may pass through a respective slot 130 in annular element 124 of connector body 100 when ring 200 is positioned thereabout, as shown in FIGS. 7 and 7A. Slots 130 in annular element 124 and tabs 204 of annular element 202 interact to join the outer surface 123 of connector body 100 and the inner surface 201 of ring 200 in connector assembly 500.

Ring 200 may also be described as including at least one flange projecting outwardly from element 202 in substantially the same plane as tabs 204. According to one embodiment, ring 200 includes two spaced flanges 206 projecting from the portion of element 202 spaced substantially diametrically opposite the portion of element 202 which interacts with annular element 124 just distal of hinge 132 of connector body 100, as shown in FIGS. 7 and 7A. Ring 200 may have fewer or more than two flanges 206, depending on the size and shape of annular element 124 of connector body 100, for example. Alternatively, the structure of connector body 100 may have different configurations of cells and geometries. Furthermore, ring 200 may also include one or more inside-the-graft retention features or teeth 208 projecting outwardly from outer surface 203 of ring 200 about element 202 and flanges 206.

Figure 12:
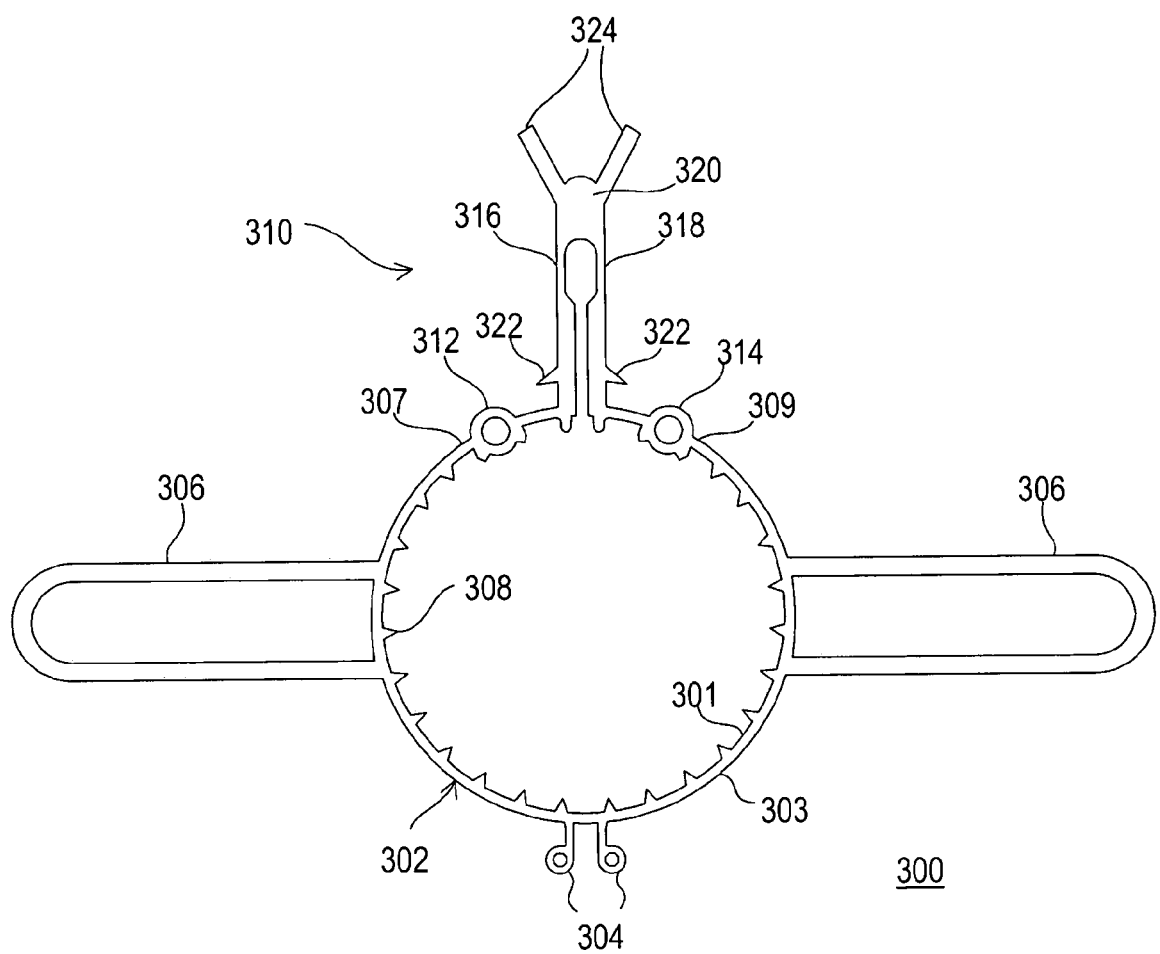
FIG. 12 is a top elevational view of an outside-the-graft retaining band in accordance with the invention.

FIG. 12 shows in isolation substantially annular outside-the-graft retaining element or band 300, which may be hingedly or pivotally coupled to connector body 100 in connector assembly 500 of FIGS. 7 and 7A, although FIG. 12 is useful to more clearly reveal certain details of various features of band 300. Like connector body 100 and ring 200, a particularly preferred material for band 300 is nitinol. Other examples of suitable materials include tantalum, tungsten, stainless steel, platinum, silicone, and polyurethane. Band 300 may be advantageously produced along with connector body 100 and ring 200 and connected thereto, such that the components may be assembled and provided by the manufacturer to the physician as a single-piece device.

Outside-the-graft retaining band 300 may generally be described as including a substantially annular element 302 with an inner surface 301 whose size and shape may match that of outer surface 203 of annular element 202 of inside-the-graft retaining ring 200. Hinge eyelets 304 are provided at a portion of outer surface 303 of element 302. Hinge eyelets 304 are appropriately spaced around outer surface 303 such that they interact with hinge joint 132 of connector body 100 when they are heat treated or bent out of the plane of element 302 towards each other and when band 300 is coupled to connector body 100, as shown in FIGS. 7 and 7A. Hinge joint 132 of connector body 100 and hinge eyelets 304 of band 300 interact such that band 300 may turn or pivot on connector body 100 to pass from a first "open" position, as shown in FIGS. 7 and 7A, beyond ring 200, to a second "closed" position thereunder, as described in more detail below (see, e.g., FIGS. 14-18). Band 300 may also include one or more outside-the-graft retention features or teeth 308 projecting inwardly from inner surface 301 of band 300 about element 302. It is to be understood that inside-the-graft retention features 208 and outside-the-graft retention features 308 may be of variable frequency about annular elements 202 and 302, respectively, and may be of variable lengths and shapes, such as "fanged" or "barbed," for example.

Figure 35:
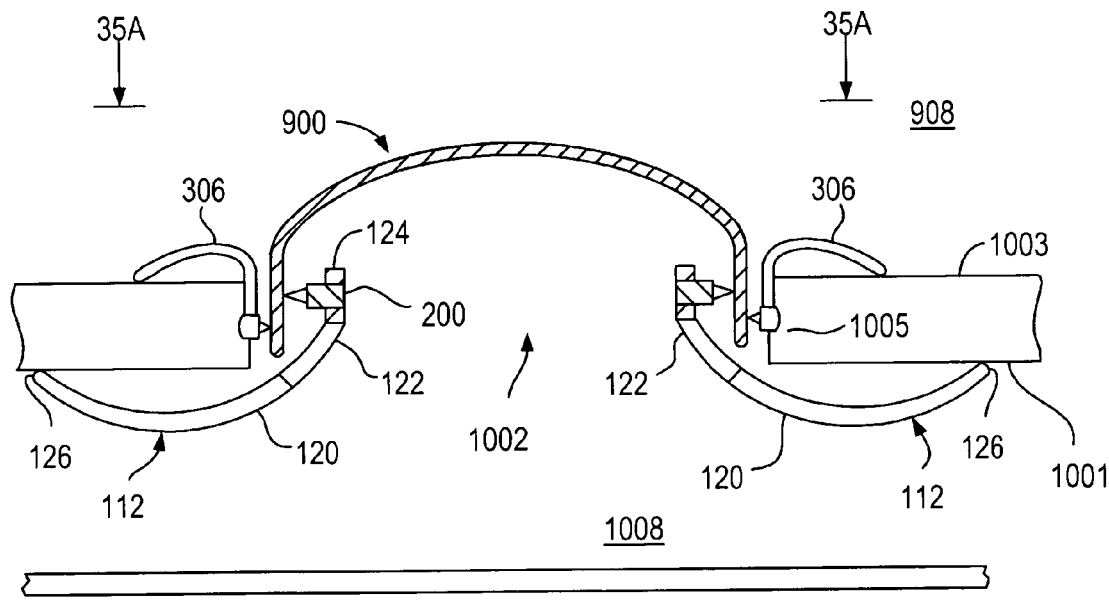
FIG. 35 is a simplified sectional view, similar to FIGS. 27, 28, 30, 31, 33, and 34, of the connector assembly of FIGS. 7, 7A, 14-19, and 27-34, in the closed position of FIGS. 17, 18, and 28-34, illustrated with the graft conduit of FIGS. 25-31, 33, and 34, in the yet still even later stage of the procedure of FIG. 34, and with the body conduit of FIGS. 33 and 34, taken from line 34-34 of FIG. 33, in accordance with the invention.

Band 300 may also be described as including one or more outside aortic fingers 306 projecting outwardly from element 302 in substantially the same plane as element 302 and may be bent or heat treated to curve out of the plane to engage the exterior wall of the aorta when the anastomosis is completed, as described in more detail below (see, e.g., FIG. 35). According to one embodiment, band 300 includes two diametrically spaced outside aortic fingers 306 projecting from element 302 at points equally removed from hinge eyelets 304. Band 300 may have fewer or more than two aortic fingers 306, depending on the size and shape of annular element 124 of connector body 100, for example.

Expansion portion 310 is included as an integral element of band 300. Expansion portion 310 may include first and second band eyelets 312 and 314 that interrupt substantially annular element 302 at ends 307 and 309, respectively. In a preferred embodiment, ends 307 and 309 may generally be provided by element 302 at a location equally separated from outside aortic fingers 306 and substantially diametrically opposite hinge eyelets 304, for example.

Expansion portion 310 may also include parallel first and second arms 316 and 318 projecting outwardly from element 302 at band eyelets 312 and 314, respectively, and joining together at a resilient joint 320. One or more sets of notches 322 may be provided along the length of arms 316 and 318 such that collar 400 may be retained thereabove or therebelow when collar 400 is positioned about expansion portion 310 in connector assembly 500, as shown in FIGS. 7 and 7A, and as described in more detail below. Furthermore, expansion portion 310 may also include a cap element, such as tip element 324, coupled to resilient joint 320 for retaining collar 400 about expansion portion 310. In a preferred embodiment, tip element 324 and first and second arms 316 and 318 may be bent or heat treated to curve out of the plane of annular element 302 for engaging the exterior wall of the aorta when the anastomosis is completed, as described in more detail below (see, e.g., FIG. 34).

Figure 13:
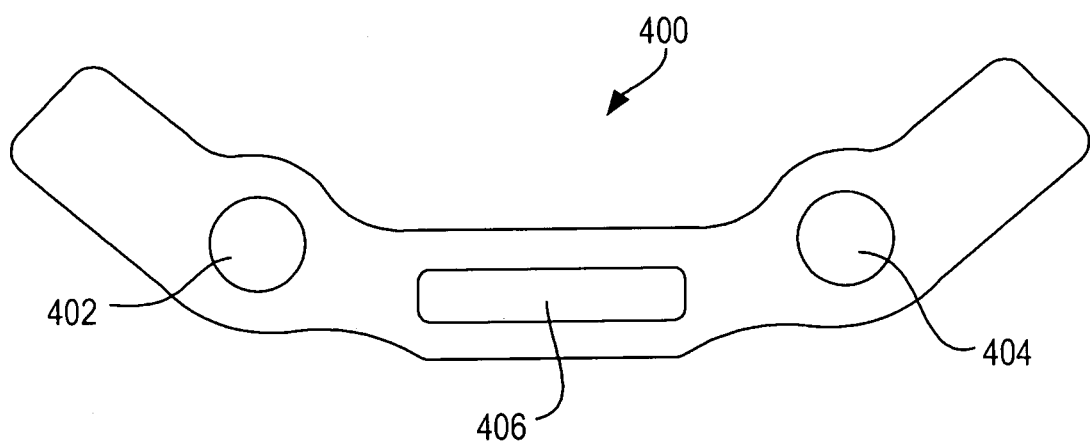
FIG. 13 is a top elevational view of a collar in accordance with the invention.

FIG. 13 shows in isolation locking or sliding collar 400, which may be positioned about arms 316 and 318 of expansion portion 310 of band 300 in connector assembly 500 of FIGS. 7 and 7A, although FIG. 13 is useful to more clearly reveal certain details of various features of collar 400. Like connector body 100, ring 200, and band 300, a particularly preferred material for collar 400 is nitinol. Other examples of suitable materials include tantalum, tungsten, stainless steel, platinum, silicone, and polyurethane. Collar 400 may be advantageously produced along with band 300, ring 200, and connector body 100, and attached thereto, such that the components may be assembled and provided by the manufacturer to the physician as a single-piece device.

A preferred embodiment of locking, snapping, or sliding collar 400 may generally be described as including a band slot 406 sized such that arms 316 and 318 of band 300 may pass therethrough in assembly 500 of FIGS. 7 and 7A. First and second collar eyelets 402 and 404 may also be provided through collar 400, generally flanking slot 406. Collar eyelets 402 and 404 are appropriately spaced such that they may align with band eyelets 312 and 314, respectively, when arms 316 and 318 are passed through slot 406 of collar 400, as described below in more detail (see, e.g., FIGS. 16 and 17).

As described above, band 300 may be hingedly coupled to hinge joint 132 at medial portion 116 of connector body 100 such that element 302 may pivot on connector body 100 to pass from a first "open" position, beyond annular element 202 of ring 200 coupled to distal portion 114 of connector body 100, to a second "closed" position proximal thereto. Moreover, in a preferred embodiment, inner surface 301 of element 302 is of substantially the same size and shape as outer surface 203 of element 202. Therefore, expansion portion 310 and collar 400 must manipulate element 302 such that inner surface 301 of element 302 may pass from an open position (see, e.g., FIGS. 7 and 7A), beyond outer surface 203 and flanges 206 of element 202, to a closed position therebelow.

Figure 14:
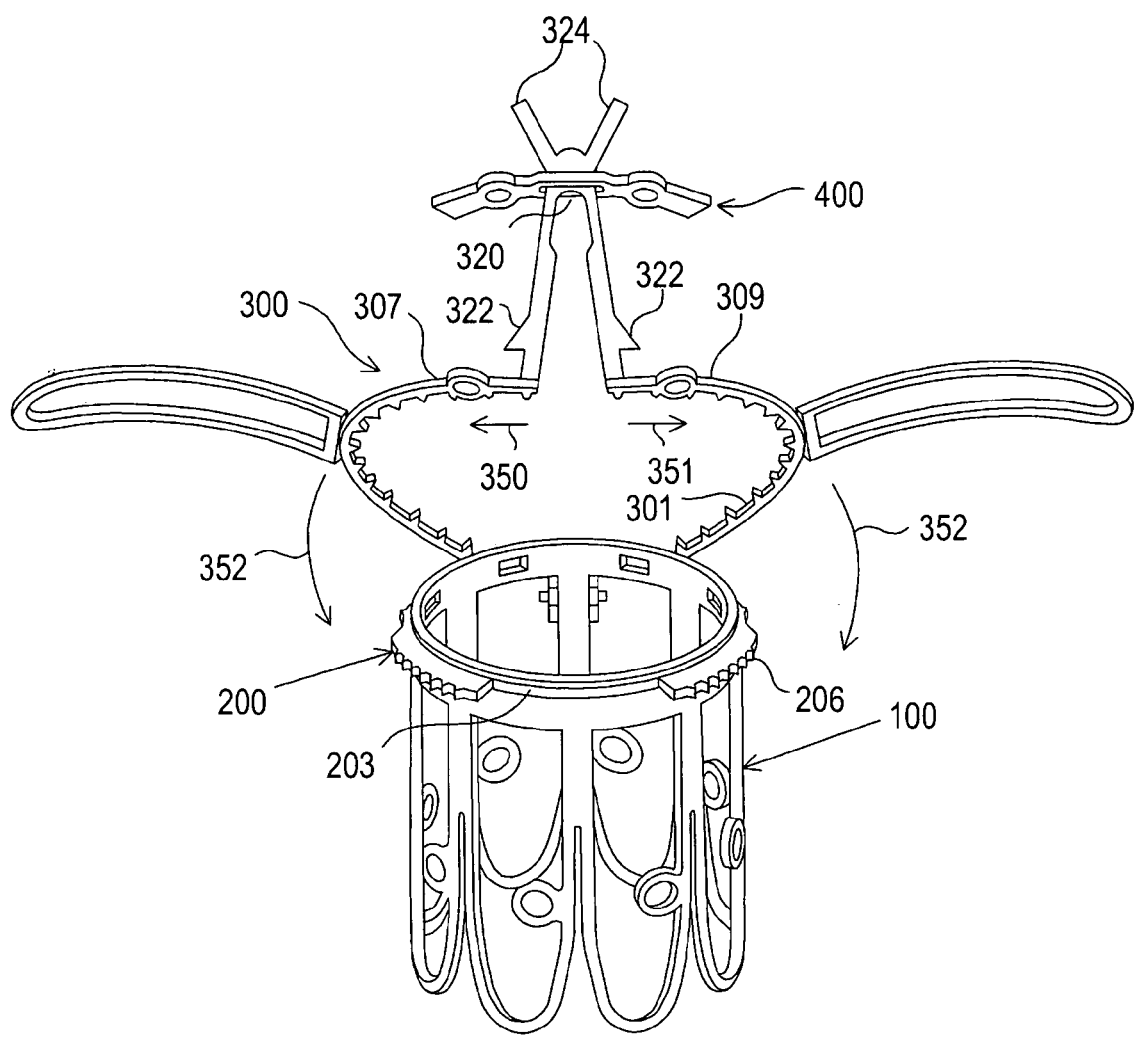
FIG. 14 is a front elevational view of the connector assembly of FIGS. 7 and 7A, in an intermediate position, in accordance with the invention.

As shown in FIG. 14, when in its open position, ends 307 and 309 of substantially annular element 302 may first be further separated from one another (e.g., by a physician's tool) about resilient joint 320 in the directions of arrows 350 and 351, respectively, thereby increasing the size and shape of the opening defined by inner surface 301. Collar 400 is preferably retained about expansion member 310 between tip element 324 and notches 322, but above joint 320, such that collar 400 does not limit the distance by which ends 307 and 309 may be separated about joint 320. Once the opening defined by inner surface 301 is increased to a suitable size and shape, element 302 may be passed in the direction of arrows 352 beyond outer surface 203 and flanges 206 of element 202.

Figure 15:
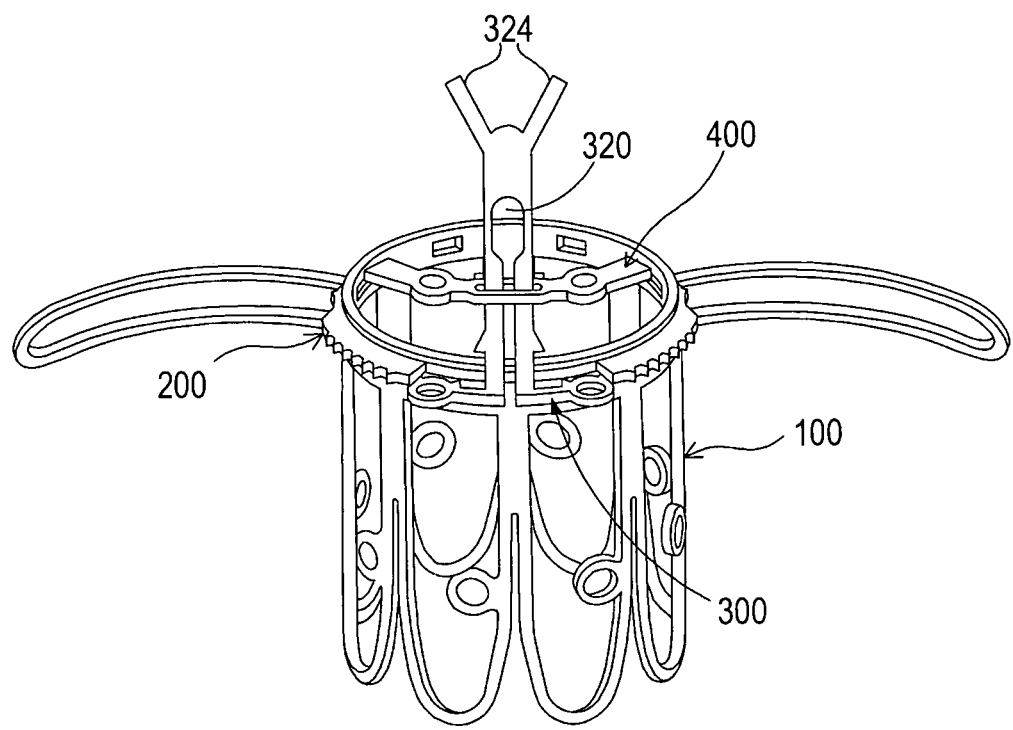
FIG. 15 is a front elevational view of the connector assembly of FIGS. 7, 7A, and 14, in another intermediate position, in accordance with the invention.
Figure 18:
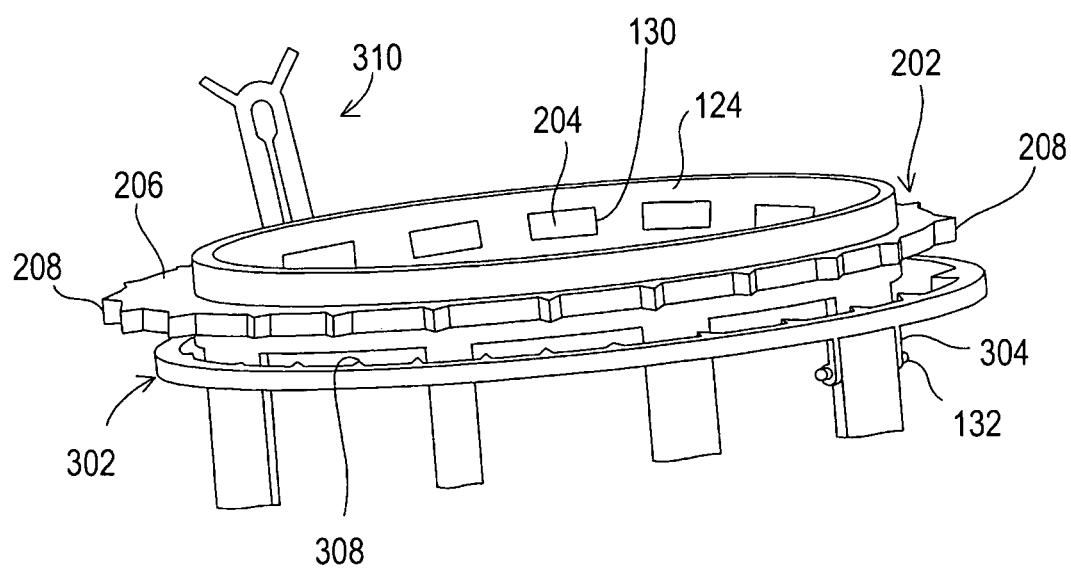
FIG. 18 is a rear elevational view of the connector assembly of FIGS. 7, 7A, and 14-17, in the closed position of FIG. 17, in accordance with the invention.

As shown in FIGS. 15 and 16, once element 302 is passed proximally beyond outer surface 203 and flanges 206 of element 202, ends 307 and 309 may be allowed to move back towards one another about joint 320, such that inner surface 301 contracts to its original size and shape about connector body 100 proximal to ring 200.

Finally, in a preferred embodiment, ends 371 and 373 of a suture line 375 passed through aligned eyelets 312 and 402 and also through aligned eyelets 314 and 404, as shown in FIGS. 16 and 17, may be pulled in the direction of arrow 376 such that collar 400 is also pulled in the direction of arrow 376 proximally over notches 322. Preferably, once collar 400 is moved proximally over notches 322 and snapped into place, expansion portion 310 is not only configured to retain collar 400 between notches 322 and flanges 206 of ring 200, but is also configured to retain flanges 206 between collar 400 and annular element 302, as shown in FIG. 17, thereby holding band 300 in its closed position along with hinge 132/304 (also see, e.g., FIG. 18, wherein outside aortic fingers 306 are not shown for sake of clarity). Suture line 375 may then either be left alone or removed from connector assembly 500.

In another embodiment, collar 400 may simply be pushed proximally over notches 322, thereby obviating not only suture line 375 but also eyelets 312, 314, 402, and 404. In yet another embodiment described in more detail below with respect to FIGS. 44-46, an outside-the-graft retaining band may be substantially annular and provided with one or more expansion portions such that its inner surface may expand stretch to be larger than outer surface 203 and flanges 206 of element 202. In this embodiment, the outside-the-graft retaining band may be coupled to body connector 100 at the time of its expansion, rather than being hinged thereto, thereby obviating not only collar 400, but also hinge eyelets 304. In yet still another embodiment, element 302 of band 300 may be completely annular but resilient such that its inner surface may elastically stretch to be larger than outer surface 203 and flanges 206 of element 202. In this embodiment, element 302 may simply be stretched to pass beyond element 202 and then released to contract below ring 200 about annular element 124 of body connector 100, thereby obviating not only hinge eyelets 304, but also collar 400 and expansion portion 310.

Figure 19:
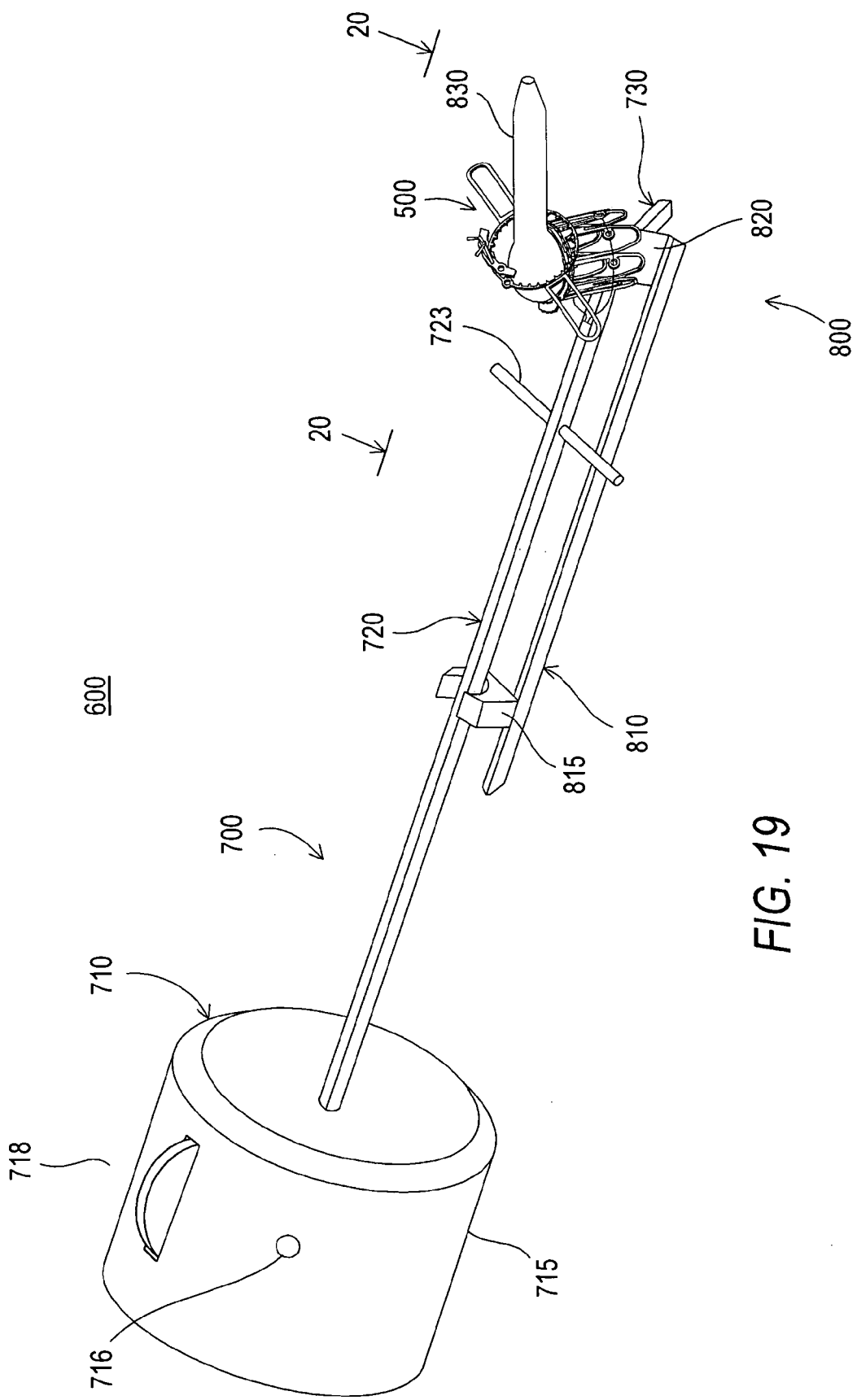
FIG. 19 is a perspective view of illustrative apparatus for use in loading and delivering connector assembly, illustrated with the connector assembly of FIGS. 7, 7A, and 14-18, in the open position of FIGS. 7 and 7A, in a first stage of a procedure, in accordance with the invention.
Figure 20:
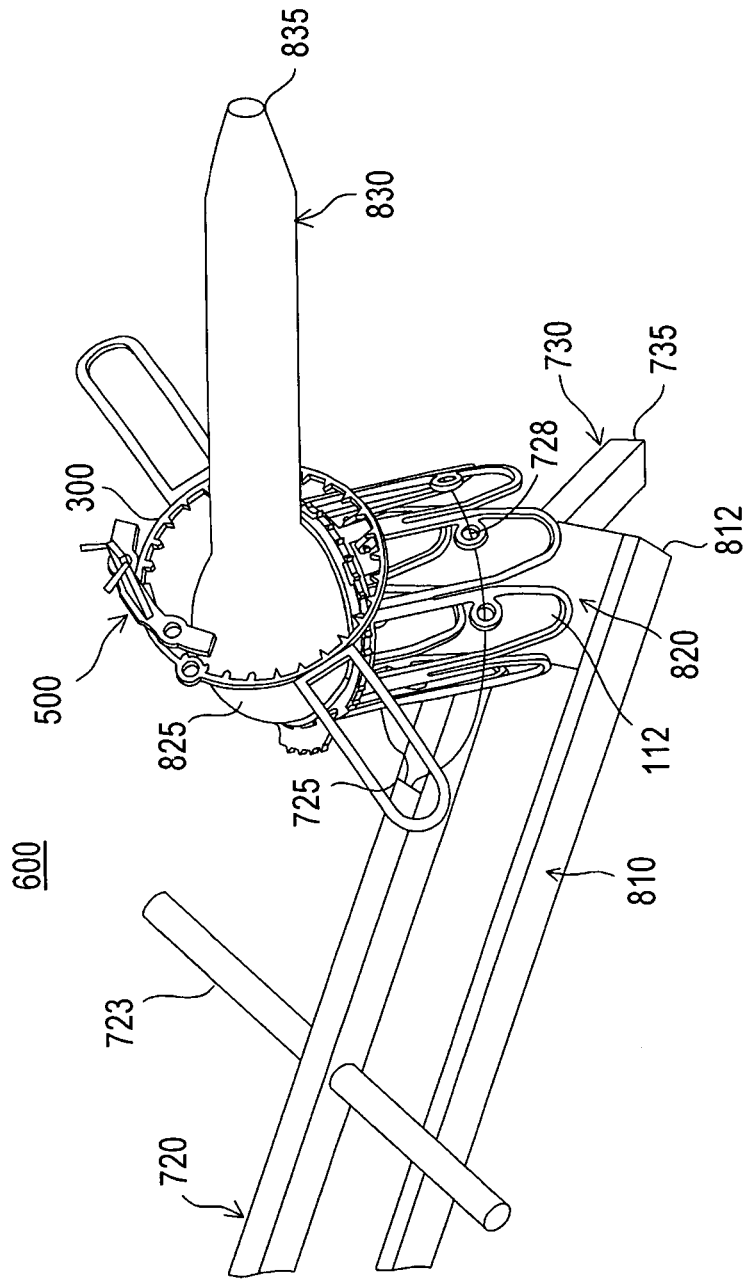
FIG. 20 is a perspective view of the apparatus of FIG. 19 and the connector assembly of FIGS. 7, 7A, and 14-19, taken from line 20-20 of FIG. 19.

A typical use of connector assembly 500 is to provide an anastomosis between an end of a graft conduit and an aperture in a side wall of the aorta in a coronary bypass procedure, as described above. An illustrative apparatus for deploying connector assembly 500 such that it engages a tubular graft conduit and a patient's body tissue conduit (e.g., aorta) is shown in FIGS. 19-24. FIGS. 19 and 20 are an isometric view of apparatus 600 and connector assembly 500 (FIGS. 7-19) and FIGS. 21-24 show certain components of apparatus 600 in isolation to further illustrate their features.

Apparatus 600 may include aortic delivery tool 700 (portions of which are shown in isolation in FIGS. 21-23) and graft loading tool 800 (shown in isolation in FIGS. 24 and 24A) coupled thereto. Graft loading tool 800 is preferably a one-piece element, and may include a loading arm portion 810, a loading body portion 820, and a loading lead portion 830. Loading arm portion 810 may extend substantially parallel to a portion of aortic delivery tool 700 and may be releasably attached thereto by a coupling member 815 provided at a proximal end 811 of arm portion 810. Body portion 820 may extend from a distal end 812 of arm portion 810 and may pass through connector body 100 substantially along its central longitudinal axis 110 (FIGS. 9 and 10) such that a bulbous head 825 is generally positioned distally of annular element 124. The bulbous shape of head 825 is desirable to aid in defining the resulting shape of the anastomosis external to the aorta, as will be described in more detail below (see, e.g., FIG. 28). Tool 800 may also be described as including one or more resilient tissue holding elements 823 extending from distal end 812 of arm portion 810 about body portion 820 towards head 825. Elements 823 may be bent or heat treated to resiliently contact the exterior of body portion 820 generally below head 825 to releasably hold the exterior wall of the graft conduit against body portion 820 as it is loaded on connector assembly 500, as described in more detail below and shown in FIG. 27A, for example. It is to be noted that elements 823 are not illustrated in FIGS. 19 and 20 for the sake of clarity. According to one embodiment, tool 800 includes two diametrically spaced tissue holding elements 823. Tool 800 may have fewer or more than two tissue holding element 823, depending on the size and shape of annular element 124 of connector body 100, for example. A lead portion 830 may preferably extend from head 825 of body portion 820 through band 300. Lead portion 830 may include a tip 835 at its distal end that is preferably tapered to enable the end of a graft conduit to slide onto lead portion 830 without damage, with minimal force being required, and with no catching or snagging on the walls of the conduit, as will be described in more detail below (see, e.g., FIGS. 27 and 28).

Aortic delivery tool 700 may generally be described as including a physician control portion 710, a delivery arm portion 720, and a delivery lead portion 730. Delivery arm portion 720 may extend distally from physician control portion 710 and substantially parallel to loading arm portion 810 of graft loading tool 800. An opening 725 at distal end 722 of arm portion 720 exposes the distal ends of lumens 727 and 729, which may extend proximally through arm portion 720 to physician control portion 710. Lead portion 730 may extend away from distal end 722 of arm portion 720. Lead portion 730 may include a tip 735 at its distal end that is preferably tapered to enable its insertion into the lumen of an aorta through an aperture or incision therein with minimal damage, with minimal force being required, and with no catching or snagging on the walls of the aorta, as will be described in more detail below (see, e.g., FIGS. 33 and 34). Furthermore, a bar 723 may be provided proximal to end 722 of arm portion 720 and substantially transverse thereto, such that during insertion of tip 735 into the lumen of an aorta, bar 723 may contact the exterior of the aorta to limit the length of lead portion 730 passed therein, as will be described in more detail below (see, e.g., FIG. 33).

FIG. 20 shows the inside aortic fingers or cells 112 of connector body 100 (FIGS. 8-10) constrained around loading body portion 820 of graft loading tool 800 by an illustrative constraining device of the present invention. This may be accomplished using a constraining member, which may be fine wire less than 0.020 inches in diameter and made of nitinol, steel, nylon, polypropylene, silk, etc., in order to constrain the inside aortic fingers into a configuration that allows the connector assembly to be loaded with graft and aortic tissue. This constraint may be a noose, slip knot, quick release tie, or of various other configurations. The connector assembly itself may or may not have features that guide the path of the constraining member. The constraining member may be part of the delivery device or the connector assembly itself. The method for such constraint and release is benefitted by the reduction in friction between the constraining member and the connector assembly. Material choice and connector assembly geometry can greatly influence the functionality of the constraining member. Connector assembly geometry that allows the constraining member to have a continuous path minimizes the point contacts that cause the member to deflect from its desired path. Constraining members which pass through, or are contained or constrained by the connector assembly can be accomplished in several ways including, but not limited to, having connector assembly geometry that easily deforms in a way that facilitates a continuous radius path, having geometry that allows the constraining member to take a path with minimum deflections from the continuous radius, or having multiple constraining members which reduce the need for a multiple deflection and contact points. For constraining members which do not pass through or are not contained in the connector assembly geometry, the functional geometry components may consist of geometry which guides or positions the constraining member in the desired location to facilitate proper constraint and release of the connector assembly.

In the preferred embodiment shown in FIGS. 19-33, connector assembly 500 is constrained by a noose configuration of delivery tool 700, whose wire 728 follows a path around body portion 820 of graft loading tool 800 and through the aortic eyelet 128 of each aortic finger 112. The noose may be pulled tightly to constrain connector assembly 500 about body portion 820 of graft loading tool 800 such that inside aortic fingers 112 are not in their expanded configuration (FIGS. 9 and 10) but rather such that inside aortic fingers 112 are held in a constrained position proximally removed from element 124 and ring 200. This further exposes the distal portion of the connector assembly geometry that is to constrain and hold the tissue of the graft conduit.

Figure 21:
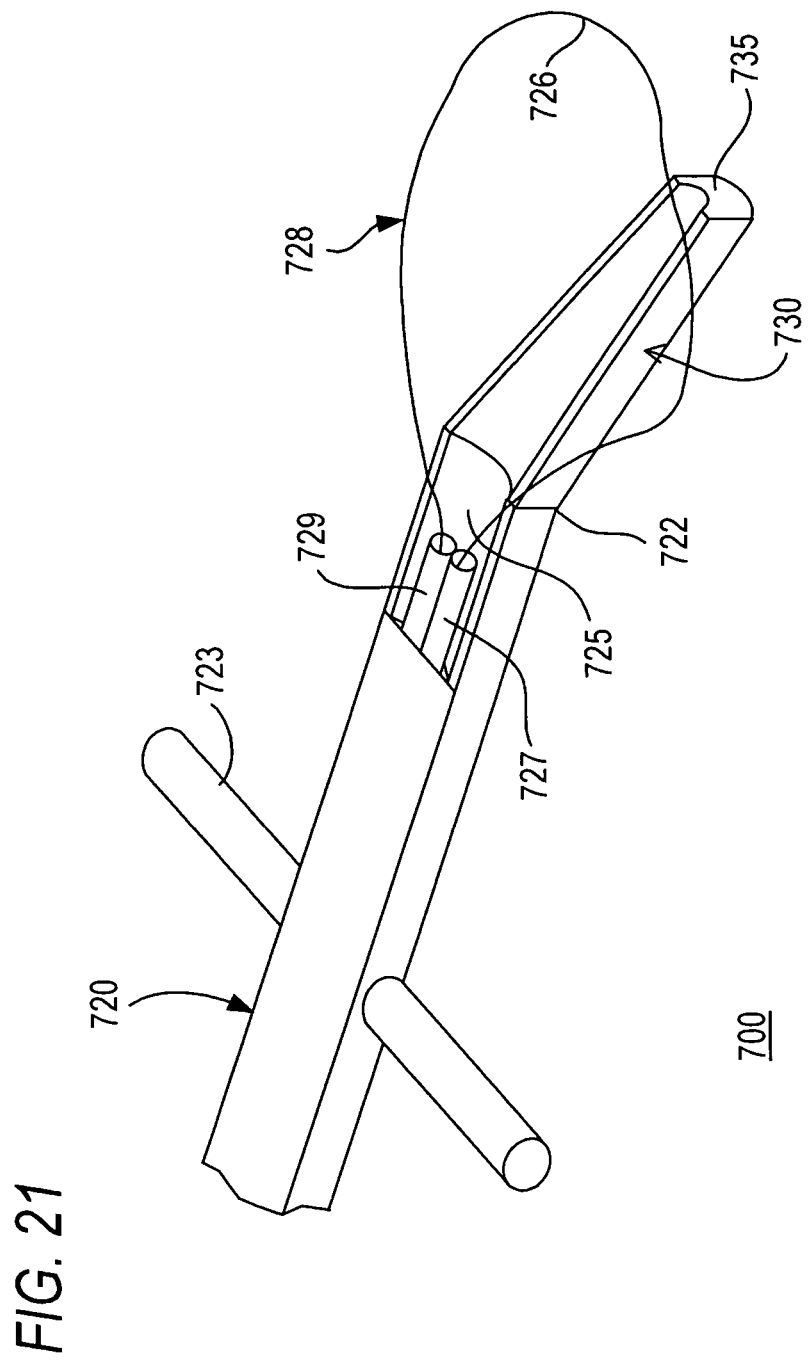
FIG. 21 is a perspective view, similar to FIG. 20, of a first portion of a first component of the apparatus of FIGS. 19 and 20.
Figures 22, 23:
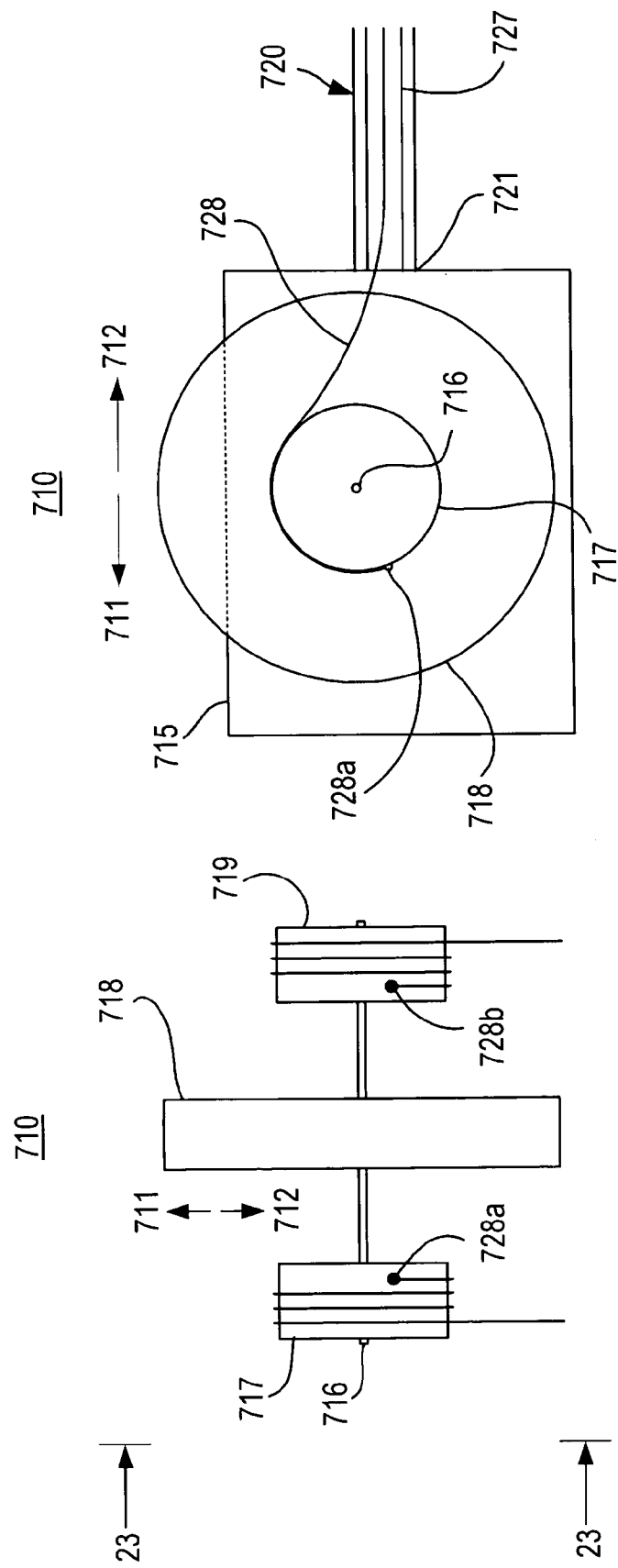
FIG. 22 is a top elevational view of a second portion of the first component of the apparatus of FIGS. 19-21.
FIG. 23 is a side elevational view of the second portion of the first component of the apparatus of FIGS. 19-22, taken from line 23-23 of FIG. 22.

FIGS. 21-23 show the components of aortic delivery tool 800 that provide the noose. An exposed loop portion 726 of wire 728 is provided at the distal ends of lumens 727 and 729 through opening 725 at distal end 722 of arm portion 720. Loop portion 726 may follow a path around body portion 820 of graft loading tool 800 and through the aortic eyelet 128 of each aortic finger 112, as described above and shown in FIGS. 19 and 20. The remaining portion of wire 728 may pass through lumens 727 and 729, along delivery arm portion 720, and into housing 715 of physician control portion 710. Ends 728a and 728b of wire 728 each may be coupled to a respective one of spools 717 and 719 fixed to a rod 716 passing through housing 715. Rotatable disc 718 may be fixed to rod 716 such that a physician may impart rotation to spools 717 and 719 via disc 718 and rod 716. By rotating disc 718, and thereby spools 717 and 719, in the direction of arrow 711, wire 728 is wound onto both spools. Conversely, by rotating disc 718 in the direction of arrow 712, wire 728 is unwound from spools 717 and 719. Therefore, by winding wire 728 onto spools 717 and 719 through rotation of disc 718 in the direction of arrow 711, loop portion 726 may be pulled tightly to constrain connector assembly 500 about body portion 820 of graft loading tool 800, and by unwinding wire 728 from spools 717 and 719 through rotation of disc 718 in the direction of arrow 712, loop portion 726 may be loosened such that inside aortic fingers 112 are able to expand radially out towards their expanded configuration. In another embodiment, ends 728a and 728b of wire 728 may each be coupled to a single spool fixed to rod 716, for example.

Apparatus 600 may be used to load a tubular graft conduit onto connector assembly 500 for creating an aortic anastomosis. Prior to loading the graft onto connector assembly 500, an end of the graft may be prepared with a type of cut to provide an opening such that the ostium cross-sectional area of the anastomosis may be larger than that of the end of the native graft conduit. Preferably, such an opening has a cross-sectional area that is at least equal to that of opening 125 of annular element 124 of connector assembly 500 (see, e.g., FIG. 10).

Figure 26:
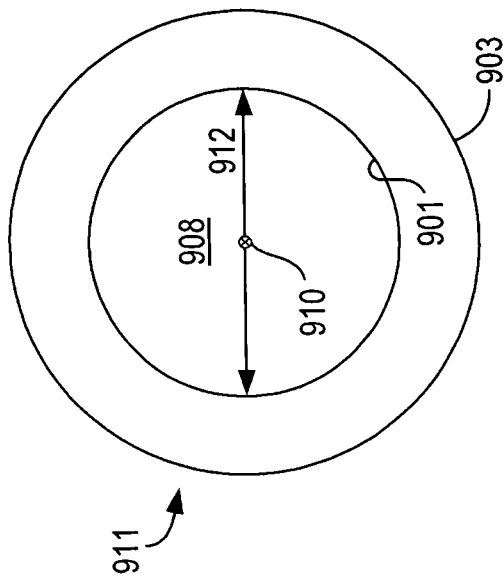
FIG. 26 is a simplified bottom sectional view of the graft conduit of FIG. 25, taken from line 26-26 of FIG. 25.
Figure 25:
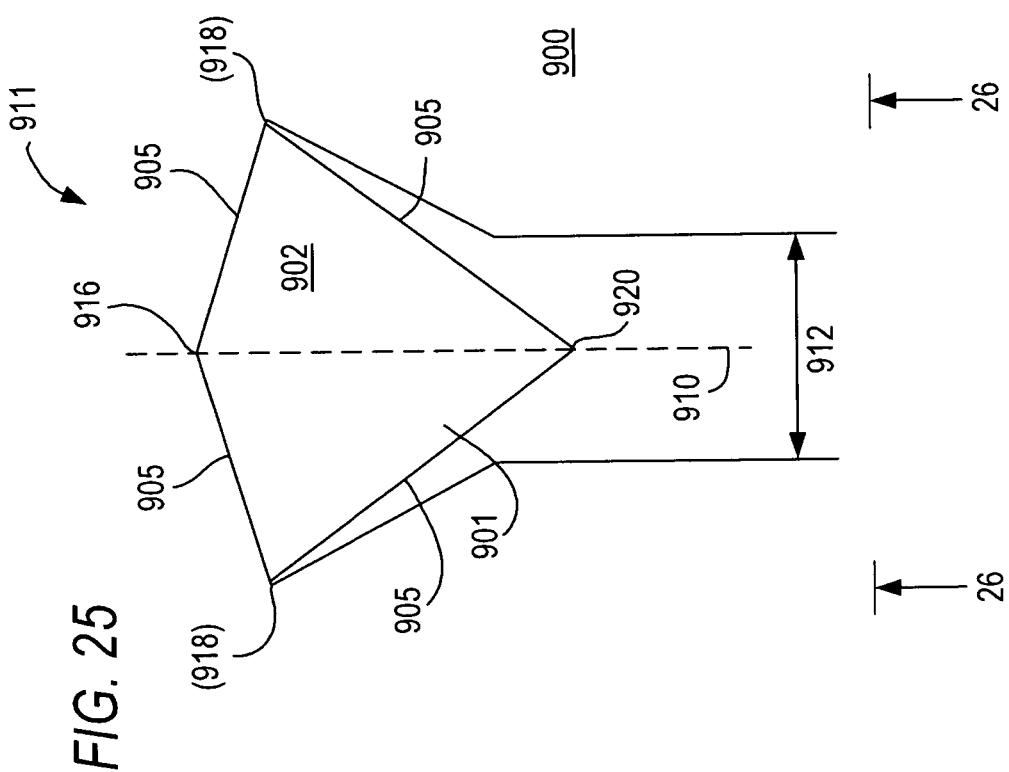
FIG. 25 is a front elevational view of a graft conduit prepared with an axial cut, fileted open, for use in a patient with the connector assembly of FIGS. 7, 7A, and 14-19, in accordance with the invention.

A graft conduit 900 is subsequently loaded onto connector assembly 500 about an opening 902 prepared at an end 911 of graft conduit 900. As shown in FIG. 26, for example, interior surface 901 of graft conduit 900 defines a lumen 908 having an inner diameter 912 for providing fluid flow therethrough substantially along central longitudinal axis 910 of graft conduit 900. Lumen 908 may generally be described as having a cross-sectional area transverse to axis 910 (and parallel to inner diameter 912) that is smaller than that of opening 902.

Graft conduit 900 may be natural body tissue (e.g., a length of the patient's saphenous vein harvested for use as a graft, a partly severed internal mammary artery, etc.), an artificial graft (e.g., as shown in Goldsteen et al. U.S. Pat. No. 5,976,178, which is hereby incorporated by reference herein in its entirety), or a combination of natural and artificial conduits (e.g., a length of natural conduit disposed substantially concentrically inside a length of artificial conduit).

Opening 902 with a cross-sectional area larger than that of lumen 908 transverse to axis 910 may be prepared at end 911 of graft conduit 900 with any of the types of cuts and methods described above with respect to FIGS. 1-6 or combinations thereof. In one example, opening 902 is made by preparing an axial cut at end 911 of graft conduit 900 with a blade. For example, a lengthwise axial incision may be made from a point 918 opposite toe point 916 at end 911 to a heel point 920, whereby the segments of tissue between points 916, 918, and 920 define periphery 905 of opening 902. The length of the axial incision may preferably be about 2-4 times that of the diameter or major axis (if oval) of annular element 124, about which graft conduit 900 is to be loaded. However, the size of the initial incision may be adjusted based on the inner diameter of graft conduit 900, the outer diameter of the connector, and amount of residual toe tissue of graft conduit 900, for example, such that the cross-sectional area of opening 902 created may be customized to match the size and shape of the ostium of the connector used in making the aortic anastomosis. Other examples of cutting methods and apparatus for preparing an opening at an end of a graft conduit are described, for example, in published Patent Cooperation Treaty ("PCT") patent application publication No. WO 01/39672, published Jun. 7, 2001, which is hereby incorporated by reference herein in its entirety.

Figure 27:
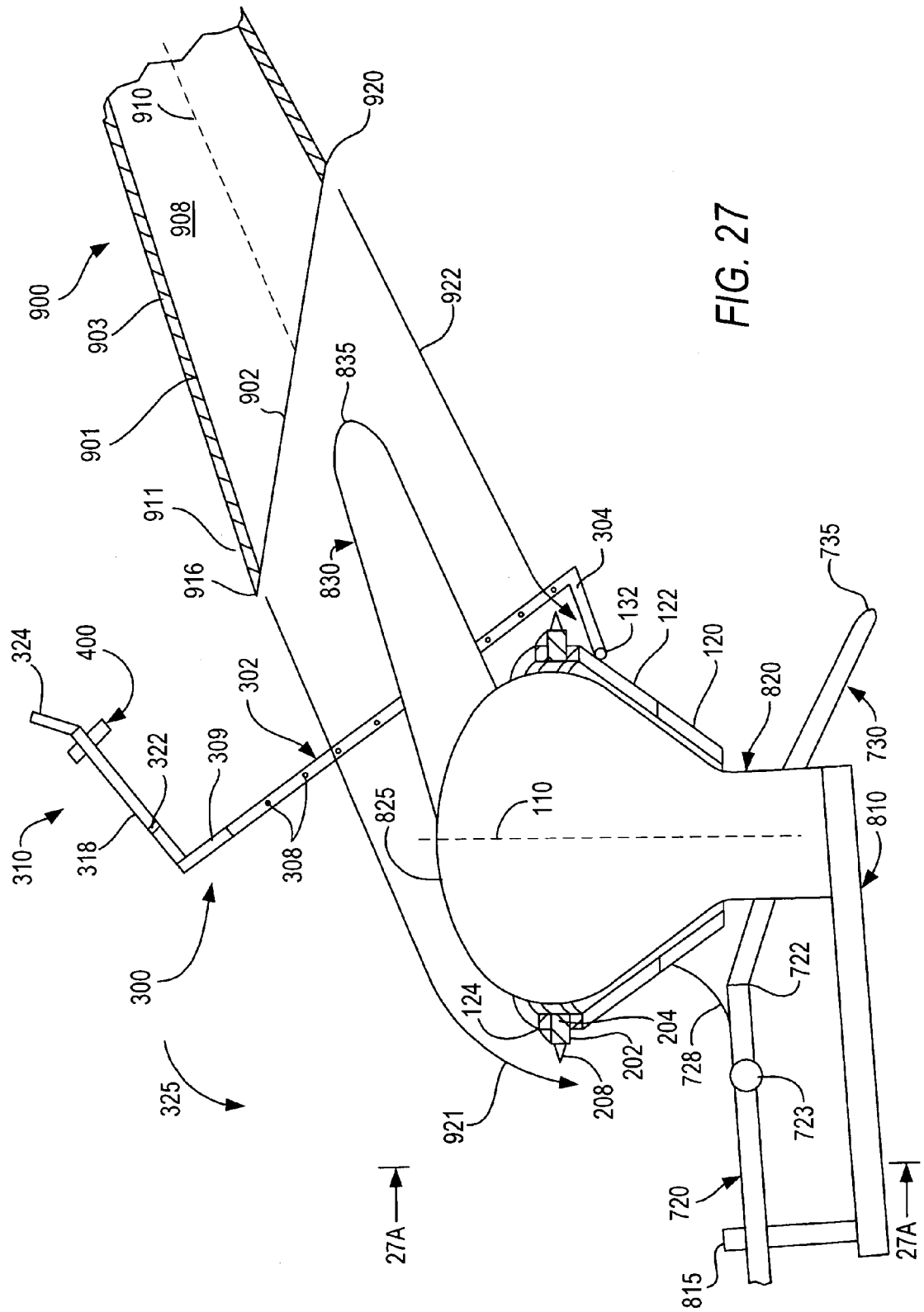
FIG. 27 is a simplified sectional view of the connector assembly of FIGS. 7, 7A, and 14-19, in the open position of FIGS. 7 and 7A, illustrated with the graft conduit of FIGS. 25 and 26 and with the apparatus of FIGS. 19-24, in the first stage of a procedure, in accordance with the invention.

For attachment, graft conduit 900 may be positioned adjacent to tip 835 of graft loading tool 800 such that opening 902 at end 911 faces connector assembly 500 and such that central longitudinal axis 910 is axially aligned with the length of lead portion 830. As illustrated in FIG. 27, toe 916 and heel 920 of opening 902 may be advanced in the direction of arrows 921 and 922, respectively, about lead portion 830 of loading tool 800, through substantially annular element 302 of outside-the-graft retaining band 300, and about inside-the-graft retention features 208 of inside-the-graft retaining ring 200, such that all points substantially about periphery 905 of opening 902 are draped over annular element 124 of connector body 100 and about inside-the-graft retention features 208. Then, tissue holding elements 823 may preferably be manipulated to press against exterior surface 903 of periphery 905, thereby holding conduit 900 about body portion 820 of tool 800 and about inside-the-graft retention features 208 of connector assembly 500, as shown in FIG. 27A, for example.

FIG. 28 shows toe 916 and heel 920 advanced such that interior surface 901 substantially adjacent periphery 905 of opening 902 envelops inside-the-graft retention features 208 of ring 200. Periphery 905 has passed proximally beyond ring 200 whereby the interior surface 901 substantially directly adjacent heel 920 may be positioned to engage the inside-the-graft retention features 208 adjacent hinge joint 132 of connector body 100. Preferably, the clearance between the periphery defined by retention features 208 and periphery 905 adjacent to heel 920 is minimal such that the remainder of periphery 905 may be substantially centered about axis 110 of connector assembly 500 and draped thereabout to ensure that each retention feature 208 of ring 200 engages some portion of interior surface 901 of graft conduit 900, as shown in FIG. 29, for example. The take-off angle of the aortic anastomosis created by graft conduit 900 may be variably increased by the physician, for example, by increasing the amount of tissue at periphery 905 adjacent to toe 916 passed beyond the retention features 208 of ring 200, generally designated as amount 913. Furthermore, it is to be understood that the take-off angle may also preferably be varied by the relative sizes of the inside diameter of the graft conduit (e.g., inside diameter 912) and the outside diameter of the inside-the-graft retaining ring (e.g., the outside diameter of annular element 203). It is also preferable that periphery 905 is draped such that interior surface 901 contacts head 825 to help define the resulting shape of the anastomosis, as shown in FIG. 28, for example.

With continued reference to FIG. 28, periphery 905 of opening 902 of graft conduit 900 is substantially fixed to connector assembly 500 about annular element 124 of connector body 100. More particularly, band 300 has pivoted on hinge joint 132 of connector body 100 in the direction of arrow 325 (FIG. 27) such that element 302 has passed from an open position about lead portion 830 (see, e.g., FIG. 27), proximally beyond ring 200, to a closed position thereunder, as described above with respect to FIGS. 14-18. As shown in FIG. 28, once band 300 has been locked in its closed position by collar 400, interior surface 901 substantially adjacent periphery 905 of opening 902 envelops inside-the-graft retention features 208 of ring 200 and exterior surface 903 substantially adjacent periphery 905 of opening 902 is engaged by outside-the-graft retention features 308 of band 300. The substantially opposite forces applied to surfaces 901 and 903 of graft conduit 900 by inside-the-graft retention features 208 and outside-the-graft retention features 308, respectively, may hold graft conduit 900 in a substantially fixed position about annular element 124 of connector assembly 500. It will be appreciated that the perimeter of the ostium created by connector assembly 500 through opening 911 in graft conduit 900 is not defined by periphery 905, but instead is limited by inner surface 121 of annular element 124, which may have a cross-sectional area larger than that of graft conduit 900.

Inside-the-graft retention features 208 of ring 200 may penetrate and pass through the side wall of graft conduit 900 from interior surface 901 to exterior surface 903 as a result of, for example, compressing the graft against the tips of features 208 with a physician's tool (e.g., the vein piercing tool described in Logan et al. U.S. Pat. No. 6,669,256, which is hereby incorporated by reference herein in its entirety), thereby forcing the free end portions of features 208 to pierce through the graft wall. Sharpened tips of the free end portions of features 208 may facilitate penetration of conduit 900, while blunt rear surfaces may resist withdrawal therefrom, like a barb. Conduit 900 may be additionally or alternatively directly sutured to connector body 100. Alternatively, conduit 900 may be secured to connector body 100 by, for example, pinching, inverting, clinching, stretching, or any other suitable manner of attaching the graft to the connector, with or without glues, clips, or any other connector elements.

Figure 30:
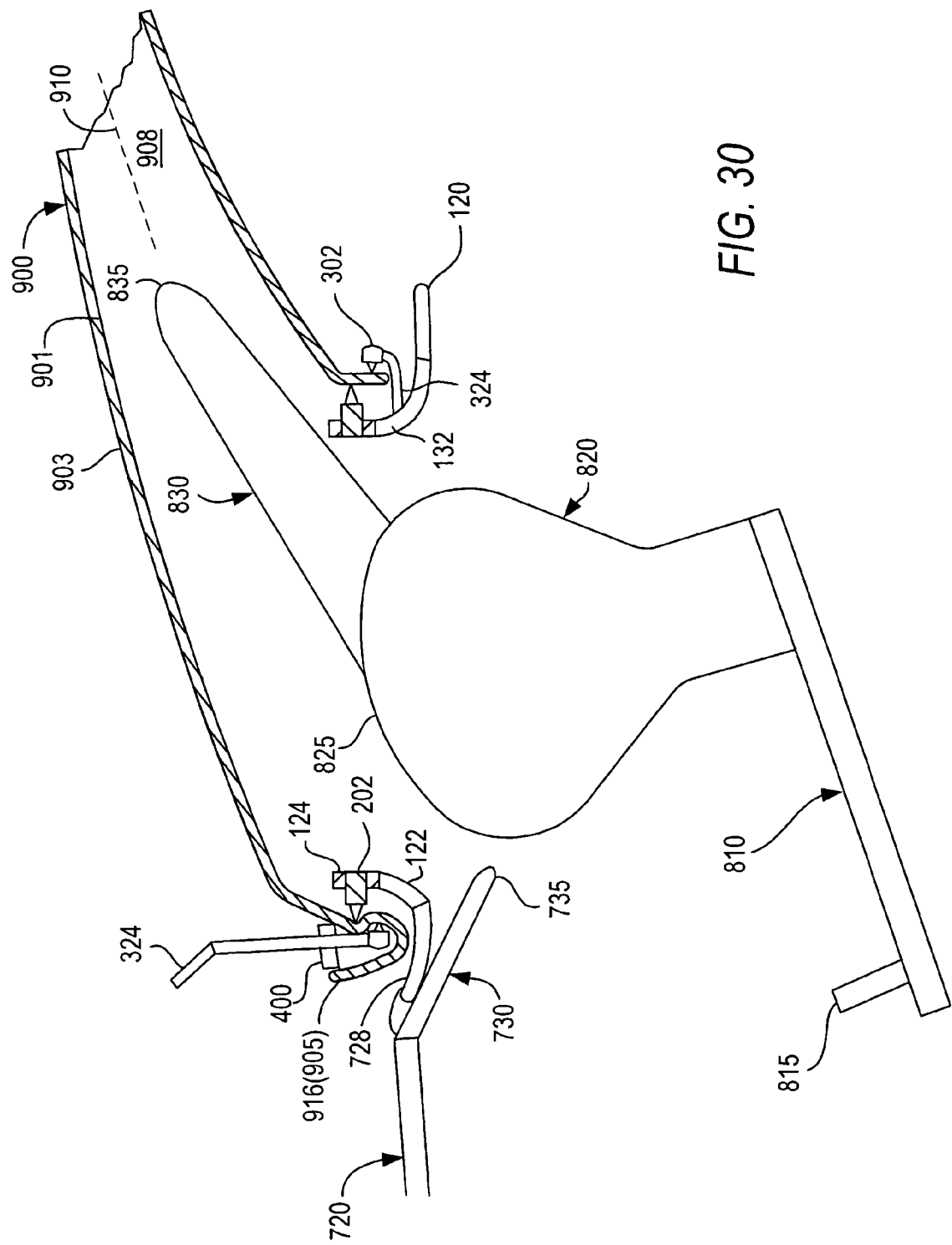
FIG. 30 is a simplified sectional view, similar to FIGS. 27 and 28, of the connector assembly of FIGS. 7, 7A, 14-19, and 27-29, in the closed position of FIGS. 17, 18, 28, and 29, illustrated with the graft conduit of FIGS. 25-29 and with the apparatus of FIGS. 19-24, 27, and 28, in an even later stage of a procedure, in accordance with the invention.

Once collar 400 has locked band 300 in its closed position such that graft conduit 900 is held about annular element 124 of connector assembly 500, loop portion 726 may be loosened by unwinding wire 728 from spools 717 and 719 through rotation of disc 718, as described above (see, e.g., FIGS. 21-23), such that inside aortic fingers 112 may expand radially out towards their expanded configuration (see, e.g., FIGS. 9 and 10). Tissue holding elements 823 may be manipulated to disengage from exterior surface 903 of conduit 900, coupling member 815 may be detached from delivery arm portion 720, and graft loading tool 800 may be removed from within graft conduit 900 and connector assembly 500, as shown in FIG. 30. The ostium may then be examined by the physician.

Next, loop portion 726 may be tightened again by winding wire 728 onto spools 717 and 719 through rotation of disc 718 as described above (see, e.g., FIGS. 21-23) to re-constrain inside aortic fingers 112 such that each annularly extending member 126 of connector body 100 substantially converges with the other annularly extending members 126 at a convergence 750. The geometry and deformability of inside aortic fingers 112, the length of members 120 and 122, position of aortic eyelets 128 therealong, and the manner in which wire 728 of loop portion 726 is threaded through the aortic eyelet 128 of each aortic finger 112 may determine whether the annularly extending member 126 of a particular finger 112 is held tightly on top of, underneath, or, as in the preferred embodiment shown, against the annularly extending member 126 of an adjacent finger 112 at convergence 750 (see, e.g., FIGS. 31 and 32). When inside aortic fingers 112 are re-constrained by aortic delivery tool 700, convergence 750 is preferably held against lead portion 730. It is to be understood that in the embodiment where inside aortic fingers 112 are re-constrained such that they overlap each other, the size and shape of proximal portion 118 of connector body 100 may be substantially reduced.

Figure 33:
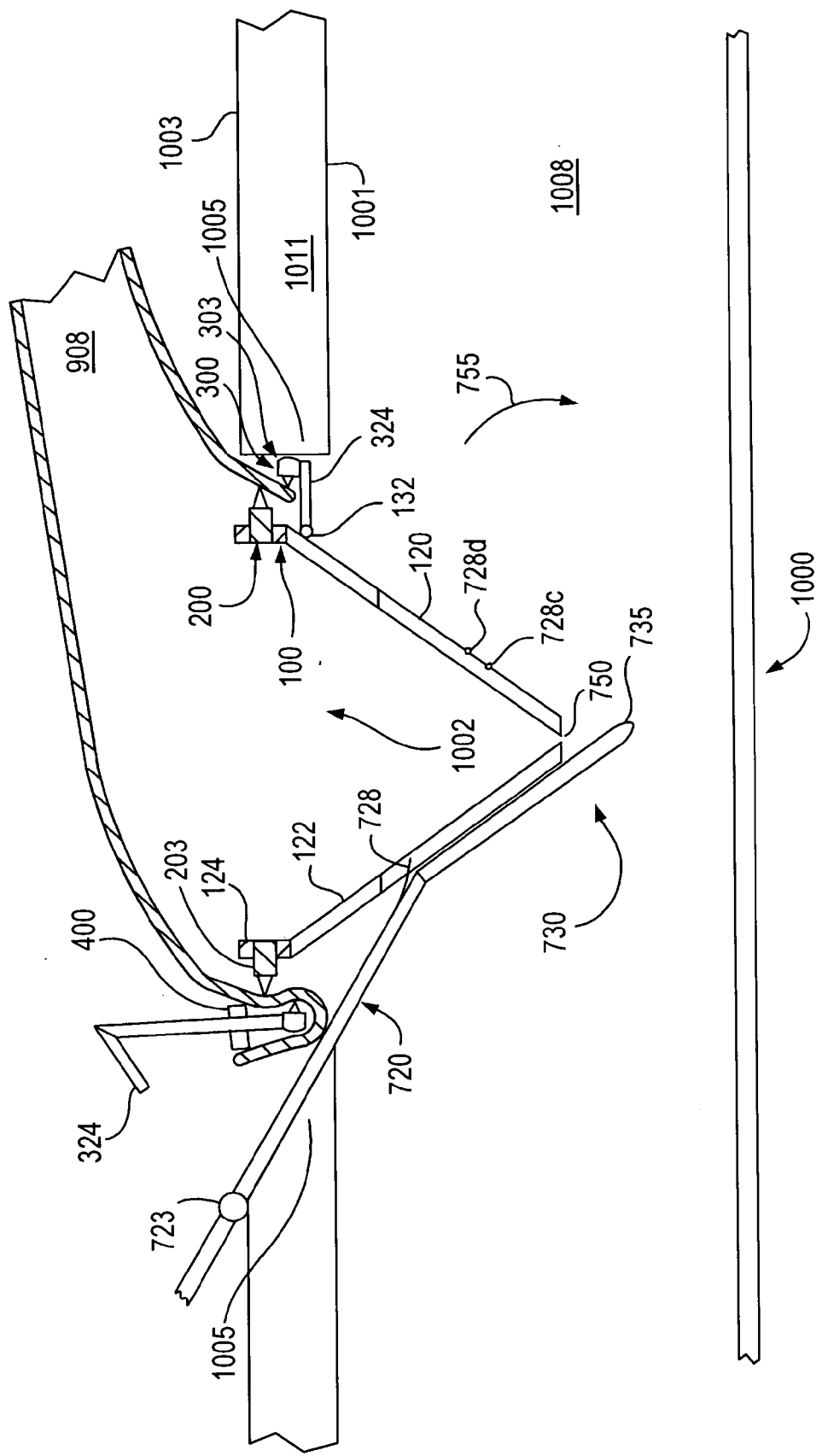
FIG. 33 is a simplified sectional view, similar to FIGS. 27, 28, 30, and 31, of the connector assembly of FIGS. 7, 7A, 14-19, and 27-32, in the closed position of FIGS. 17, 18, and 28-32, illustrated with the graft conduit of FIGS. 25-31, with the apparatus of FIGS. 19-24, 27, 28, and 30-32 in the yet even later stage of the procedure of FIGS. 31 and 32, and with a body conduit, in accordance with the invention.

As shown in FIG. 33, tip 735 may be inserted into aperture 1002 of a patient's tubular body tissue conduit 1000 (e.g., a patient's aorta requiring a bypass graft) to connect graft 900 to the body tissue conduit. Aperture 1002 may be formed, for example, by using a cutting catheter to cut through body tissue conduit 1000 at the desired anastomosis site (e.g., as in published PCT patent publication No. WO 99/38441, published Aug. 5, 1999, which is hereby incorporated by reference herein in its entirety). The natural elastic recoil of side wall 1011 of body tissue conduit 1000 seals aperture 1002 around lead portion 730 and connector assembly 500 so that there is little or no body fluid (e.g., blood) leakage out of the body conduit via aperture 1002. Tip 735 is gradually forced through aperture 1002 in the direction shown by arrow 755, thereby delivering convergence 750 and lead portion 730 into lumen 1008 of body conduit 1000 until external surface 303 of band 300 about periphery 905 of opening 902 of graft conduit 900 presses against the perimeter of aperture 1002 on medial portion 1005 of side wall 1011 of body tissue conduit 1000. The size and shape of external surface 303 of connector assembly 500 is preferably nominally larger than that of the aortotomy, thereby resulting in sufficient contact pressure for forming a seal between aperture 1002 and band 300 (and, thus, graft conduit 900). Bar 723 may be positioned along arm 720 such that it contacts exterior surface 1003 of body conduit 1000 to prevent delivery tool 700 from being inserted too far into lumen 1008.

Once this occurs, inside aortic fingers 112 may be completely released by loop portion 726 such that they may fully expand radially out towards their expanded configuration (see, e.g., FIGS. 9 and 10) and such that delivery tool 700 may be removed from the anastomosis site. In a preferred embodiment, fingers 112 may be completely released by winding wire 728 even more tightly onto spools 717 and 719 through rotation of disc 718 such that a frangible section about loop portion 726 of wire 728 may break within lumen 1008 of body tissue conduit 1000 due to the winding force at ends 728a and 728b (FIGS. 22 and 23). As shown in FIG. 33 (and FIG. 32 in hashed lines), once loop portion 726 breaks, wire 728 defines two separate wire segments spanning from ends 728c and 728d within lumen 1008 to ends 728a and 728b within housing portion 715 (FIG. 22), respectively. In another embodiment, the frangible section of wire 728 may not be about loop portion 726 but rather along a portion of wire 728 within lumen 727, lumen 729, or housing 715. In yet another embodiment, the physician may manually clip a portion of wire 728 such that it is separated into two wire segments. In yet still another embodiment, one of ends 728a or 728b may be released from its respective spool 717 or 719 such that wire 728 may just be wound onto the other one of the spools, for example.

Figure 34:
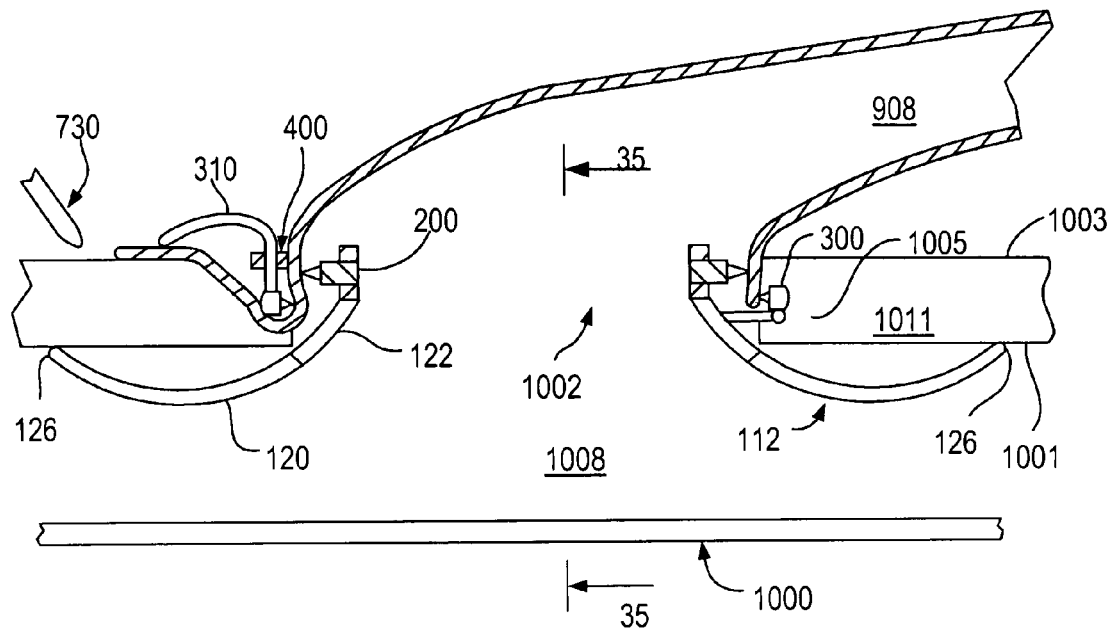
FIG. 34 is a simplified sectional view, similar to FIGS. 27, 28, 30, 31, and 33, of the connector assembly of FIGS. 7, 7A, 14-19, and 27-33, in the closed position of FIGS. 17, 18, and 28-33, illustrated with the graft conduit of FIGS. 25-31 and 33, with the apparatus of FIGS. 19-24, 27, 28, and 30-33 in a yet still even later stage of the procedure, and with the body conduit of FIG. 33, in accordance with the invention.
Figure 35A:
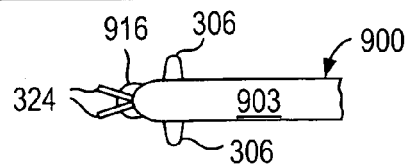
FIG. 35A is a top elevational view of the connector assembly of FIGS. 7, 7A, 14-19, and 27-35, in the closed position of FIGS. 17, 18, and 28-35, illustrated with the graft conduit of FIGS. 25-31, and 33-35, in the yet still even later stage of the procedure of FIGS. 34 and 35, and with the body conduit of FIGS. 33-35, taken from line 35A-35A of FIG. 35, in accordance with the invention.

With continued rotation of disc 718 in the direction of arrow 711 (FIGS. 22 and 23), the two wire segments are threaded out from eyelets 128 of fingers 112, through opening 725 and lumens 727 and 729, and possibly wound onto their respective spools 717 and 719, if desired. As wire 728 is threaded out from eyelets 128, fingers 128 are released from the confines of loop portion 726 and may freely expand radially out towards their expanded configuration shown in FIGS. 34 and 35. Once inside aortic fingers 112 are released from wire 728, delivery tool 700 is preferably withdrawn from lumen 1008 and the elasticity of conduit 1000 about aperture 1002 preferably closes about connector assembly 500. In their expanded configuration, fingers 112 may press against interior surface 1001 of body conduit 1000 about aperture 1002 with a force opposite that applied by outside aortic fingers 306 (and, preferably, by tip element 324) against exterior surface 1003 of body conduit 1000 about aperture 1002 for sealing the anastomosis (see, e.g., FIGS. 35 and 35A). As shown in FIG. 34, tissue of graft conduit 900 adjacent toe 916 may be pulled into the aortotomy at medial portion 1005, below band 300, and then back out to a position held between expansion portion 310 of assembly 500 and exterior wall 1003 of conduit 1000, whereas tissue of conduit 900 at heel 920 may be held at medial portion 1005 of the aortotomy between ring 200 and band 300. It is to be understood that the cross-sectional area of the ostium of the completed anastomosis between opening 911 in graft conduit 900 and aperture 1002, as shown in FIGS. 34-35A, is defined by the cross-sectional area of opening 125 of band 124 (see, e.g., FIGS. 10 and 29), which may be larger than that of graft conduit 900, as described above.

In another embodiment, aperture 1002 may be formed by making a round or oval incision in side wall 1011 of body tissue conduit 1000, depending on the shape of opening 125 of the connector body 100 being used, for example. This may be accomplished in many ways, including punching an aortotomy, by controlling and cutting aorta tissue in a shape of an oval or circle in a desired manner without having to make a previous incision into the tissue. An aortotomy may also be accomplished by using electric cautery, or ultrasonic or harmonic frequencies to generate a hole in the tissue of a desired and controlled shape such as an oval.

Figure 36:
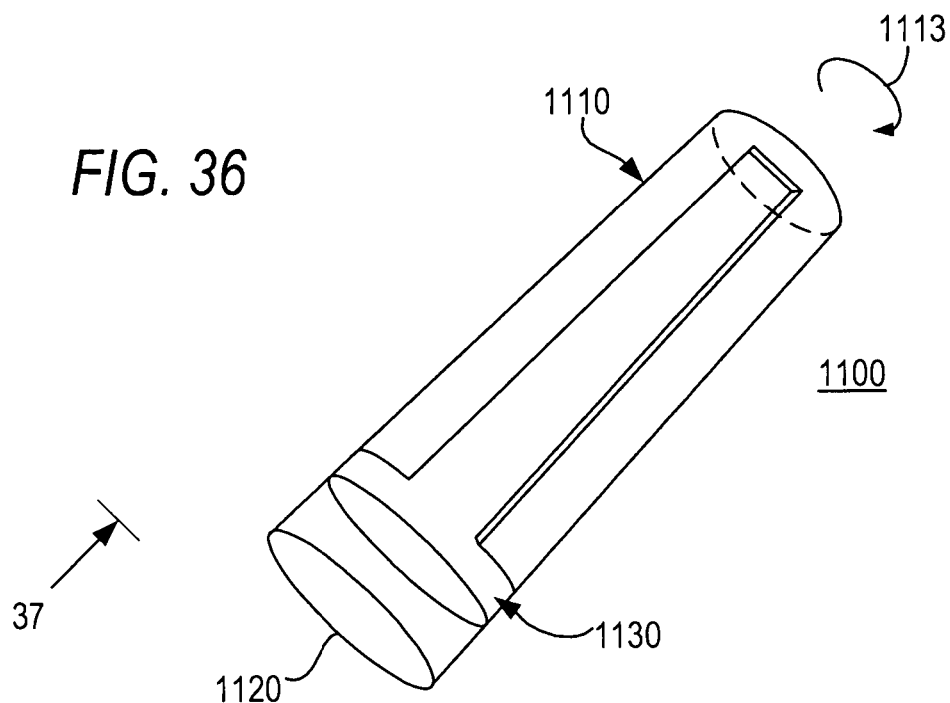
FIG. 36 is a perspective view of a vessel incision tool in accordance with the invention.
Figure 37:
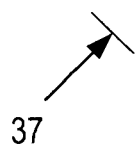
FIG. 37 is an end view of the vessel incision tool of FIG. 36, taken from line 37-37 of FIG. 36.

FIGS. 36 and 37 show a device 1100 that is able to provide an aortotomy in yet another way, by rotating a tube 1110 having a cutting edge 1120 in direction 1113 through a given trajectory created by a mandrel 1130 within tube 1110. Mandrel 1130 may be round, oval, or any other similar shape. The driving of the preferably thin-walled material of cutting edge 1120 (e.g., nitinol or stainless steel) through the given geometry of mandrel 1130 creates a path and subsequently a hole of the given shape which is not necessarily round.

In yet another embodiment, aperture 1002 may be formed by making an incision of a controlled, predetermined length in the side wall of body tissue conduit 1000 (e.g., as in U.S. patent application Ser. No. 10/678,403, filed Oct. 4 2003, which is hereby incorporated by reference herein in its entirety).

Figure 38:
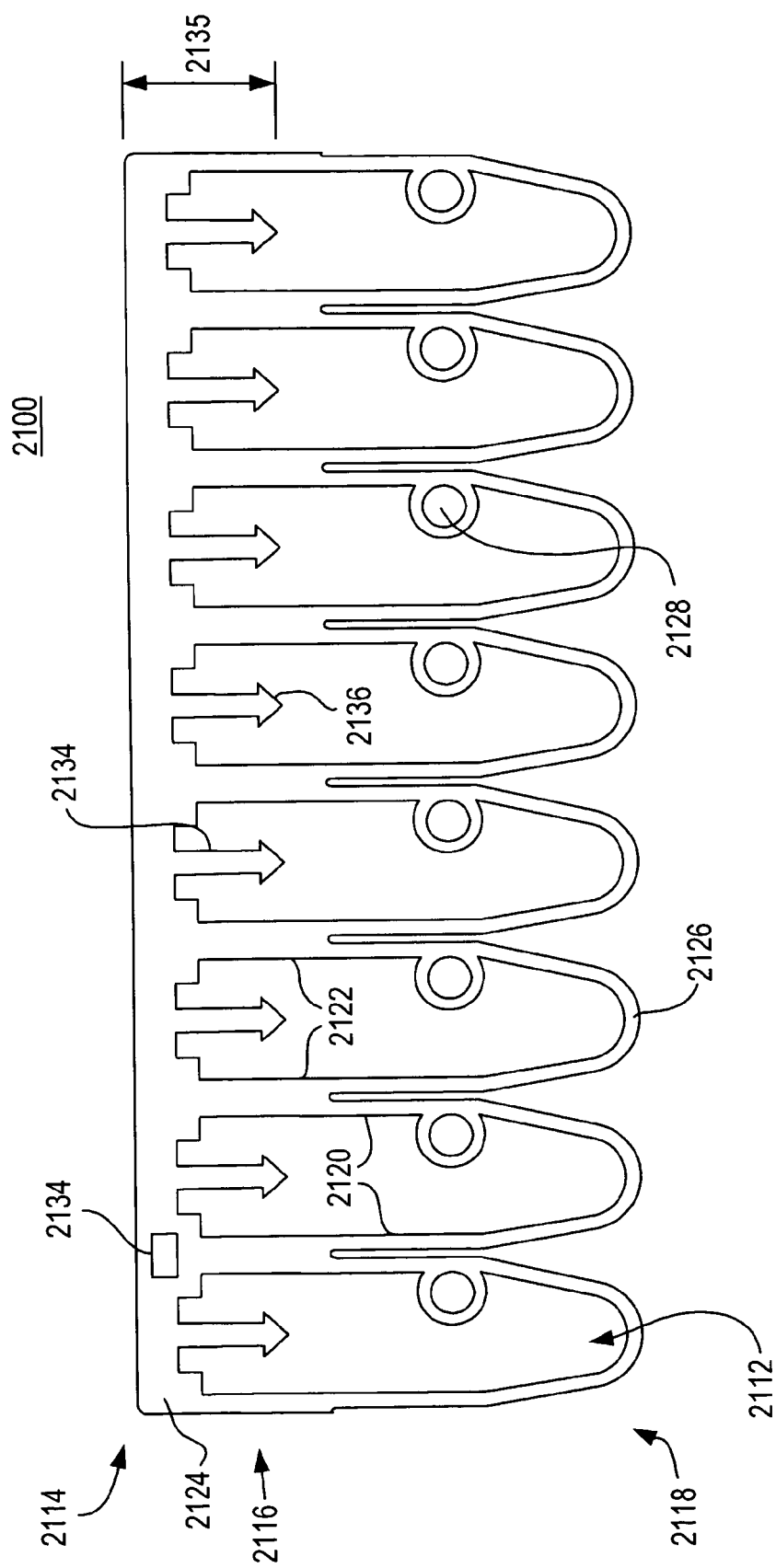
FIG. 38 is a planar development of the structure of an other illustrative embodiment of a connector body constructed in accordance with the invention.
Figure 39:
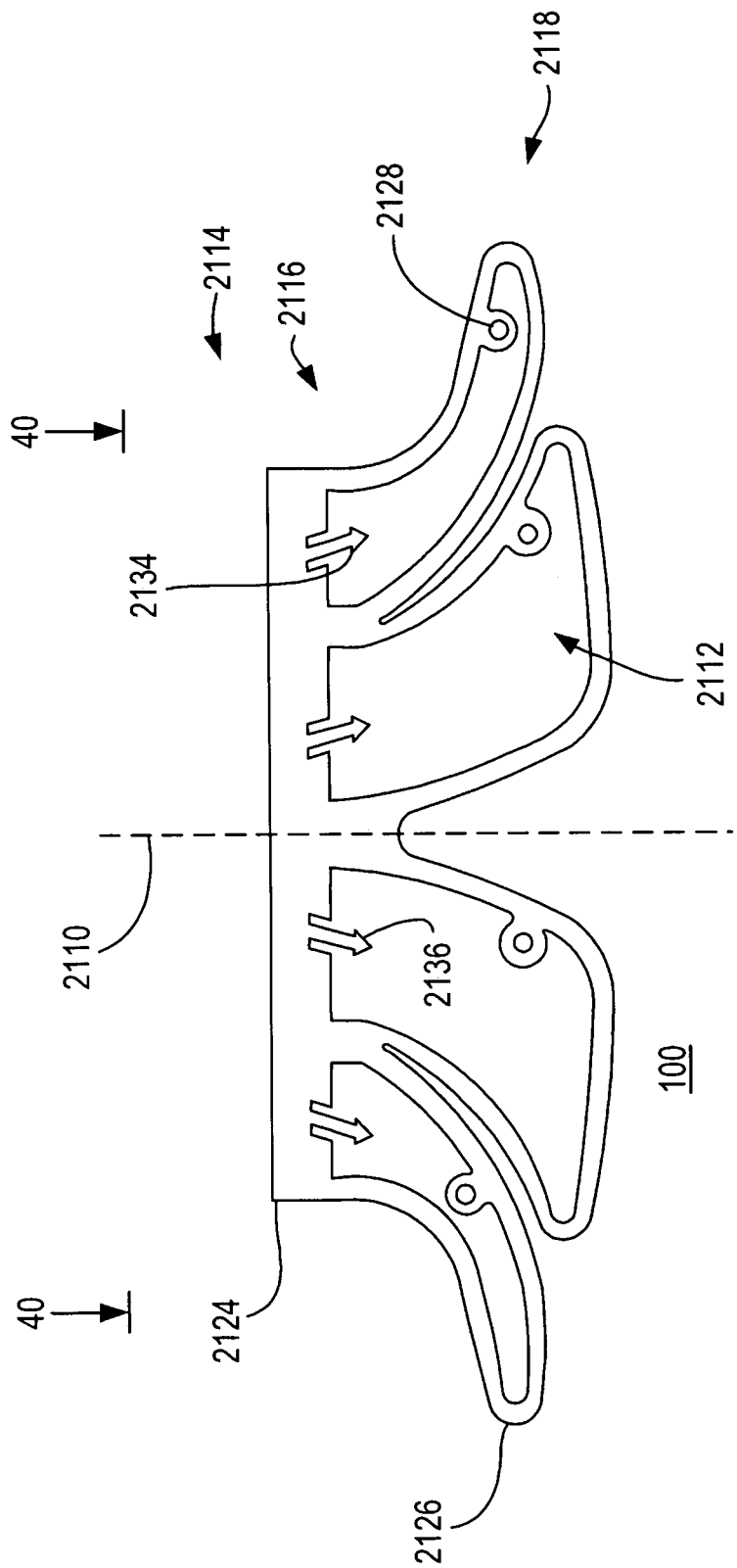
FIG. 39 is a perspective view of the connector body of FIG. 38, in an expanded configuration, in accordance with the invention.
Figure 40:
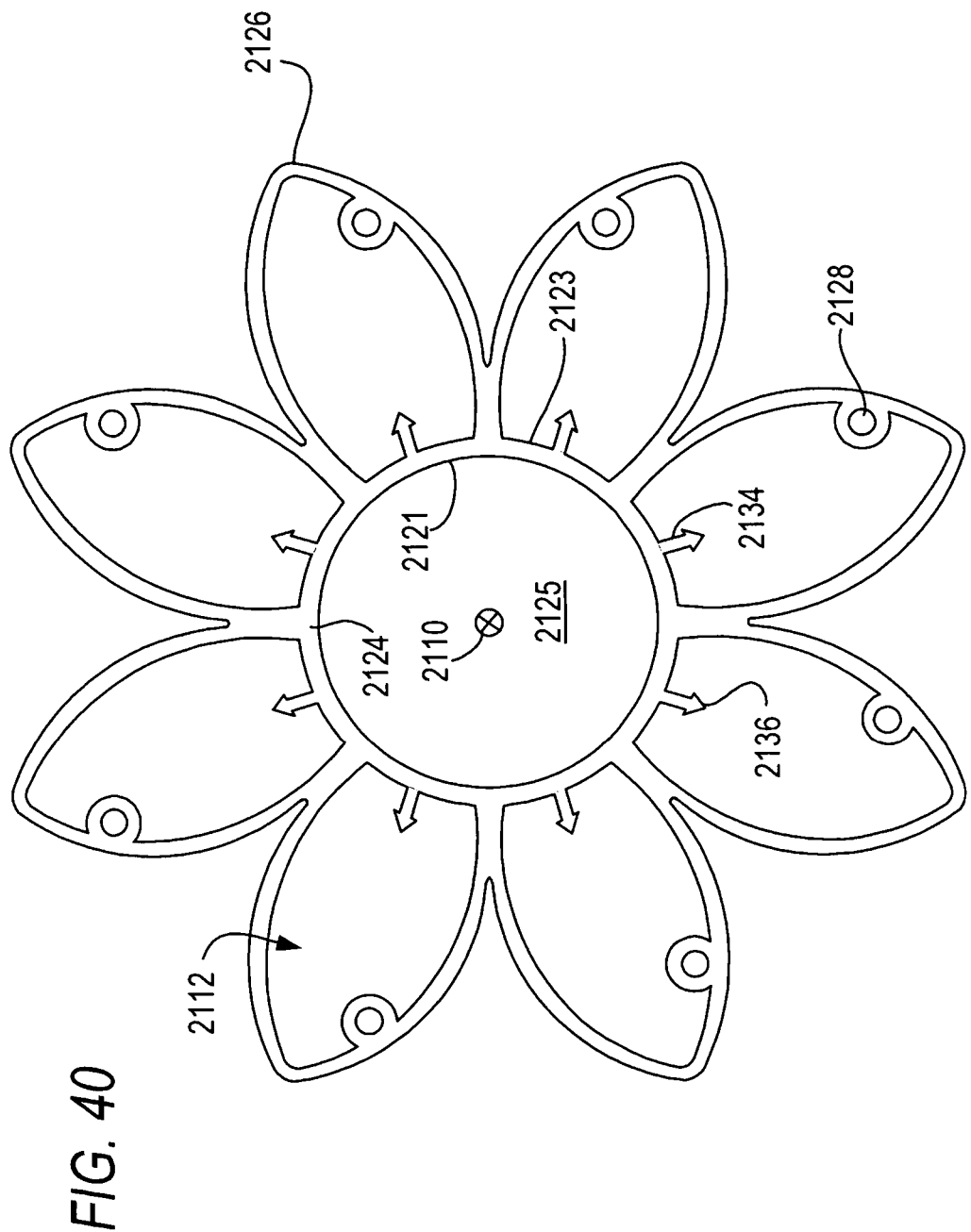
FIG. 40 is a top elevational view of the connector body of FIGS. 38 and 39, taken from line 40-40 of FIG. 39.

In another preferred embodiment of the connector assembly of the present invention, FIG. 38 shows a planar development of what is actually, preferably, an integral, one-piece (unitary), annular, cellular connector body 2100, similar to connector body 100. In particular, the left and right edges of the structure shown in FIG. 38 are actually, preferably, joined to and integral with one another. Thus, the actual structure of connector body 2100 is as shown in FIGS. 39 and 40, although FIG. 38 is useful to more clearly reveal certain details of various features of connector body 2100. A central longitudinal axis 2110 about which connector body 2100 is annular is shown in FIGS. 39 and 40.

A particularly preferred material for connector body 2100 is nitinol. Other examples of suitable materials include tantalum, tungsten, stainless steel, platinum, silicone, and polyurethane. Connector body 2100 may be advantageously produced by starting with a single, unitary tube, such as a hypotube, and removing selected material until only the structure shown in FIGS. 39 and 40 remains. For example, laser cutting may be used to remove material from the starting tube in order to produce connector body 2100. After removing the material to form the structure shown in FIG. 38, the machined tube may be placed in a mold and heat-shaped into approximately the geometry that connector body 2100 will assume after deployment. For example, connector body 2100 may be heat-shaped into the geometry shown in FIGS. 39 and 40. The shape of connector body 2100 is retained after removing connector body 2100 from the mold due to the properties of nitinol.

Like connector body 100, connector body 2100 may be described as including annularly spaced cell portions or inside aortic fingers 2112. According to one embodiment, connector body 2100 includes eight repeating cell portions 2112. Connector body 2100 may have fewer or more than eight of cell portions 2112, depending on the axial length and perimeter of the tube used to manufacture connector body 2100 and the resulting anastomosis ostium desired. Alternatively, the structure of connector body 2100 may have different configurations of cells and geometries.

Each cell 2112 includes a pair of annularly spaced members 2120. Each cell 2112 typically also includes a pair of annularly spaced members 2122. The proximal end of each member 2122 is connected to the distal ends of adjacent members 2120 of adjacent cells 2112, and the distal ends of members 2122 are connected to the proximal portion of an annular element 2124. Annular element 2124 defines the distal portion 2114 of connector body 2100, whereas annularly spaced members 2122 define the medial portion 2116 of connector body 2100.

The proximal ends of annularly spaced members 2120 of each cell 2112 are typically connected to one another at an annularly extending member 2126, which is preferably curved proximally. A pair of members 2120 and a member 2126 define the proximal portion 2118 of each cell portion 2112.

Some or all of cell portions 2112 at its distal end may include a tissue holding feature that in this case includes a distal member 2134 that has a barb-like free end portion 2136 that is sharply pointed and that points toward proximal portion 2118. Distal member 2134 may be connected to annular element 2124. A typical distal member 2134 may have a length 2135 in a range from about 0.035 inches to about 0.075 inches. (It should be noted that length 2135 includes the width of annular element 2124.) However, the dimensions of distal member 2134 may be altered according to the wall thickness of the graft conduit to be loaded thereon. Each of distal members 2134 is deflectable radially outward from the remainder of the structure of connector body 2100, as shown, for example, in FIGS. 39 and 40.

The above-mentioned outward deflection of distal members 2134 may be produced by putting connector body 2100 on a mandrel and prying members 2134 radially outward. Like connector body 100, connector body 2100 may also typically require other processing appropriate for an implantable device such as, for example, polishing, passivation, cleaning, and sterilizing.

As shown in this example, connector body 2100 preferably has a fixed cross-sectional area. Specifically, annular element 2124 of distal portion 2114 is an annular structure having a fixed cross-section, an outer surface 2123, an inner surface 2121, and an opening 2125 defined therein, which may be round, oval, or any other substantially smooth shape. In another preferred embodiment, connector body 2100 may be expandable or enlargeable.

As shown in FIGS. 39 and 40, inside aortic fingers 2112 may expand radially out from distal portion 2114. As described above, fingers 2112 may expand to this configuration created by heat-shaping connector body 2100. The expansion of fingers 2112 is preferably elastic. One adjacent member 2120 of each finger 2112 may be provided with an aortic eyelet 2128 for interaction with an aortic delivery tool, such as tool 700 described above, such that proximal portion 2118 may be configured to pass through an aperture in an aorta, as described above with respect to connector assembly 500 and aorta 1000.

In this embodiment, the end of a graft tissue conduit, such as graft tissue conduit 900, may be loaded onto the tissue holding features provided by distal members 2134 with barb-like free end portions 2136 of connector body 2100. Members 2134 may penetrate and pass through the side wall of graft conduit 900 from interior surface 901 to exterior surface 903 as a result of, for example, compressing the graft against free end portions 2136 with a physician's tool (e.g., the vein piercing tool described in Logan et al. U.S. Pat. No. 6,669, 256), thereby forcing the free end portions to pierce through the graft wall. The sharpened tips of free end portions 2136 may facilitate penetration of conduit 900, while the blunt rear surfaces thereof may resist withdrawal therefrom, like a barb. Conduit 900 may be additionally or alternatively directly sutured to connector body 2100.

Figure 41:
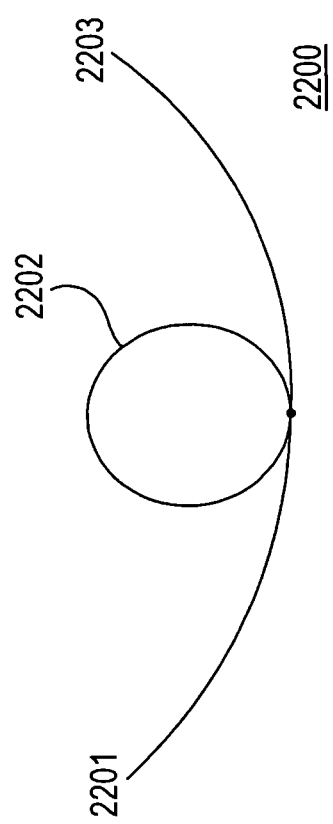
FIG. 41 is a top elevational view of a looping wire to be used in conjunction with the connector body of FIGS. 38-40.
Figure 42:
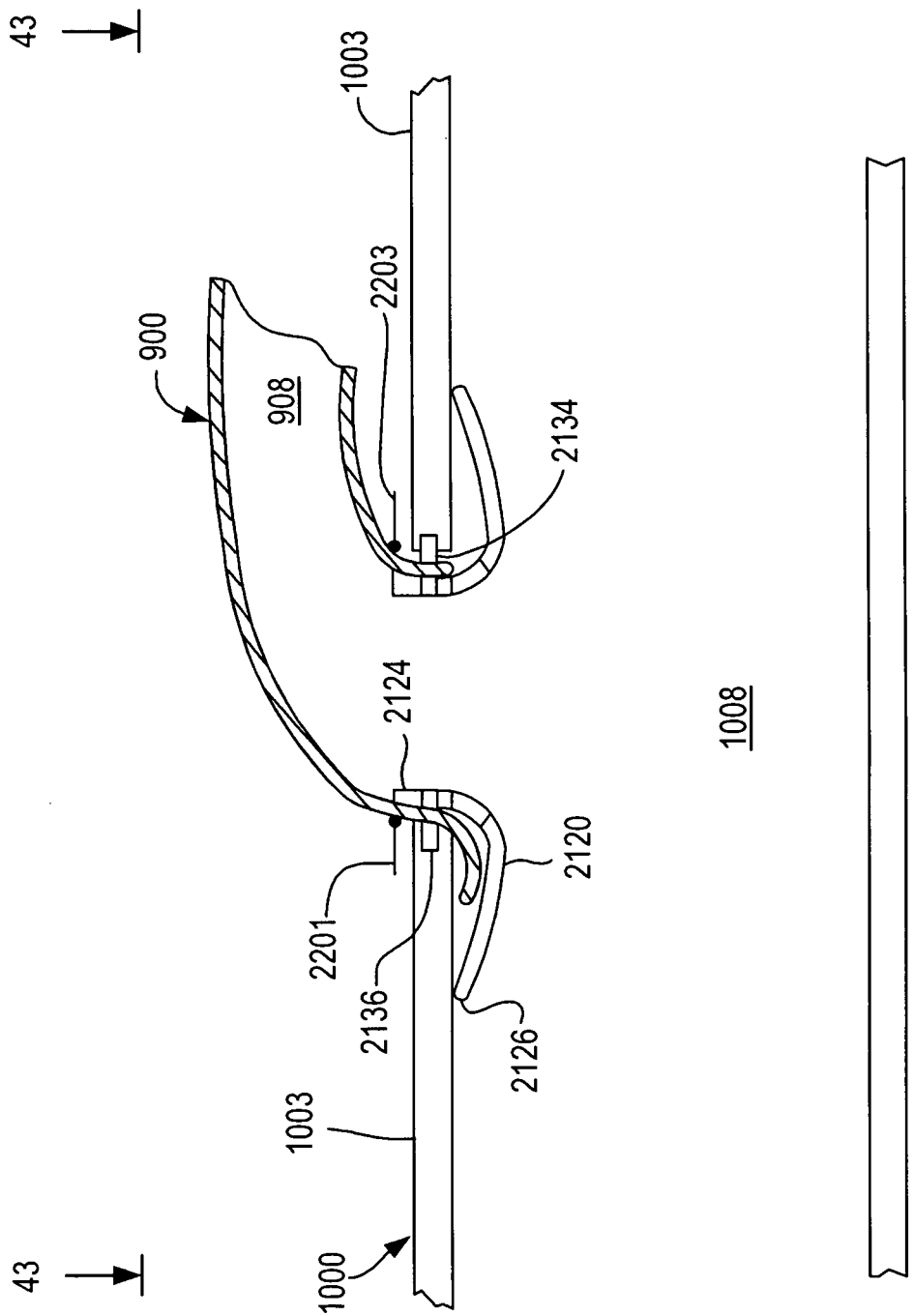
FIG. 42 is a simplified sectional view of the connector body of FIGS. 38-40 in conjunction with the looped wire of FIG. 41, illustrated with the graft conduit of FIGS. 25-31 and 33-35, and with the body conduit of FIGS. 33-35, in accordance with the invention.
Figure 43:
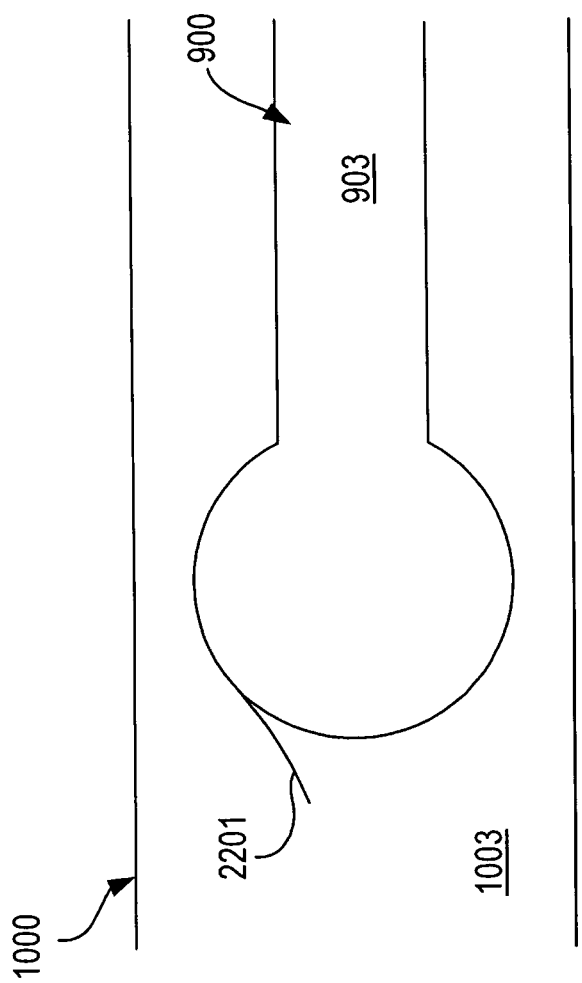
FIG. 43 is a top elevational view of the connector body of FIGS. 38-40 and 42 in conjunction with the looped wire of FIGS. 41 and 42, illustrated with the graft conduit of FIGS. 25-31, 33-35, and 42, and with the body conduit of FIGS. 33-35 and 42, taken from line 43-43 of FIG. 42, in accordance with the invention.

Connector body 2100 may be loaded into body tissue conduit 1000 in a way similar to how connector assembly 500 is attached to body tissue conduit 1000 (FIGS. 30-35), for example. However, a line or wire 2200, as shown in FIG. 41, may be provided to wrap around annular element 2124 external to graft conduit 900 once conduit 900 has been loaded onto connector body 2100, for example. Wire 2200 may form a loop 2202 for tightly winding around annular element 2124, above distal members 2134, and may provide ends 2201 and 2203 to extend therefrom for contacting exterior wall 1003 of body conduit 1000 about aperture 1002, as shown in FIGS. 42 and 43, for example, although, in another embodiment, wire 2200 may similarly form a loop 2202 for tightly winding around annular element 2124, below distal members 2134 or a weaving combination of above and below distal members 2134. Wire 2200 may also be used with any of the other connector assemblies described herein, instead of or in addition to an outside-the-graft retaining band, either above or below an inside-the-graft retaining ring.

This embodiment of connector body 2100, wherein the tissue holding features are provided at annular element 2124 and can retain a graft conduit thereon may obviate the need for an inside-the-graft retaining ring and/or an outside-the-graft retaining band and collar. As shown in FIG. 42, the sharpened tips of free end portions 2136 may facilitate penetration of conduit 900.

Figure 44:
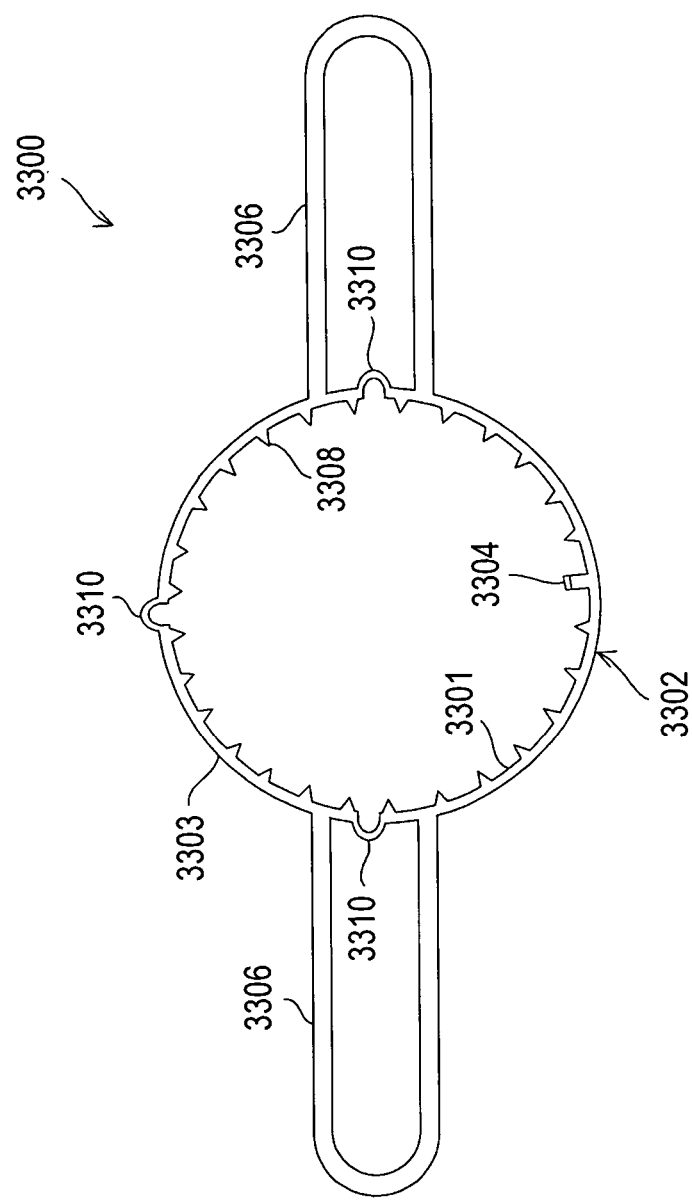
FIG. 44 is a top elevational view of an other illustrative embodiment of an outside-the-graft retaining band in accordance with the invention.

In another preferred embodiment of the connector assembly of the present invention, FIG. 44 shows in isolation a substantially annular outside-the-graft retaining element or band 3300, similar to band 300. Like band 300, a particularly preferred material for band 3300 is nitinol. Other examples of suitable materials include tantalum, tungsten, stainless steel, platinum, silicone, and polyurethane.

Figure 45:
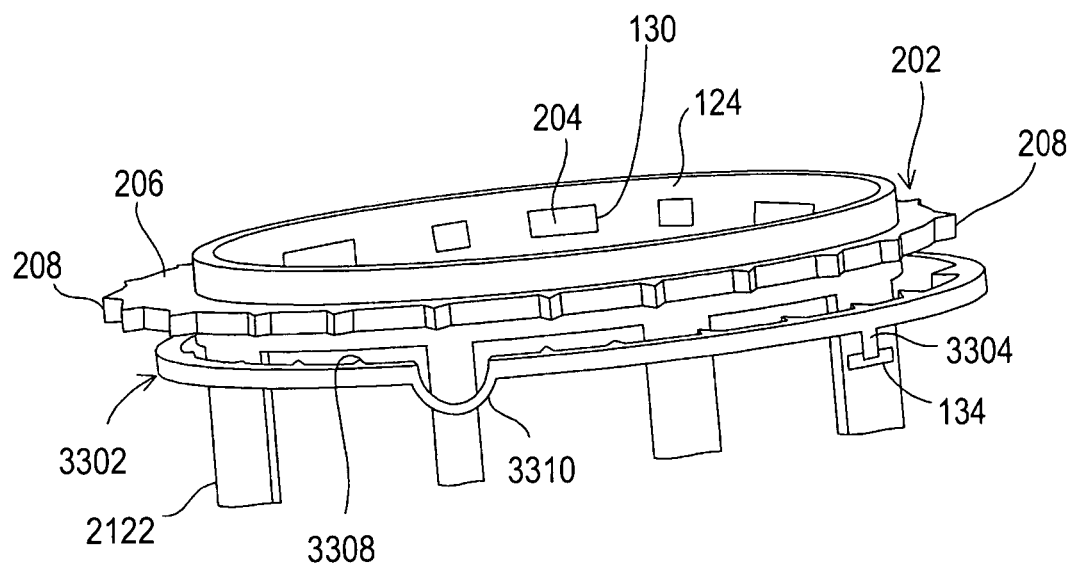
FIG. 45 is a rear elevational view, similar to FIG. 18, of the outside-the-graft retaining band of FIG. 44, assembled with the connector body of FIG. 8 and the inside-the-graft retaining ring of FIG. 11, in the closed position, in accordance with the invention.

Outside-the-graft retaining band 3300 may generally be described as including a substantially annular element 3302 with an inner surface 3301, whose size and shape, in a preferred embodiment, may match that of outer surface 203 of annular element 202 of inside-the-graft retaining ring 200 (see, e.g., FIG. 11). Tooth 3304 is provided at a portion of outer surface 3303 of element 3302 and is appropriately placed such that it interacts with a band slot 134 (see, e.g., FIG. 8) of connector body 100 when it is heat treated or bent out of the plane of annular element 3302 and then parallel thereto, and when band 3300 is coupled to connector body 100, as shown in FIG. 45. Connector body 100 may be provided with band slot 134 instead of hinge joint 132 when band 3300 is desired to be used instead of band 300. Band slot 134 of connector body 100 and tooth 3304 of band 3300 interact such that band 3300 may be coupled to connector body 100 when band 3300 is positioned in a "closed" position thereabout, as described in more detail below. Connector body 2100 may also be provided with a band slot 2134 (see, e.g., FIG. 38) when band 3300 is desired to be used instead of, or in addition to, wire 2200. Band slot 2134 of connector body 2100 and tooth 3304 of band 3300 interact such that band 3300 may be coupled to connector body 2100 when band 3300 is positioned in a "closed" position thereabout (see, e.g., FIG. 46) Band 3300 may also include one or more outside-the-graft retention features or teeth 3308 projecting inwardly from inner surface 3301 of band 3300 about element 3302.

Band 3300 may also be described as including one or more outside aortic fingers 3306, similar to fingers 306, projecting outwardly from element 3302 in substantially the same plane as element 3302 such that they engage the exterior wall of the aorta when they are bent or heat treated to curve out of the plane and when the anastomosis is completed. According to one embodiment, band 3300 includes two diametrically spaced outside aortic fingers 3306 projecting from element 3302. Band 3300 may have fewer or more than two aortic fingers 3306, depending on the size and shape of the connector body to be used, for example.

One or more resilient expansion portions 3310 are included as an integral element of band 3300, interrupting substantially annular element 3302. According to one embodiment, band 3300 includes three spaced resilient expansion portions 3310. Band 3300 may have fewer or more than three expansion portions 3310, depending on the size and shape of band 3300, for example.

Figure 46:
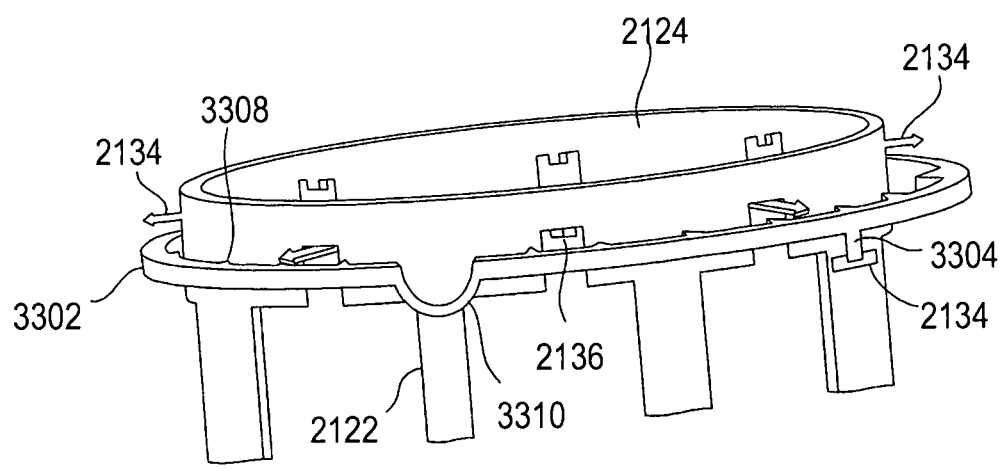
FIG. 46 is a rear elevational view, similar to FIGS. 18 and 45, of the outside-the-graft retaining band of FIGS. 44 and 45, assembled with the connector body of FIG. 38, in the closed position, in accordance with the invention.

Resilient expansion portions 3310 enable expansion of the size and shape of the opening defined by inner surface 3301, thereby allowing band 3300 to pass beyond outer surface 203 and flanges 206 of inside-the-graft retaining ring 200 (or, in another embodiment, free end portions 2136 of band 2124) while tooth 3304 may interact with band slot 134 (e.g., by sliding therein) to maintain the relative positioning of band 3300 and connector body 100 (or with band slot 2134 to maintain the relative positioning of band 3300 and connector body 2100), for example. Thereafter, expansion portions 3310 enable resilient contraction of inner surface 3301 substantially to its original size, as described above with respect to band 300 (see, e.g., FIGS. 15 and 16), for holding band 3300 in its closed position along with tooth 3304 and band slot 134/2134, as shown in FIGS. 45 and 46, respectively, wherein outside aortic fingers 306/3306 are not shown for the sake of clarity. Therefore, once a graft conduit has been loaded onto a connector body of the present invention, band 3300 may be coupled to the connector body, expanded, and then contracted thereabout in order to hold the graft conduit to the connector assembly, with or without the use of band 300 and/or wire 2200.

It should be noted that, although apparatus and methods for making anastomoses of the present invention have been described as providing outside-the-graft retention features (e.g., wire 2200 and features 308 and 3308) generally below inside-the-graft retention features (e.g., features 208 and members 2134) about a connector body, the present invention also relates to apparatus and methods for making anastomoses that provide outside-the-graft retention features not only below, but also above and/or at the same elevation as inside-the-graft retention features about a connector body. This may be accomplished with the previously described connector assembly embodiments by altering the relative positioning of hinge 132 or band slots 134/2134 and slots 130 or retention features 2134, for example.

Figure 47:
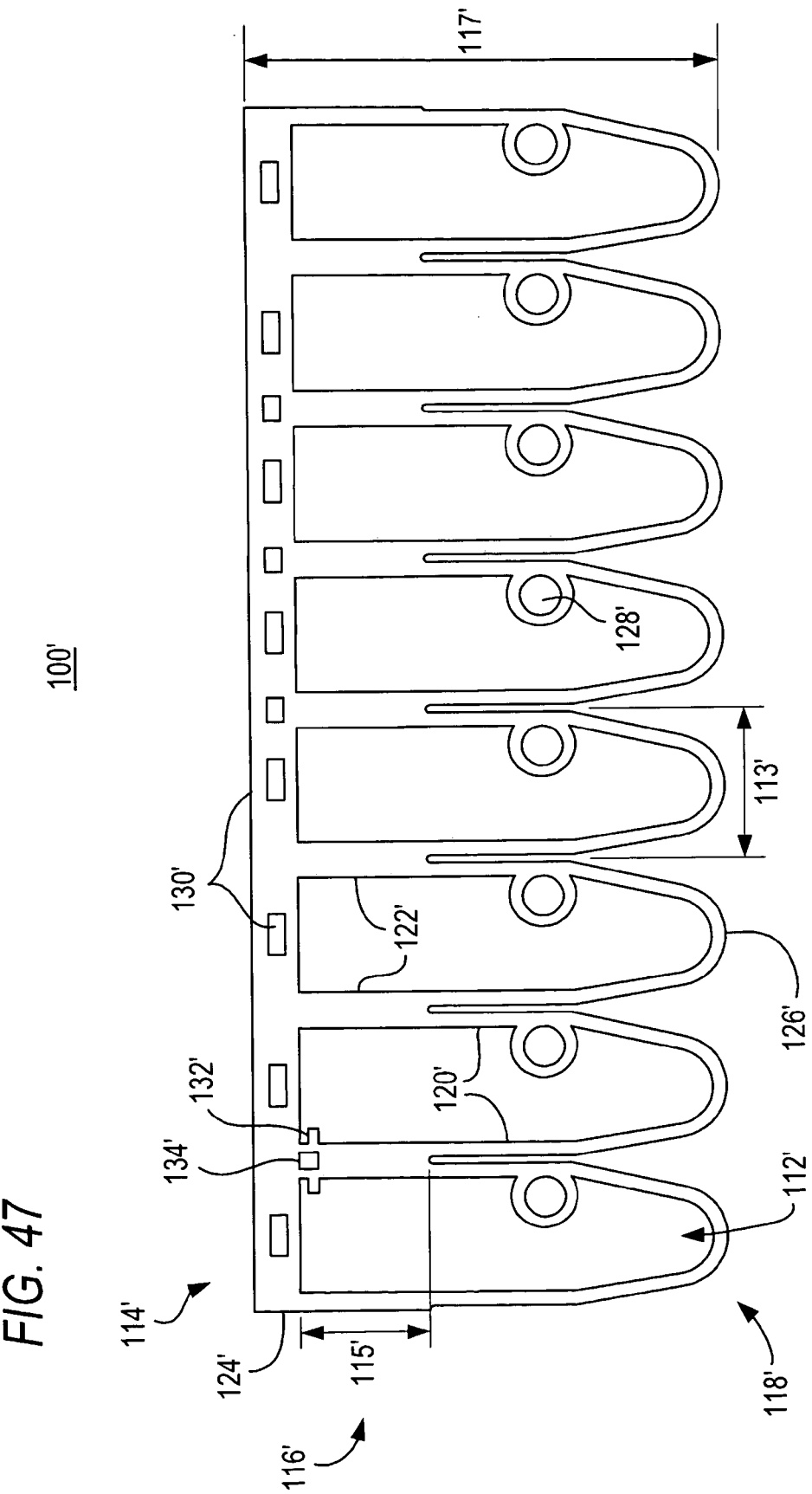
FIG. 47 is a planar development of the structure of an other illustrative embodiment of a connector body constructed in accordance with the invention.
Figure 48:
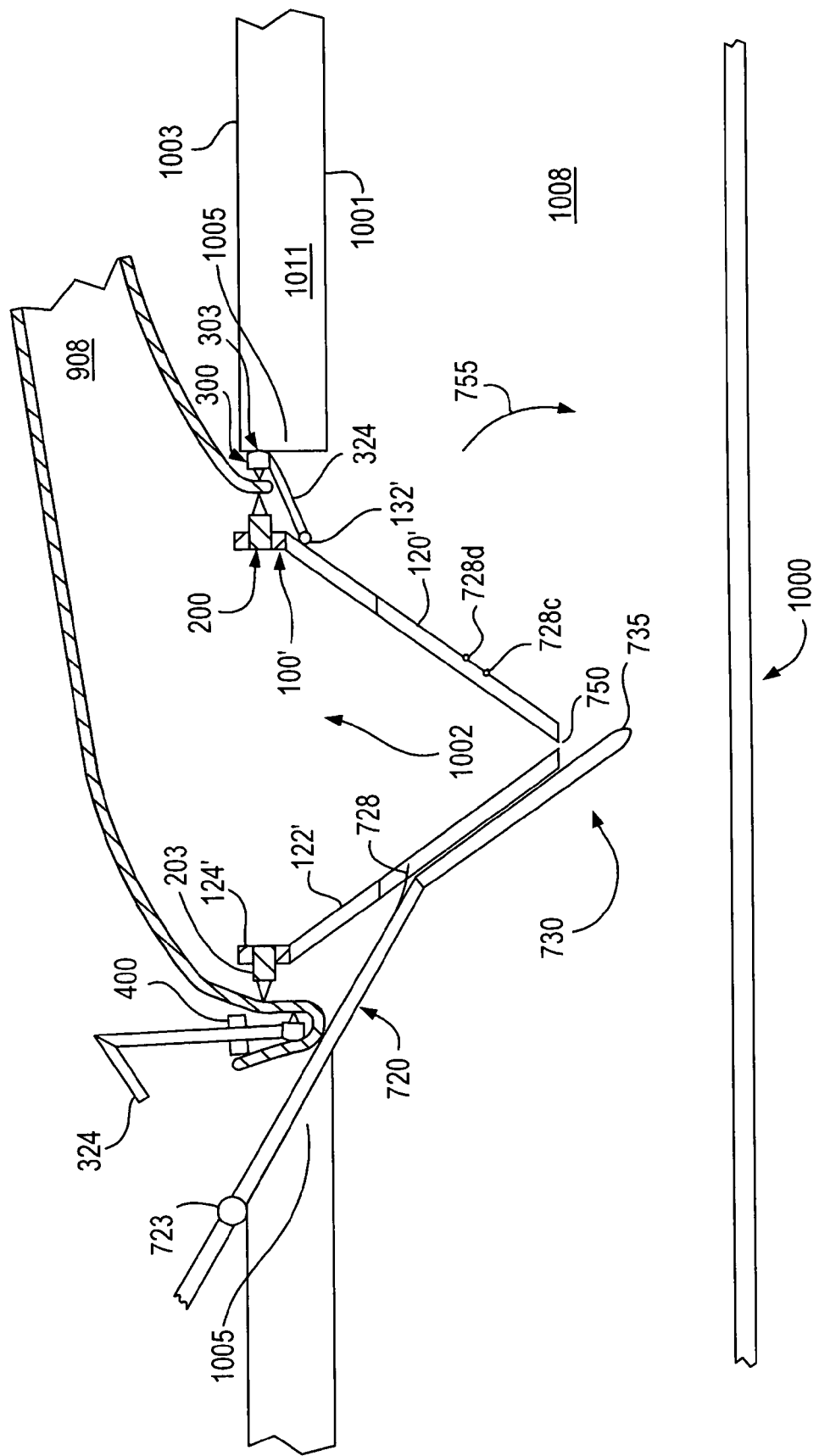
FIG. 48 is a simplified sectional view, similar to FIGS. 27, 28, 30, 31, and 33, of the connector assembly of FIGS. 7, 7A, 14-19, and 27-35, in the closed position of FIGS. 17, 18, and 28-35, but with the connector body of FIG. 47, illustrated with the graft conduit of FIGS. 25-35, with the apparatus of FIGS. 19-24, 27, 28, and 30-33 in the yet even later stage of the procedure of FIGS. 31-33, and with the body conduit of FIGS. 33-35, in accordance with the invention.

As shown in FIG. 47, for example, hinge 132' and band slot 134' of connector body 100' are significantly closer to slots 130' than hinge 132 and band slot 134 of connector body 100 are to slots 130 (see, e.g., FIG. 8). This geometry of connector body 100' allows for the retention features of outside-the-graft retaining band 300 to be at relatively the same elevation as the retention features of inside-the-graft retaining ring 200 at the heel of graft conduit 900, while still allowing the retention features of band 300 to be below the retention features of ring 200 at the toe of graft conduit 900, as shown in FIG. 48, for example.

Figure 49:
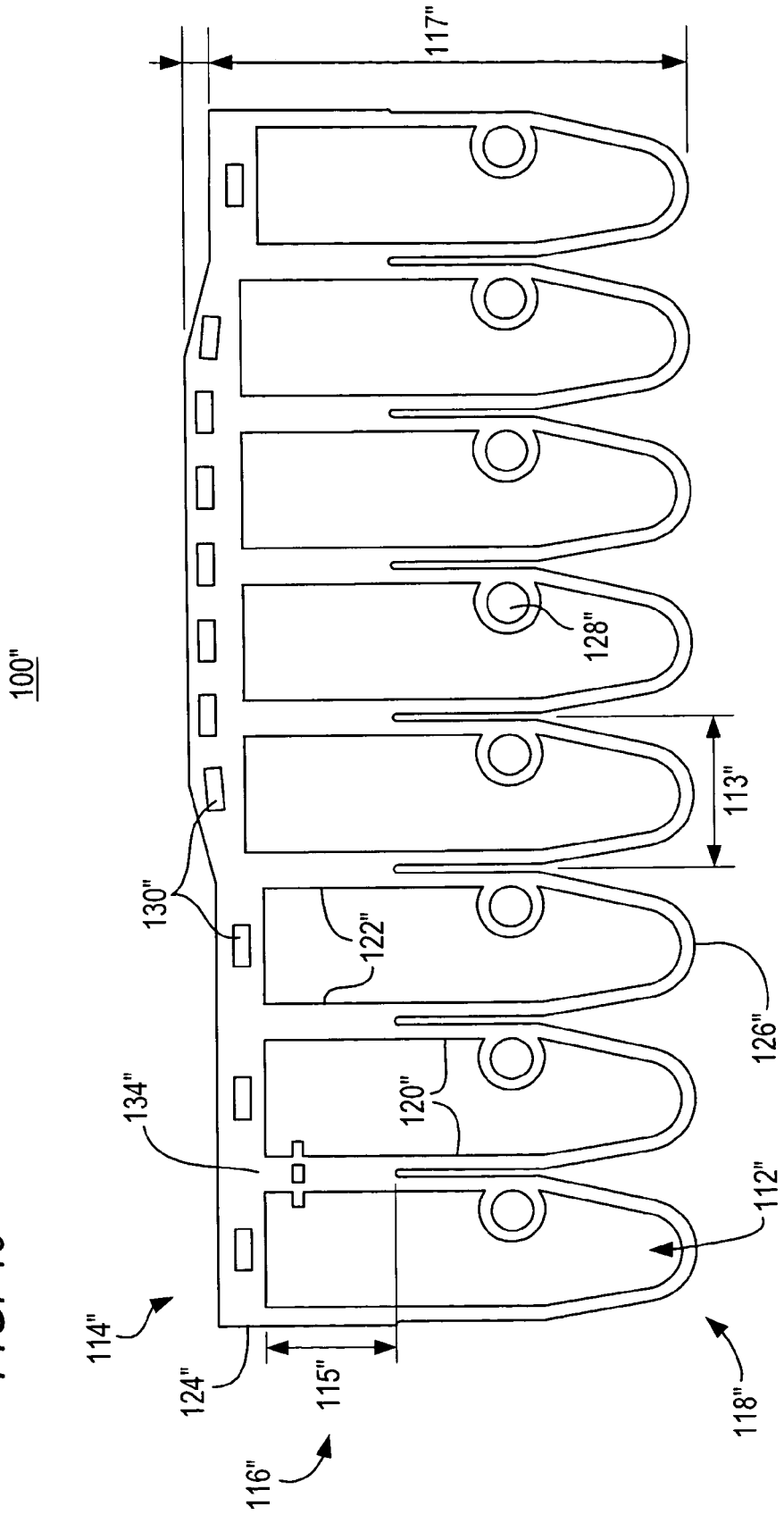
FIG. 49 is a planar development of the structure of an other illustrative embodiment of a connector body constructed in accordance with the invention.
Figure 50:
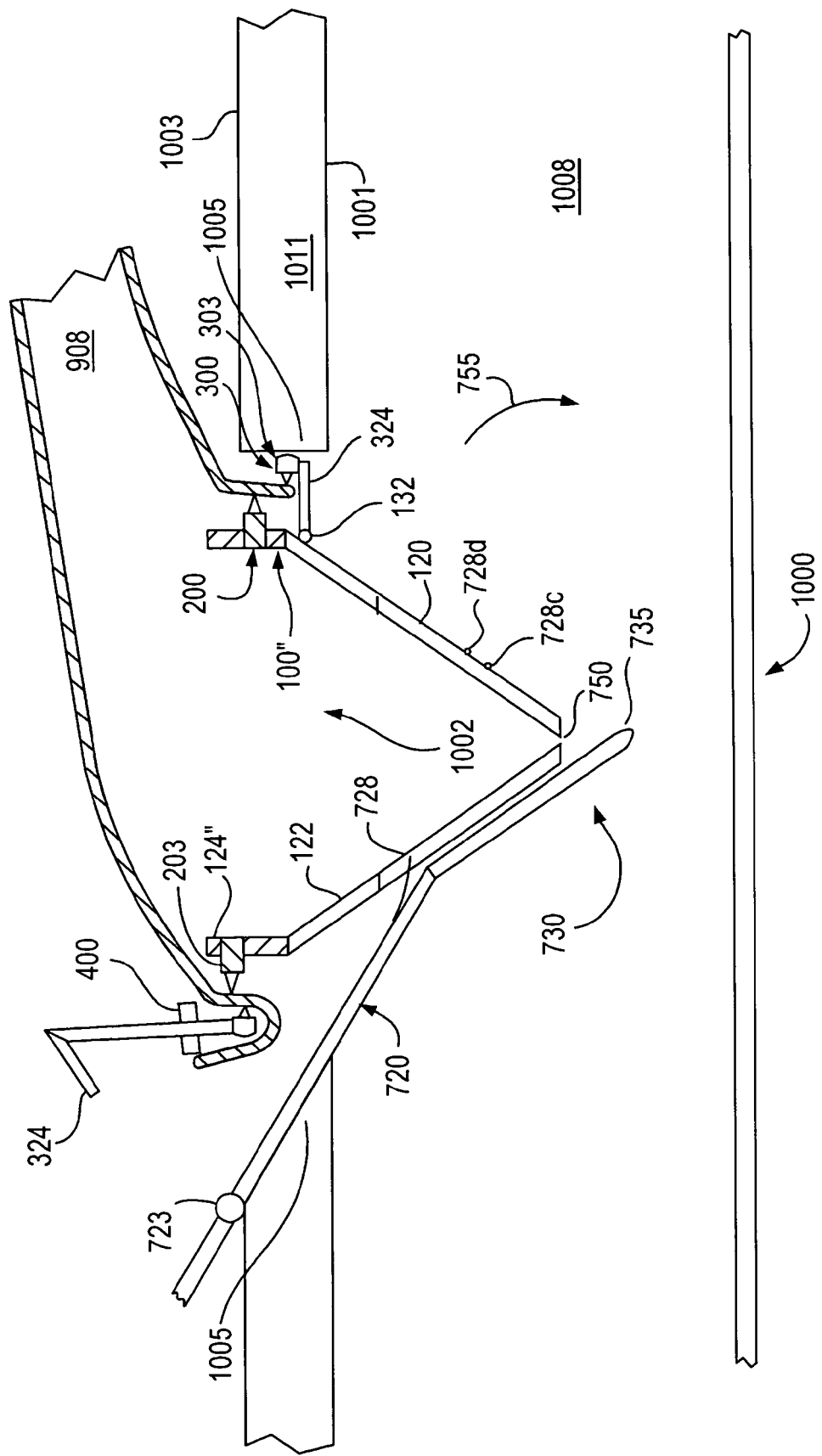
FIG. 50 is a simplified sectional view, similar to FIGS. 27, 28, 30, 31, 33, and 48, of the connector assembly of FIGS. 7, 7A, 14-19, and 27-35, in the closed position of FIGS. 17, 18, and 28-35, but with the connector body of FIG. 49, illustrated with the graft conduit of FIGS. 25-35, with the apparatus of FIGS. 19-24, 27, 28, and 30-33 in the yet even later stage of the procedure of FIGS. 31-33, and with the body conduit of FIGS. 33-35, in accordance with the invention.

As shown in FIGS. 49 and 50, for example, the slots 130" of connector body 100" opposite those adjacent to hinge 132" and band slot 134" are significantly more distal from hinge 132" and band slot 134" than those slots 130 are from hinge 132 and band slot 134 of connector body 100 (see, e.g., FIG. 8). This geometry of connector body 100" allows for the retention features of outside-the-graft retaining band 300 to be even further below the retention features of inside-the-graft retaining ring 200 at the toe of graft conduit 900 than at the heel of graft conduit 900, as shown in FIG. 50, for example.

A "fixed stenosis" connector configuration refers to the positioning of the graft heel tissue in such a way that it is substantially always at the same position relative to exterior surface of the body tissue conduit, regardless of the body tissue conduit's medial wall thickness. Therefore, the lumen restriction will be of a fixed amount and not dependant on the body tissue conduit thickness.

Figure 51:
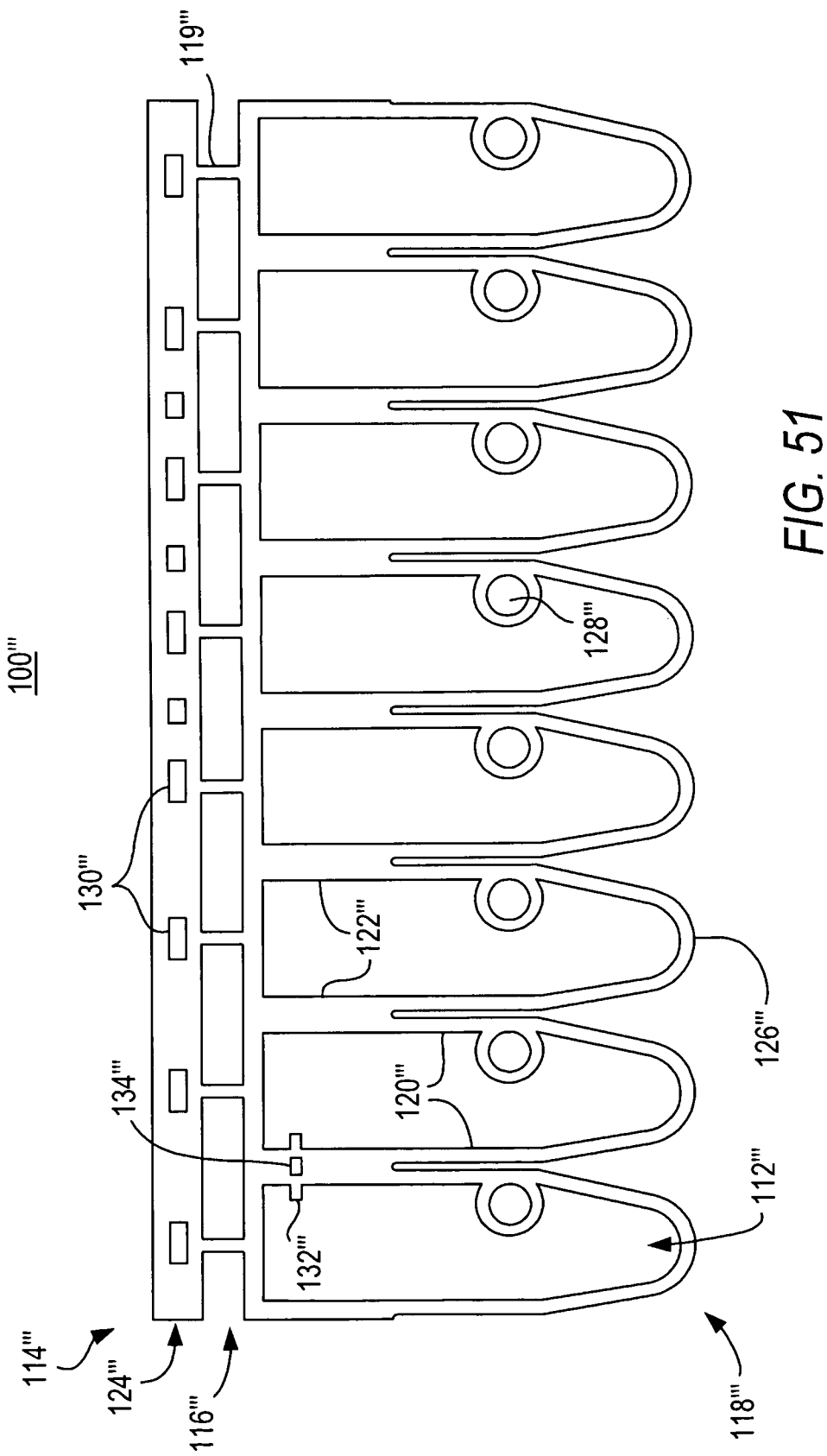
FIG. 51 is a planar development of the structure of an other illustrative embodiment of a connector body constructed in accordance with the invention.

Torsional components combined with bending members may be provided by any of the above-described connector body configurations to engage a larger range of body tissue conduit thicknesses, by combining the strain levels that each member can undergo before permanent deformation occurs. FIG. 51, for example, shows another preferred embodiment of a connector body of the present invention with such components as a planar development of what is actually, preferably, an integral, one-piece connector body, similar to connector body 100 (see, e.g., FIG. 8). As shown, inside aortic fingers 112''' are bending members that may be attached or mounted to annular element 124''' by torsional support members 119''' of connector body 100'''. This geometry may allow the active range of motion of the connector assembly to be on the order of magnitudes greater than that of either the bending members or support members alone. Multiple sets of torsional and bending members may be provided to accommodate a large range of aortic tissue thicknesses and to facilitate a seal with a large range of aortic pressures.

Thus it is seen that connectors for creating an aortic anastomosis whose ostium diameter is larger than that of the graft conduit and methods of use have been provided. One skilled in the art will appreciate that the present invention can be practiced by other than the described embodiments, which are presented for purposes of illustration and not of limitation, and the present invention is limited only by the claims which follow.

What is claimed is:

1. A connector assembly useful for making an anastomotic connection between an opening prepared at an end of a graft tissue conduit and an aperture in a side wall of a body tissue conduit in a patient, said connector assembly comprising:
    a body disposed annularly about a longitudinal axis and having axially spaced distal and proximal portions, the distal portion having an annular element including a graft retention component to secure the tissue of the graft tissue conduit about the opening to the connector assembly, and the proximal portion having a plurality of annularly spaced body fingers, wherein the proximal portion is configured to be delivered into the body tissue conduit through the aperture;
    the body having a constrained condition and an expanded condition, the distal portion in the constrained condition having a first configuration and the proximal portion in the constrained condition having a first configuration in which the plurality of annularly spaced body fingers extend substantially parallel to the longitudinal axis, and the distal portion in the expanded condition having the first configuration and the proximal portion in the expanded condition having a second configuration in which the plurality of annularly spaced body fingers extend generally radially outward from the longitudinal axis,
    wherein the distal portion of the body is configured to be disposed within a lumen defined by an interior surface of the graft tissue conduit, such that an annular inside-retention element of the graft retention component is configured to engage the interior surface of the graft tissue conduit about the opening in an assembled condition.

2. The connector assembly defined in claim 1, wherein the anastomotic connection has an ostium diameter larger than a cross-sectional area of the graft tissue conduit in a direction orthogonal to the longitudinal axis.

3. The connector assembly defined in claim 1, wherein the annular inside-retention element is unitary with the distal portion of the body.

4. The connector assembly defined in claim 1, wherein the annular inside-retention element is coupled to the distal portion of the body.

5. The connector assembly defined in claim 1, wherein the annular inside-retention element includes a plurality of annularly spaced inside-retention members that have free ends configured to engage the interior surface of the graft tissue conduit about the opening in the assembled condition.

6. The connector assembly defined in claim 1, wherein the connector assembly further includes an outside-retention element configured to annularly engage the exterior surface of the graft tissue conduit about the opening in the assembled condition.

7. The connector assembly defined in claim 6, wherein the outside-retention element includes a plurality of annularly spaced outside-retention members.

8. The connector assembly defined in claim 6, wherein the outside-retention element is rigidly connected to the distal portion of the body.

9. The connector assembly defined in claim 6, wherein the outside-retention element is slidably coupled to the distal portion of the body.

10. The connector assembly defined in claim 6, wherein the outside-retention element is further configured to engage the exterior surface of the body tissue conduit about the aperture in the assembled condition.

11. The connector assembly defined in claim 6, wherein the outside-retention element is configured to be at least partially proximal to the inside-retention element in the assembled condition.

12. The connector assembly defined in claim 6, wherein the outside-retention element is configured to be at least partially in the same plane as the inside-retention element in the assembled condition.

13. The connector assembly defined in claim 6, wherein the outside-retention element is a substantially annular expandable band configured to pass annularly about the inside-retention element from a first position distal to the inside-retention element to a second position at least partially proximal to the inside-retention element.

14. The connector assembly defined in claim 13, wherein the connector assembly further includes a collar configured to prevent the band from expanding when in the second position.

15. The connector assembly defined in claim 6, wherein the outside-retention element is hingedly coupled to the distal portion of the body.

16. The connector assembly defined in claim 6, wherein the outside-retention element is constructed of nitinol, tantalum, tungsten, stainless steel, platinum, silicone, or polyurethane.

17. The connector assembly defined in claim 1, wherein movement of the body from the constrained condition to the expanded condition includes a radial outward elastic bending of the plurality of annularly spaced body fingers.

18. The connector assembly defined in claim 1, wherein the body has a medial portion between the proximal portion and the distal portion, wherein the medial portion includes at least one torsional element.

19. The connector assembly defined in claim 1, wherein the opening is prepared by a length-wise axial incision from a toe point at the end of the graft tissue conduit to a heel point along the length of the graft tissue conduit.

20. The connector assembly defined in claim 1, wherein the opening is prepared by an incision oblique to the longitudinal axis of the graft tissue conduit from a toe point at the end of the graft tissue conduit to a first point along the length of the graft tissue conduit followed by a length-wise axial incision from the first point to a heel point further along the length of the graft tissue conduit.

21. An apparatus useful for producing the anastomotic connection between the opening prepared at the end of the graft tissue conduit and the aperture in the side wall of the body tissue conduit in the patient, comprising:
    (1) the connector assembly defined in claim 1; and
    (2) a delivery tool having a first configuration and a second configuration, the first configuration of the delivery tool being adapted to deform the proximal portion of the connector assembly from the second configuration to the first configuration and to advance the proximal portion of the connector assembly in the first configuration into the lumen of the body tissue conduit via the aperture, and the second configuration of the delivery tool being adapted to release the proximal portion of the connector assembly for movement to the second configuration in the lumen of the body tissue conduit.

22. The apparatus defined in claim 21, further comprising a loading tool having a body portion, wherein the body portion is configured to support the distal portion of the connector assembly and to define the resulting shape of the anastomotic connection external to the body tissue conduit.

23. The apparatus defined in claim 22, wherein the loading tool is external to a cannulation of the connector assembly.

24. The apparatus defined in claim 22, wherein the loading tool further includes at least one tissue holder configured to engage the exterior surface of the graft tissue conduit about the opening and to hold the graft tissue conduit about the graft retention component of the connector assembly.

25. The apparatus defined in claim 21, wherein the anastomotic connection has an ostium diameter larger than a cross-sectional area of the graft tissue conduit in a direction orthogonal to the longitudinal axis.

26. The apparatus defined in claim 21, wherein the connector assembly further includes an outside-retention element configured to annularly engage the exterior surface of the graft tissue conduit about the opening in an assembled condition.

27. The apparatus defined in claim 21, wherein the annular element has a fixed cross-sectional area.

28. The connector assembly defined in claim 1, wherein the annular element has a fixed cross-sectional area.

29. The connector assembly defined in claim 28, wherein the fixed cross-sectional area defines a round, oval, or any other substantially smooth shape.

30. The connector assembly defined in claim 1, wherein the graft retention component is a fixed part of the annular element, or is connected to the annular element.

31. The connector assembly defined in claim 1, wherein the connector assembly is constructed of nitinol, tantalum, tungsten, stainless steel, platinum, silicone, or polyurethane.

32. The connector assembly defined in claim 1, wherein the annular inside-retention element is constructed of nitinol, tantalum, tungsten, stainless steel, platinum, silicone, or polyurethane.

33. The connector assembly defined in claim 1, wherein the proximal portion is axially spaced from the distal portion in the constrained and expanded conditions.

34. A connector assembly useful for making an anastomotic connection between an opening prepared at an end of a graft tissue conduit and an aperture in a side wall of a body tissue conduit in a patient, said connector assembly comprising:
   a body disposed annularly about a longitudinal axis and having axially spaced distal and proximal portions, the distal portion having an annular element including a graft retention component to secure the tissue of the graft tissue conduit about the opening to the connector assembly, and the proximal portion having a plurality of annularly spaced body fingers adapted to expand radially out to engage the interior surface of the side wall of the body tissue conduit about the aperture, the annular element being continuous in a plane orthogonal to the longitudinal axis, wherein the proximal portion is configured to be delivered into the body tissue conduit through the aperture,
   wherein the distal portion of the body is configured to be disposed within a lumen defined by an interior surface of the graft tissue conduit, such that an annular inside-retention element of the graft retention component is configured to engage the interior surface of the graft tissue conduit about the opening in an assembled condition.

35. The connector assembly defined in claim 34, wherein the proximal portion is axially spaced from the distal portion in the constrained and expanded conditions.

36. A method of producing an anastomotic connection between an opening prepared at an end of a graft tissue conduit and an aperture in a side wall of a body tissue conduit in a patient, the method comprising:
   (1) securing the tissue of the graft tissue conduit about the opening to the graft retention component of the distal portion of the connector assembly of claim 1;
   (2) deforming the plurality of annularly spaced body fingers at the proximal portion of the connector assembly, and approximating the opening and the aperture so that the proximal portion of the connector assembly extends into the body tissue conduit via the aperture;
   (3) un-deforming the proximal portion so that the plurality of annularly spaced body fingers expand radially out to engage the interior surface of the side wall of the body tissue conduit about the aperture.

37. The method of claim 36, wherein the securing comprises: positioning the graft tissue conduit so that the interior surface of the graft tissue conduit about the opening engages the annular inside-retention element of the graft retention component; and positioning an outside-retention element of the connector assembly to engage the exterior surface of the graft tissue about the opening at least partially proximal to the annular inside-retention element.

38. The method of claim 37, wherein the securing further comprises: before the positioning the graft tissue conduit, providing a loading tool having a body portion configured to hold the distal portion of the connector assembly to define the resulting shape of the anastomotic connection external to the body tissue conduit.

39. The method of claim 36, wherein the deforming comprises: providing a delivery tool with a noose threaded through an eyelet provided by each of the body fingers; and tightening the noose so that each body finger is variably constrained radially from a fully undeformed configuration to a fully deformed configuration.

40. The method of claim 39, wherein the approximating comprises: advancing the delivery tool so that the plurality of body fingers extend into the body tissue conduit via the aperture.

41. The method of claim 39, wherein the undeforming comprises: releasing the noose.

42. The method of claim 39, wherein the delivery tool does not cannulate the connector assembly or the graft tissue conduit.

43. The method of claim 36, wherein the anastomotic connection has an ostium diameter larger than the cross-sectional area of the graft tissue conduit.

44. The method of claim 36, wherein said anastomotic connection takes off at an angle that is not tangential or perpendicular.

45. The method of claim 36, wherein the opening is prepared by a length-wise axial incision from a toe point at the end of the graft tissue conduit to a heel point along the length of the graft tissue conduit.

46. The method of claim 36, wherein the opening is prepared by an incision oblique to the longitudinal axis of the graft tissue conduit from a toe point at the end of the graft tissue conduit to a first point along the length of the graft tissue conduit followed by a length-wise axial incision from the first point to a heel point further along the length of the graft tissue conduit.

* * * * *